United States Patent
Bremond et al.

(10) Patent No.: US 10,619,174 B2
(45) Date of Patent: *Apr. 14, 2020

(54) MICROORGANISM STRAINS FOR THE PRODUCTION OF 2,3-BUTANEDIOL

(71) Applicant: ALDERYS, Orsay (FR)

(72) Inventors: Mélanie Bremond, Le Plessis Robinson (FR); Karine Jaillardon, St Michel sur Orge (FR); Dominique Louis, Forges les Bains (FR); Dominique Thomas, Gif sur Yvette (FR)

(73) Assignee: ALDERYS, Orsay (FR)

( * ) Notice: Subject to any disclaimer, the term of this patent is extended or adjusted under 35 U.S.C. 154(b) by 285 days.

This patent is subject to a terminal disclaimer.

(21) Appl. No.: 15/327,181

(22) PCT Filed: Jul. 23, 2015

(86) PCT No.: PCT/EP2015/066920
§ 371 (c)(1),
(2) Date: Jan. 18, 2017

(87) PCT Pub. No.: WO2016/012557
PCT Pub. Date: Jan. 28, 2016

(65) Prior Publication Data
US 2017/0166935 A1    Jun. 15, 2017

(30) Foreign Application Priority Data
Jul. 25, 2014 (EP) .................................... 14306202

(51) Int. Cl.
*C12P 7/18* (2006.01)
*C12N 9/04* (2006.01)
*C12N 9/02* (2006.01)
*C12N 9/10* (2006.01)
*C12N 9/88* (2006.01)
*C12N 15/52* (2006.01)

(52) U.S. Cl.
CPC .............. *C12P 7/18* (2013.01); *C12N 9/0006* (2013.01); *C12N 9/0036* (2013.01); *C12N 9/1022* (2013.01); *C12N 9/88* (2013.01); *C12N 15/52* (2013.01); *C12Y 101/01004* (2013.01); *C12Y 106/03* (2013.01); *C12Y 202/01006* (2013.01); *C12Y 401/01001* (2013.01); *C12Y 401/01005* (2013.01)

(58) Field of Classification Search
None
See application file for complete search history.

(56) References Cited

U.S. PATENT DOCUMENTS

2011/0124060 A1 * 5/2011 Anthony .............. C12N 9/1205
                                                              435/115
2013/0244243 A1 * 9/2013 Matsuyama ........... C12N 15/81
                                                              435/6.13

FOREIGN PATENT DOCUMENTS

WO     WO-2011041426 A1 * 4/2011 ........... C12N 9/1205

OTHER PUBLICATIONS

Vemuri, G.N., et al. 2007 PNAS 104(7): 2402-2407. (Year: 2007).*
Blomqvist, K., et al. 1993 Journal of Bacteriology 175(5): 1392-1404 (Year: 1993).*
Shao, Z., et al. 2008 Nucleic Acids Research 37(2): 1-10. (Year: 2008).*

* cited by examiner

*Primary Examiner* — Marsha Tsay
(74) *Attorney, Agent, or Firm* — W & C IP

(57) ABSTRACT

A recombinant yeast having a reduced pyruvate decarboxylase activity, in the génome of which has been inserted: —one or more nucleic acids encoding an acetolactate synthase or ALS, —one or more nucleic acids encoding an acetolactate decarboxylase or ALD, —one or more nucleic acids encoding a butanediol dehydrogenase or BDH, and —one or more copies of a nucleic acids encoding a NADH oxidase or NOXE.

12 Claims, 1 Drawing Sheet
Specification includes a Sequence Listing.

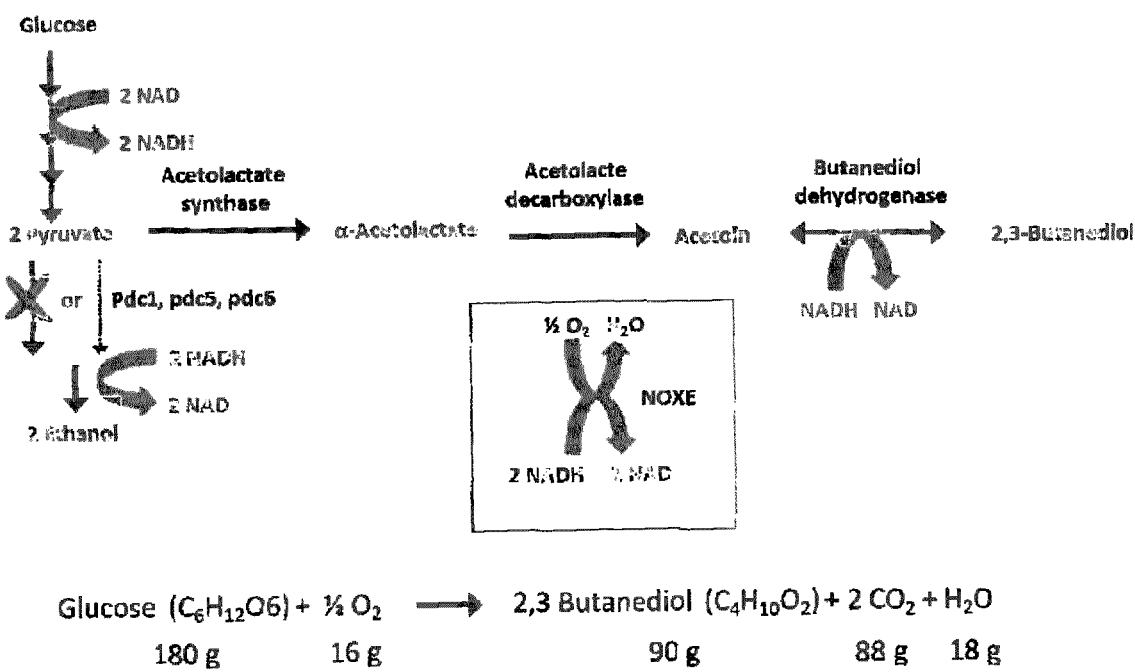

SEQUENCE LISTING

<160> NUMBER OF SEQ ID NOS: 56

<210> SEQ ID NO 1
<211> LENGTH: 1716
<212> TYPE: DNA
<213> ORGANISM: Bacillus subtilis
<220> FEATURE:
<221> NAME/KEY: source
<222> LOCATION: 1..1716
<223> OTHER INFORMATION: /mol_type="DNA"
      /organism="Bacillus subtilis"

<400> SEQUENCE: 1
atgtctacca aagcaacaaa agagcaaaag agccttgtga agaatagagg tgcagaactt      60
gtcgttgatt gcttggtaga acagggagtc actcacgttt tcgggatacc cggcgctaaa    120

```
atcgacgccg tgtttgacgc tttacaggat aagggaccag agatcattgt tgctagacat    180
gaacagaatg cagcgttcat ggctcaagct gtaggtagac ttactgggaa acccggtgtg    240
gttttggtta ctagtggacc aggtgcatca aatctagcaa caggtttgtt aacagcgaat    300
acagagggag atcctgttgt tgcattagca ggaaacgtta tcagagcgga tagactgaaa    360
agaacccatc aatcattgga taatgctgca ttatttcagc caattacgaa atattccgtc    420
gaagtacagg atgtgaagaa catacctgaa gctgtaacta atgcgtttcg tatagcttct    480
gctggtcaag ctggtgcagc ttttgtttcg tttccgcaag acgttgtcaa cgaggttacg    540
aacactaaga atgtgagagc agtagcagcc ccaaaattag accagctgc tgatgatgct     600 atatcagctg ctattgctaa gattcagaca gccaaactac tgttgtctt agtaggtatg     660 aaaggtggca ggccagaagc aatcaaggca gttagaaaac tgttgaagaa ggttcaattg    720
ccgtttgtgg aaacctatca agccgcaggg actttgtcta gggatctaga agatcaatac    780
ttcggtagaa tagggttgtt cagaaatcaa cctggcgact tgttactgga acaagccgat    840
gtcgtgctta caattggtta cgatccgatt gaatatgacc ccaaattttg gaatattaat    900
ggtgatagga ctattatcca cttagacgag attattgccg atattgacca tgcttatcaa    960
cctgatctgg aactgatagg tgatattcca agtactatca accatataga gcatgatgcc    1020
gtcaaagtgg aatttgccga agagaacag aagatcctat ccgatctaaa gcagtacatg     1080
catgaaggcg aacaagttcc agcagattgg aaatccgata gagcacatcc attggaaatt    1140
gtcaaagaat tgagaaatgc agttgatgac catgttacag ttacttgtga cataggtagt    1200
cacgctattt ggatgtctag gtacttcaga tcttatgagc cattaacgtt gatgatatcc    1260
aatggcatgc aaacccttgg agtcgcttta ccatgggcca ttggtgcgtc gttagtaaag    1320
ccaggagaga aagtcgttc tgtgtcaggt gatggtggtt tcttgttctc tgccatggaa    1380
ttggaaaccg ccgttcgttt gaaagcccct atagtacaca tcgtgtggaa tgattcgacc    1440
tatgacatgg tcgcgtttca acaattgaag aagtacaacc gtacttcagc tgttgatttc    1500
ggcaacattg acattgtgaa gtacgcggaa agctttggcg ccacaggcct aagagtcgaa    1560
tcacctgatc aattagcaga tgtacttagg caagggatga acgctgaagg acctgtaatt    1620
atcgacgtac tgttgactga tagcgacaac atcaatttag ccagtgataa attacccaaa    1680
gagtttggtg agctaatgaa aacgaaagct ttgtaa                              1716
```

<210> SEQ ID NO 2
<211> LENGTH: 571
<212> TYPE: PRT
<213> ORGANISM: Bacillus subtilis
<220> FEATURE:
<221> NAME/KEY: SOURCE
<222> LOCATION: 1..571
<223> OTHER INFORMATION: /mol_type="protein"
     /organism="Bacillus subtilis"

<400> SEQUENCE: 2

Met Ser Thr Lys Ala Thr Lys Glu Gln Lys Ser Leu Val Lys Asn Arg
1               5                   10                  15

Gly Ala Glu Leu Val Val Asp Cys Leu Val Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

```
Ala Phe Met Ala Gln Ala Val Gly Arg Leu Thr Gly Lys Pro Gly Val
 65                  70                  75                  80

Val Leu Val Thr Ser Gly Pro Gly Ala Ser Asn Leu Ala Thr Gly Leu
             85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
        450                 455                 460

Val Arg Leu Lys Ala Pro Ile Val His Ile Val Trp Asn Asp Ser Thr
465                 470                 475                 480
```

```
Tyr Asp Met Val Ala Phe Gln Gln Leu Lys Lys Tyr Asn Arg Thr Ser
            485                 490                 495

Ala Val Asp Phe Gly Asn Ile Asp Ile Val Lys Tyr Ala Glu Ser Phe
        500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570
```

<210> SEQ ID NO 3
<211> LENGTH: 1995
<212> TYPE: DNA
<213> ORGANISM: Nicotiana tabacum
<220> FEATURE:
<221> NAME/KEY: source
<222> LOCATION: 1..1995
<223> OTHER INFORMATION: /mol_type="DNA"
      /organism="Nicotiana tabacum"

<400> SEQUENCE: 3

| | | | | | |
|---|---|---|---|---|---|
| atggctgctg | ctgcagctgc | tccatctcca | tcttttcta | aaaccttgtc | ctcctcctct | 60 |
| tccaaatctt | ctactttgtt | gccaagatct | actttcccat | ttccacatca | tccacataag | 120 |
| actactccac | caccattgca | tttgactcca | actcatattc | actcccaaag | aagaagattc | 180 |
| accatctcca | acgttatttc | taccacccaa | aaggtttctg | aaactcaaaa | ggctgaaacc | 240 |
| ttcgtttcta | gatttgctcc | agatgaacct | agaaagggtt | ctgatgtttt | ggttgaagct | 300 |
| ttggaaagag | aaggtgttac | cgatgttttt | gcttatccag | gtggtgcttc | tatggaaatt | 360 |
| catcaagctt | tgaccagatc | ctccatcatt | agaaatgttt | tgccaagaca | tgaacaaggt | 420 |
| ggtgttttcg | ctgctgaagg | ttatgctaga | gctactggtt | ttccaggtgt | atgtattgct | 480 |
| acttctggtc | caggtgctac | taatttggtt | tctggtttgg | ctgatgcttt | gttggattct | 540 |
| gttccaatcg | ttgctattac | tggtcaagtt | ccaagaagaa | tgattggtac | agatgctttc | 600 |
| caagaaaccc | caattgtcga | agttactaga | tctattacca | agcacaacta | cttggttatg | 660 |
| gacgttgaag | atatcccaag | agttgttaga | gaagcatttt | tcttggctag | atctggtaga | 720 |
| ccaggtccag | ttttgattga | tgttccaaag | gatatccaac | aacaattggt | tatcccagat | 780 |
| tgggaccaac | ctatgagatt | gccaggttat | atgtctagat | tgccaaagtt | gccaaacgaa | 840 |
| atgttgttag | aacaaatcgt | cagattgatc | tccgaatcta | aaaagccagt | cttgtatgtt | 900 |
| ggtggtggtt | gttctcaatc | tagtgaagaa | ttgagaagat | cgtcgaatt | gaccggtatt | 960 |
| ccagttgctt | ctacattgat | gggtttgggt | gcttttccaa | ctggtgatga | attgtctttg | 1020 |
| tctatgttgg | gtatgcacgg | tactgtttat | gctaattacg | ctgttgattc | ctccgatttg | 1080 |
| ttgttagctt | ttggtgttag | attcgatgat | agagtcactg | gtaagttgga | agcttttgct | 1140 |
| tctagagcta | gatcgttca | tatcgacatt | gattccgctg | aaatcggtaa | aaacaagcaa | 1200 |
| ccacatgttt | ctatttgcgc | cgatattaag | ttggcattgc | aaggtttgaa | cagtatcttg | 1260 |
| gaatccaaag | aaggtaaatt | gaagttggac | ttctctgctt | ggagacaaga | attgacagtt | 1320 |
| caaaaggtta | agtacccatt | gaacttcaag | actttcggtg | atgctattcc | accacaatac | 1380 |
| gctattcaag | tttttgatga | attgaccaac | ggttccgcta | ttatttcaac | tggtgttggt | 1440 |

-continued

```
caacatcaaa tgtgggctgc tcaatattac aagtacagaa aacctagaca atggttgact    1500
tctggtggtt taggtgctat gggttttggt ttgccagctg ctattggtgc tgctgttggt    1560
agacctgatg aagttgttgt agatattgat ggtgacggtt ccttcattat gaacgtccaa    1620
gaattggcta ccatcaaggt tgaaaatttg ccagtcaaga tcatgttatt gaacaatcaa    1680
cacttgggta tggtcgtcca atgggaagat agattttaca aagctaatag agcccacacc    1740
tacttgggta atccatctaa tgaagctgaa atcttcccaa acatgttgaa gtttgctgaa    1800
gcttgtggtg ttccagctgc aagagttact catagagatg atttgagagc tgccatccaa    1860
aagatgttgg atactccagg tccatacttg ttggatgtta ttgtcccaca tcaagaacat    1920
gtcttgccaa tgattccatc tggtggtgcc tttaaagatg ttattactga aggtgacggt    1980
agatcctctt actga                                                    1995
```

<210> SEQ ID NO 4
<211> LENGTH: 664
<212> TYPE: PRT
<213> ORGANISM: Nicotiana tabacum
<220> FEATURE:
<221> NAME/KEY: SOURCE
<222> LOCATION: 1..664
<223> OTHER INFORMATION: /mol_type="protein"
      /organism="Nicotiana tabacum"

<400> SEQUENCE: 4

```
Met Ala Ala Ala Ala Ala Pro Ser Pro Ser Phe Ser Lys Thr Leu
1               5                   10                  15

Ser Ser Ser Ser Ser Lys Ser Ser Thr Leu Leu Pro Arg Ser Thr Phe
                20                  25                  30

Pro Phe Pro His His Pro His Lys Thr Thr Pro Pro Leu His Leu
            35                  40                  45

Thr Pro Thr His Ile His Ser Gln Arg Arg Phe Thr Ile Ser Asn
        50                  55                  60

Val Ile Ser Thr Thr Gln Lys Val Ser Glu Thr Gln Lys Ala Glu Thr
65                  70                  75                  80

Phe Val Ser Arg Phe Ala Pro Asp Glu Pro Arg Lys Gly Ser Asp Val
                85                  90                  95

Leu Val Glu Ala Leu Glu Arg Glu Gly Val Thr Asp Val Phe Ala Tyr
            100                 105                 110

Pro Gly Gly Ala Ser Met Glu Ile His Gln Ala Leu Thr Arg Ser Ser
        115                 120                 125

Ile Ile Arg Asn Val Leu Pro Arg His Glu Gln Gly Gly Val Phe Ala
    130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175

Leu Leu Asp Ser Val Pro Ile Val Ala Ile Thr Gly Gln Val Pro Arg
            180                 185                 190

Arg Met Ile Gly Thr Asp Ala Phe Gln Glu Thr Pro Ile Val Glu Val
        195                 200                 205

Thr Arg Ser Ile Thr Lys His Asn Tyr Leu Val Met Asp Val Glu Asp
    210                 215                 220

Ile Pro Arg Val Val Arg Glu Ala Phe Phe Leu Ala Arg Ser Gly Arg
225                 230                 235                 240

Pro Gly Pro Val Leu Ile Asp Val Pro Lys Asp Ile Gln Gln Gln Leu
```

-continued

```
                245                 250                 255
Val Ile Pro Asp Trp Asp Gln Pro Met Arg Leu Pro Gly Tyr Met Ser
            260                 265                 270

Arg Leu Pro Lys Leu Pro Asn Glu Met Leu Leu Glu Gln Ile Val Arg
        275                 280                 285

Leu Ile Ser Glu Ser Lys Lys Pro Val Leu Tyr Val Gly Gly Gly Cys
    290                 295                 300

Ser Gln Ser Ser Glu Glu Leu Arg Arg Phe Val Glu Leu Thr Gly Ile
305                 310                 315                 320

Pro Val Ala Ser Thr Leu Met Gly Leu Gly Ala Phe Pro Thr Gly Asp
                325                 330                 335

Glu Leu Ser Leu Ser Met Leu Gly Met His Gly Thr Val Tyr Ala Asn
            340                 345                 350

Tyr Ala Val Asp Ser Ser Asp Leu Leu Leu Ala Phe Gly Val Arg Phe
        355                 360                 365

Asp Asp Arg Val Thr Gly Lys Leu Glu Ala Phe Ala Ser Arg Ala Lys
    370                 375                 380

Ile Val His Ile Asp Ile Asp Ser Ala Glu Ile Gly Lys Asn Lys Gln
385                 390                 395                 400

Pro His Val Ser Ile Cys Ala Asp Ile Lys Leu Ala Leu Gln Gly Leu
                405                 410                 415

Asn Ser Ile Leu Glu Ser Lys Glu Gly Lys Leu Lys Leu Asp Phe Ser
            420                 425                 430

Ala Trp Arg Gln Glu Leu Thr Val Gln Lys Val Lys Tyr Pro Leu Asn
        435                 440                 445

Phe Lys Thr Phe Gly Asp Ala Ile Pro Pro Gln Tyr Ala Ile Gln Val
    450                 455                 460

Leu Asp Glu Leu Thr Asn Gly Ser Ala Ile Ile Ser Thr Gly Val Gly
465                 470                 475                 480

Gln His Gln Met Trp Ala Ala Gln Tyr Tyr Lys Tyr Arg Lys Pro Arg
                485                 490                 495

Gln Trp Leu Thr Ser Gly Gly Leu Gly Ala Met Gly Phe Gly Leu Pro
            500                 505                 510

Ala Ala Ile Gly Ala Ala Val Gly Arg Pro Asp Glu Val Val Val Asp
        515                 520                 525

Ile Asp Gly Asp Gly Ser Phe Ile Met Asn Val Gln Glu Leu Ala Thr
    530                 535                 540

Ile Lys Val Glu Asn Leu Pro Val Lys Ile Met Leu Leu Asn Asn Gln
545                 550                 555                 560

His Leu Gly Met Val Val Gln Trp Glu Asp Arg Phe Tyr Lys Ala Asn
                565                 570                 575

Arg Ala His Thr Tyr Leu Gly Asn Pro Ser Asn Glu Ala Glu Ile Phe
            580                 585                 590

Pro Asn Met Leu Lys Phe Ala Glu Ala Cys Gly Val Pro Ala Ala Arg
        595                 600                 605

Val Thr His Arg Asp Asp Leu Arg Ala Ala Ile Gln Lys Met Leu Asp
    610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655

Glu Gly Asp Gly Arg Ser Ser Tyr
            660
```

<210> SEQ ID NO 5
<211> LENGTH: 1746
<212> TYPE: DNA
<213> ORGANISM: Paenibacillus polymyxa
<220> FEATURE:
<221> NAME/KEY: source
<222> LOCATION: 1..1746
<223> OTHER INFORMATION: /mol_type="DNA"
      /organism="Paenibacillus polymyxa"

<400> SEQUENCE: 5

```
atgtccgcac aaatacctga agttagaagt acaaatgaat tgagagaaaa atggatgaag      60
cctgaagtaa tcactggttc cgaaatattg ttaagatcat tgttattgga aggtgtcgat     120
tgtgtatttg gttatccagg tggtgctgtc ttgtacatct atgatgcaat gtacggtttt     180
aaagacttca agcatgtttt aaccagacac gaacaaggtg ctatacatgc tgcagatggt     240
tatgccagag cttccggtaa agtaggtgtt tgcatcgcaa caagtggtcc aggtgccacc     300
aatttggtta ctggtatcgc aacagccttt atggattctg ttcctttggt tgtcattact     360
ggtaacgtca tttcttcatt aatcggtaca gatgcattcc aagaagccga cataactggt     420
atcacaatgc caataactaa gcactcatat tggttagaag atgtcgaaga cttgcctaga     480
ataatccatg aagcatttca catagcaaat acaggtagaa agggtccagt tttgatagat     540
atccctaaag acatatccgc cgctcaaacc ttattcgtac cacaaaccgg tcctgttact     600
atgagaggtt acaacccaaa ggttttgcct aacaagatac aattggataa attgacacaa     660
gccatctccg aagctgaaag accattcatt ttggcaggtg gtggtgtagt ttatagtggt     720
ggtcatgaag ccttatacga atttgttaga aagactgaaa tccctatcac tacaacctta     780
ttgggtttag gtggtttccc atcaggtcat gaattgtgga ctggtatgcc tggtatgcac     840
ggtacataca cctccaatca agcaatacaa catctgatt tgttgatctg tattggtgct     900
agatttgatg acagagttac tggtaaattg gatggtttcg caccacaagc caaaattgta     960
catatagata tcgaccctgc agaaataggt aaaaatgttg cagccgatat tccaatagta    1020
ggtgacgtta aggctgtctt agaattattg aaccaagatg ttaagagagc cgatagagct    1080
gacgcatgga gagcacaaat ccaacattgg aagaacgaaa agccatattc ctacaaggat    1140
agtgaaacag ttttgaaacc tcaatgggtc gtagaattat ggatgaaaac tacaaagggt    1200
ggtgctattg tcaccactga cgtaggtcaa caccaaatgt gggctgcaca atactacaag    1260
tttaatcaac caagatcatg ggttacatca ggtggtttag gtactatggg ttttggtttc    1320
ccatctgcta ttggtgcaca aatggccaat cctgatagat tggttatctc tattaacggt    1380
gacggtggta tgcaaatgtg ttcacaagaa ttagctattt cgctcattaa taacatccca    1440
gtaaagatcg ttatcattaa taccaagtt ttgggtatgg tcagacaatg gcaagaattg    1500
atctataaca acagatactc tcatattgat ttggctggtt cacctgactt tgtcaaattg    1560
gccgaagcct atggtgtaaa gggtttaaga gcaaccaata aggaagaagc cagaagagct    1620
tggcaagaag cattggatac tccaggtcct gttgtcgtag aatttgttgt ctctaaagaa    1680
gaaaacgttt atccaatggt tacacaaggt tccacaatag accaaatgtt gatgggtgac    1740
gaatga                                                               1746
```

<210> SEQ ID NO 6
<211> LENGTH: 581
<212> TYPE: PRT
<213> ORGANISM: Paenibacillus polymyxa

```
<220> FEATURE:
<221> NAME/KEY: SOURCE
<222> LOCATION: 1..581
<223> OTHER INFORMATION: /mol_type="protein"
      /organism="Paenibacillus polymyxa"

<400> SEQUENCE: 6

Met Ser Ala Gln Ile Pro Glu Val Arg Ser Thr Asn Glu Leu Arg Glu
1               5                   10                  15

Lys Trp Met Lys Pro Glu Val Ile Thr Gly Ser Glu Ile Leu Arg
            20                  25                  30

Ser Leu Leu Leu Glu Gly Val Asp Cys Val Phe Gly Tyr Pro Gly Gly
        35                  40                  45

Ala Val Leu Tyr Ile Tyr Asp Ala Met Tyr Gly Phe Lys Asp Phe Lys
    50                  55                  60

His Val Leu Thr Arg His Glu Gln Gly Ala Ile His Ala Ala Asp Gly
65                  70                  75                  80

Tyr Ala Arg Ala Ser Gly Lys Val Gly Val Cys Ile Ala Thr Ser Gly
                85                  90                  95

Pro Gly Ala Thr Asn Leu Val Thr Gly Ile Ala Thr Ala Phe Met Asp
            100                 105                 110

Ser Val Pro Leu Val Val Ile Thr Gly Asn Val Ile Ser Ser Leu Ile
        115                 120                 125

Gly Thr Asp Ala Phe Gln Glu Ala Asp Ile Thr Gly Ile Thr Met Pro
    130                 135                 140

Ile Thr Lys His Ser Tyr Leu Val Arg Asp Val Glu Asp Leu Pro Arg
145                 150                 155                 160

Ile Ile His Glu Ala Phe His Ile Ala Asn Thr Gly Arg Lys Gly Pro
                165                 170                 175

Val Leu Ile Asp Ile Pro Lys Asp Ile Ser Ala Ala Gln Thr Leu Phe
            180                 185                 190

Val Pro Gln Thr Gly Pro Val Thr Met Arg Gly Tyr Asn Pro Lys Val
        195                 200                 205

Leu Pro Asn Lys Ile Gln Leu Asp Lys Leu Thr Gln Ala Ile Ser Glu
    210                 215                 220

Ala Glu Arg Pro Phe Ile Leu Ala Gly Gly Gly Val Val Tyr Ser Gly
225                 230                 235                 240

Gly His Glu Ala Leu Tyr Glu Phe Val Arg Lys Thr Glu Ile Pro Ile
                245                 250                 255

Thr Thr Thr Leu Leu Gly Leu Gly Gly Phe Pro Ser Gly His Glu Leu
            260                 265                 270

Trp Thr Gly Met Pro Gly Met His Gly Thr Tyr Thr Ser Asn Gln Ala
        275                 280                 285

Ile Gln Gln Ser Asp Leu Leu Ile Cys Ile Gly Ala Arg Phe Asp Asp
    290                 295                 300

Arg Val Thr Gly Lys Leu Asp Gly Phe Ala Pro Gln Ala Lys Ile Val
305                 310                 315                 320

His Ile Asp Ile Asp Pro Ala Glu Ile Gly Lys Asn Val Ala Ala Asp
                325                 330                 335

Ile Pro Ile Val Gly Asp Val Lys Ala Val Leu Glu Leu Leu Asn Gln
            340                 345                 350

Asp Val Lys Arg Ala Asp Arg Ala Asp Ala Trp Arg Ala Gln Ile Gln
        355                 360                 365

His Trp Lys Asn Glu Lys Pro Tyr Ser Tyr Lys Asp Ser Glu Thr Val
    370                 375                 380
```

```
Leu Lys Pro Gln Trp Val Val Glu Leu Leu Asp Glu Thr Thr Lys Gly
385                 390                 395                 400

Gly Ala Ile Val Thr Thr Asp Val Gly Gln His Gln Met Trp Ala Ala
            405                 410                 415

Gln Tyr Tyr Lys Phe Asn Gln Pro Arg Ser Trp Val Thr Ser Gly Gly
        420                 425                 430

Leu Gly Thr Met Gly Phe Gly Phe Pro Ser Ala Ile Gly Ala Gln Met
    435                 440                 445

Ala Asn Pro Asp Arg Leu Val Ile Ser Ile Asn Gly Asp Gly Gly Met
450                 455                 460

Gln Met Cys Ser Gln Glu Leu Ala Ile Cys Ala Ile Asn Asn Ile Pro
465                 470                 475                 480

Val Lys Ile Val Ile Asn Asn Gln Val Leu Gly Met Val Arg Gln
            485                 490                 495

Trp Gln Glu Leu Ile Tyr Asn Asn Arg Tyr Ser His Ile Asp Leu Ala
                500                 505                 510

Gly Ser Pro Asp Phe Val Lys Leu Ala Glu Ala Tyr Gly Val Lys Gly
        515                 520                 525

Leu Arg Ala Thr Asn Lys Glu Glu Ala Arg Ala Trp Gln Glu Ala
    530                 535                 540

Leu Asp Thr Pro Gly Pro Val Val Glu Phe Val Val Ser Lys Glu
545                 550                 555                 560

Glu Asn Val Tyr Pro Met Val Thr Gln Gly Ser Thr Ile Asp Gln Met
                565                 570                 575

Leu Met Gly Asp Glu
            580

<210> SEQ ID NO 7
<211> LENGTH: 860
<212> TYPE: DNA
<213> ORGANISM: Brevibacillus brevis
<220> FEATURE:
<221> NAME/KEY: source
<222> LOCATION: 1..860
<223> OTHER INFORMATION: /mol_type="DNA"
      /organism="Brevibacillus brevis"

<400> SEQUENCE: 7
atgggtaaga agaacattat tacctctatc acctccttgg ctttggttgc tggtttgtct      60
ttgactgctt ttgctgctac tactgctact gttccagctc caccagctaa acaagaatct    120
aaaccagctg ttgctgctaa tccagctcct aagaatgttt tgttccaata ctctaccatc    180
aacgccttga tgttgggtca atttgaaggt gatttgacct tgaaggactt gaagttgaga    240
ggtgatatgg gtttgggtac tatcaatgat ttggacggtg aaatgatcca aatgggtact    300
aagttctacc aaatcgattc taccggtaag ttgtctgaat gccagaatc tgttaagact    360 ccattcgctg ttactactca cttcgaacct aaagaaaaga ctaccttgac caacgtccaa    420
gactacaatc aattgaccaa gatgttggaa gaaaagttcg aaaacaagaa cgttttctac    480
gccgttaagt tgactggtac tttcaaaatg gttaaggcta gaaccgttcc taagcaaact    540
agaccatatc acaattgac tgaagtcacc aagaagcaat ccgaatttga attcaagaac    600
gtcaagggta ctttgatcgg ttttacact ccaaattatg ctgctgcttt gaacgttcca    660
ggttttcact tgcatttcat taccgaagat aagacctctg tggtcatgt tttgaacttg    720 caatttgata acgccaactt ggaaatctcc ccaatccatg aatttgatgt tcaattgcca    780
```

```
cacaccgatg atttcgctca ttctgatttg actcaagtta ctacctccca agttcatcaa       840
gctgaatctg aaagaaagta                                                   860
```

<210> SEQ ID NO 8
<211> LENGTH: 286
<212> TYPE: PRT
<213> ORGANISM: Brevibacillus brevis
<220> FEATURE:
<221> NAME/KEY: SOURCE
<222> LOCATION: 1..286
<223> OTHER INFORMATION: /mol_type="protein"
      /organism="Brevibacillus brevis"

<400> SEQUENCE: 8

```
Met Gly Lys Lys Asn Ile Ile Thr Ser Ile Thr Ser Leu Ala Leu Val
1               5                  10                  15

Ala Gly Leu Ser Leu Thr Ala Phe Ala Ala Thr Thr Ala Thr Val Pro
            20                  25                  30

Ala Pro Pro Ala Lys Gln Glu Ser Lys Pro Ala Val Ala Ala Asn Pro
        35                  40                  45

Ala Pro Lys Asn Val Leu Phe Gln Tyr Ser Thr Ile Asn Ala Leu Met
    50                  55                  60

Leu Gly Gln Phe Glu Gly Asp Leu Thr Leu Lys Asp Leu Lys Leu Arg
65                  70                  75                  80

Gly Asp Met Gly Leu Gly Thr Ile Asn Asp Leu Asp Gly Glu Met Ile
                85                  90                  95

Gln Met Gly Thr Lys Phe Tyr Gln Ile Asp Ser Thr Gly Lys Leu Ser
            100                 105                 110

Glu Leu Pro Glu Ser Val Lys Thr Pro Phe Ala Val Thr Thr His Phe
        115                 120                 125

Glu Pro Lys Glu Lys Thr Thr Leu Thr Asn Val Gln Asp Tyr Asn Gln
    130                 135                 140

Leu Thr Lys Met Leu Glu Glu Lys Phe Glu Asn Lys Asn Val Phe Tyr
145                 150                 155                 160

Ala Val Lys Leu Thr Gly Thr Phe Lys Met Val Lys Ala Arg Thr Val
                165                 170                 175

Pro Lys Gln Thr Arg Pro Tyr Pro Gln Leu Thr Glu Val Thr Lys Lys
            180                 185                 190

Gln Ser Glu Phe Glu Phe Lys Asn Val Lys Gly Thr Leu Ile Gly Phe
        195                 200                 205

Tyr Thr Pro Asn Tyr Ala Ala Ala Leu Asn Val Pro Gly Phe His Leu
    210                 215                 220

His Phe Ile Thr Glu Asp Lys Thr Ser Gly Gly His Val Leu Asn Leu
225                 230                 235                 240

Gln Phe Asp Asn Ala Asn Leu Glu Ile Ser Pro Ile His Glu Phe Asp
                245                 250                 255

Val Gln Leu Pro His Thr Asp Asp Phe Ala His Ser Asp Leu Thr Gln
            260                 265                 270

Val Thr Thr Ser Gln Val His Gln Ala Glu Ser Glu Arg Lys
        275                 280                 285
```

<210> SEQ ID NO 9
<211> LENGTH: 783
<212> TYPE: DNA
<213> ORGANISM: Enterobacter aerogenes
<220> FEATURE:
<221> NAME/KEY: source
<222> LOCATION: 1..783

<223> OTHER INFORMATION: /mol_type="DNA"
/organism="Enterobacter aerogenes"

<400> SEQUENCE: 9

```
atgatgatgc actcctccgc ctgcgactgt gaagcaagtt tatgcgaaac attgagaggt      60
ttttccgcca agcacccaga ttccgttata tatcaaacat ccttgatgag tgctttgtta     120
tctggtgtct acgaaggtga cactacaatc gcagacttgt tagctcatgg tgactttggt     180
ttgggtactt ttaatgaatt agacggtgaa atgatcgcat tttcttcaca agttaccaa      240
ttgagagctg atggttcagc aagagctgca aaaccagaac aaaagacacc ttttgcagtc     300
atgacctggt tccaaccaca atacagaaaa acttttgatg ccccagtttc aagacaacaa     360
attcacgatg taatagacca acaaatccct tcagataatt tgttttgtgc cttgagaata     420
gacggtaact tcagacatgc tcacaccaga actgttccaa gacaaactcc accttataga     480
gccatgacag atgtattgga tgaccaacct gtttttagat caatcaaag agaaggtgtt      540
ttagtcggtt ttagaacccc acaacacatg caaggtatca acgtagcagg ttatcatgaa     600
cacttcatta ctgatgacag acaaggtggt ggtcatttgt tagattacca attggaatcc     660
ggtgttttga cattcggtga aatccacaag ttgatgattg atttgccagc cgacagtgct     720
ttcttacaag ccaacttaca cccatcaaac ttagacgccg caatcagatc agtagaaaac     780
taa                                                                    783
```

<210> SEQ ID NO 10
<211> LENGTH: 260
<212> TYPE: PRT
<213> ORGANISM: Enterobacter aerogenes
<220> FEATURE:
<221> NAME/KEY: SOURCE
<222> LOCATION: 1..260
<223> OTHER INFORMATION: /mol_type="protein"
/organism="Enterobacter aerogenes"

<400> SEQUENCE: 10

```
Met Met Met His Ser Ser Ala Cys Asp Cys Glu Ala Ser Leu Cys Glu
1               5                   10                  15

Thr Leu Arg Gly Phe Ser Ala Lys His Pro Asp Ser Val Ile Tyr Gln
            20                  25                  30

Thr Ser Leu Met Ser Ala Leu Leu Ser Gly Val Tyr Glu Gly Asp Thr
        35                  40                  45

Thr Ile Ala Asp Leu Leu Ala His Gly Asp Phe Gly Leu Gly Thr Phe
    50                  55                  60

Asn Glu Leu Asp Gly Glu Met Ile Ala Phe Ser Ser Gln Val Tyr Gln
65                  70                  75                  80

Leu Arg Ala Asp Gly Ser Ala Arg Ala Ala Lys Pro Glu Gln Lys Thr
                85                  90                  95

Pro Phe Ala Val Met Thr Trp Phe Gln Pro Gln Tyr Arg Lys Thr Phe
            100                 105                 110

Asp Ala Pro Val Ser Arg Gln Gln Ile His Asp Val Ile Asp Gln Gln
        115                 120                 125

Ile Pro Ser Asp Asn Leu Phe Cys Ala Leu Arg Ile Asp Gly Asn Phe
    130                 135                 140

Arg His Ala His Thr Arg Thr Val Pro Arg Gln Thr Pro Pro Tyr Arg
145                 150                 155                 160

Ala Met Thr Asp Val Leu Asp Asp Gln Pro Val Phe Arg Phe Asn Gln
                165                 170                 175
```

```
Arg Glu Gly Val Leu Val Gly Phe Arg Thr Pro Gln His Met Gln Gly
            180                 185                 190

Ile Asn Val Ala Gly Tyr His Glu His Phe Ile Thr Asp Asp Arg Gln
        195                 200                 205

Gly Gly Gly His Leu Leu Asp Tyr Gln Leu Glu Ser Gly Val Leu Thr
    210                 215                 220

Phe Gly Glu Ile His Lys Leu Met Ile Asp Leu Pro Ala Asp Ser Ala
225                 230                 235                 240

Phe Leu Gln Ala Asn Leu His Pro Ser Asn Leu Asp Ala Ala Ile Arg
                245                 250                 255

Ser Val Glu Asn
            260

<210> SEQ ID NO 11
<211> LENGTH: 666
<212> TYPE: DNA
<213> ORGANISM: Lactococcus lactis
<220> FEATURE:
<221> NAME/KEY: source
<222> LOCATION: 1..666
<223> OTHER INFORMATION: /mol_type="DNA"
      /organism="Lactococcus lactis"

<400> SEQUENCE: 11
atgtcatcga gaatctttca acacaatacc ttcacaactt tgagtagcgg attttacaaa      60
ggcacaatca cgttgaaaga agccttagaa cacggatcag ttggcatagg tacattagat     120
actgcaaatg gtgaagttac catcatcaac ggtatagcct atcatggaga ttcggaaaac     180
catgtgagat tggtggaaga ggatgaaacg atgccttatg tcgctatggt tgaacatcaa     240
cccattgcaa agttcactga ttcctctgtg tcaaatagcg aagatttcct atccgcttta     300
accaaaaggt ttccaaccgt taatactgcc tacacaattg tcatgactgg tcagtttaag     360
gaagtaactg tctcttctaa accagcgaac aatactagac catatgacga ataatggct     420 gatcaaccgt actttacaaa ggagaacatt agtggtacaa tggttggtgt atgggctcct     480
aaacatctta ctgatctatt tgggttaggc tttcaccttc acttcgtttc tgacgataag     540
acgtttactg cacatgtaca gaatttcatt acagagaatc tggaaattga gatagggaaa     600
attaccaaga ttgaccaaga atttcctgat gatgacgaga acttcgacca acatttgttc     660
caataa                                                                666

<210> SEQ ID NO 12
<211> LENGTH: 221
<212> TYPE: PRT
<213> ORGANISM: Lactococcus lactis
<220> FEATURE:
<221> NAME/KEY: SOURCE
<222> LOCATION: 1..221
<223> OTHER INFORMATION: /mol_type="protein"
      /organism="Lactococcus lactis"

<400> SEQUENCE: 12

Met Ser Ser Arg Ile Phe Gln His Asn Thr Phe Thr Thr Leu Ser Ser
1               5                   10                  15

Gly Phe Tyr Lys Gly Thr Ile Thr Leu Lys Glu Ala Leu Glu His Gly
            20                  25                  30

Ser Val Gly Ile Gly Thr Leu Asp Thr Ala Asn Gly Glu Val Thr Ile
        35                  40                  45

Ile Asn Gly Ile Ala Tyr His Gly Asp Ser Glu Asn His Val Arg Leu
    50                  55                  60
```

Val Glu Glu Asp Glu Thr Met Pro Tyr Val Ala Met Val Glu His Gln
65                  70                  75                  80

Pro Ile Ala Lys Phe Thr Asp Ser Ser Val Ser Asn Ser Glu Asp Phe
                85                  90                  95

Leu Ser Ala Leu Thr Lys Arg Phe Pro Thr Val Asn Thr Ala Tyr Thr
            100                 105                 110

Ile Val Met Thr Gly Gln Phe Lys Glu Val Thr Val Ser Ser Lys Pro
        115                 120                 125

Ala Asn Asn Thr Arg Pro Tyr Asp Glu Ile Met Ala Asp Gln Pro Tyr
    130                 135                 140

Phe Thr Lys Glu Asn Ile Ser Gly Thr Met Val Gly Val Trp Ala Pro
145                 150                 155                 160

Lys His Leu Thr Asp Leu Phe Gly Leu Gly Phe His Leu His Phe Val
                165                 170                 175

Ser Asp Asp Lys Thr Phe Thr Ala His Val Gln Asn Phe Ile Thr Glu
            180                 185                 190

Asn Leu Glu Ile Glu Ile Gly Lys Ile Thr Lys Ile Asp Gln Glu Phe
        195                 200                 205

Pro Asp Asp Asp Glu Asn Phe Asp Gln His Leu Phe Gln
    210                 215                 220

<210> SEQ ID NO 13
<211> LENGTH: 771
<212> TYPE: DNA
<213> ORGANISM: Enterobacter aerogenes
<220> FEATURE:
<221> NAME/KEY: source
<222> LOCATION: 1..771
<223> OTHER INFORMATION: /mol_type="DNA"
      /organism="Enterobacter aerogenes"

<400> SEQUENCE: 13
atgggcaaag tagcgttagt gacaggtgct ggtcaaggca ttggaaaggc cattgccttg     60
agattggtta agatggcctt gcggtcgct atagccgatt acaacgatgt gactgctaaa    120
gccgttgcag acgagatcaa tcaacacgga ggtagagcta tagctgtcaa agttgacgtc    180
agtgatagag aacaggtttt cgctgctgta gaacaagcac gtaaaacgtt aggcggtttt    240
aacgtcatcg tcaataatgc gggagtagca ccatcaaccc ctatagagtc cattacaccc    300
gaaatagtgg acaaagtgta caacatcaat gttaagggtg tgatttgggg tattcaagcc    360
gcagttgaag cattcaagaa agaaggtcat ggtggcaaga tcattaacgc tgttcacaa     420 gcaggacatg taggcaatcc ggaattagcg gtttactctt cgtctaagtt tgctgttaga    480
gggttaaccc agacagctgc tagagatctt gcacctcttg gtatcactgt aaacggttat    540
tgcccaggta ttgtcaaaac accaatgtgg gcagagatag ataggcaagt atctgaagct    600
gcagggaaac tctctaggata tggtactgcc gaatttgcca agaggattac gttgggtaga    660
ctatctgagc cagaagatgt tgctgcttgt gtttcctatt tggcaagtcc cgactcagac    720
tatatgactg gacagagctt gctgattgat ggtgggatgg ttttcaatta a            771

<210> SEQ ID NO 14
<211> LENGTH: 256
<212> TYPE: PRT
<213> ORGANISM: Enterobacter aerogenes
<220> FEATURE:
<221> NAME/KEY: SOURCE
<222> LOCATION: 1..256
<223> OTHER INFORMATION: /mol_type="protein"

/organism="Enterobacter aerogenes"

<400> SEQUENCE: 14

Met Gly Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Val Thr Ala Lys Ala Val Ala Asp Glu Ile Asn Gln
        35                  40                  45

His Gly Gly Arg Ala Ile Ala Val Lys Val Asp Val Ser Asp Arg Glu
    50                  55                  60

Gln Val Phe Ala Ala Val Glu Gln Ala Arg Lys Thr Leu Gly Gly Phe
65                  70                  75                  80

Asn Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 15
<211> LENGTH: 1053
<212> TYPE: DNA
<213> ORGANISM: Paenibacillus polymyxa
<220> FEATURE:
<221> NAME/KEY: source
<222> LOCATION: 1..1053
<223> OTHER INFORMATION: /mol_type="DNA"
      /organism="Paenibacillus polymyxa"

<400> SEQUENCE: 15
atgtctgctt tgagatggca tggtgttaag gatttgagat tggaaaacat tgaacaacca      60
gctgctttgc caggtaaggt taagattaag gttgaatggt gtggtatttg cggttctgac     120
ttgcatgaat atgttgctgg tccaattttc attccagaaa acgctcaaca tccattgact     180
ggtgaaaaag ctccaatagt tatgggtcat gaattctccg gtcaagttgt tgaaattggt     240
gaaggtgtta ccaagatcca agttggtgat agagttgttg ttgaaccagt ttttgcttgc     300
ggtgaatgtg atgcttgtag acaaggtaaa tacaacttgt gcgataagat gggttttttg     360
ggtttggccg gtggcggtgg tggttttttct gaatacgttg cagctgatga acatatggtt     420

```
cacaagattc cagaatccgt cagttttgaa caaggtgctt tggttgaacc atctgctgtt    480
gcattatatg ccgttagaca atcccaattg aaagtcggtg ataaggctgt tgttttttggt   540 gctggtccta ttggtttgtt ggttattgaa gctttgaagg cttctggtgc ttctgaaatc   600
tatgctgttg aattgtccga agaaagaaag gctaaagctg aagaattggg tgccatagtt   660
ttagatccaa agacctatga tgtcgtcgaa gaattgcata agagaactaa tggtggtgtt   720
gatgttgctt acgaagttac tggtgttcca ccagttttga ctcaagctat tgaatccact   780
aagatctctg gtcaaatcat gatcgtcagt atcttcgaaa aagaagcccc tattaagcca   840
aacaacatcg tcatgaagga aagaaacttg actggtatca tcggttacag agatgttttc   900
ccagctgtta tctctttgat ggaaaagggt tattttccag ccgataagtt ggtcactaag   960
agaatcaaat tggaagaagt catcgaacaa ggtttcgaag gtttgttgaa agaaaagaat  1020
caagttaaga tcttggtttc cccaaaggcc taa                                1053

<210> SEQ ID NO 16
<211> LENGTH: 350
<212> TYPE: PRT
<213> ORGANISM: Paenibacillus polymyxa
<220> FEATURE:
<221> NAME/KEY: SOURCE
<222> LOCATION: 1..350
<223> OTHER INFORMATION: /mol_type="protein"
     /organism="Paenibacillus polymyxa"

<400> SEQUENCE: 16

Met Ser Ala Leu Arg Trp His Gly Val Lys Asp Leu Arg Leu Glu Asn
1               5                   10                  15

Ile Glu Gln Pro Ala Ala Leu Pro Gly Lys Val Lys Ile Lys Val Glu
            20                  25                  30

Trp Cys Gly Ile Cys Gly Ser Asp Leu His Glu Tyr Val Ala Gly Pro
        35                  40                  45

Ile Phe Ile Pro Glu Asn Ala Gln His Pro Leu Thr Gly Glu Lys Ala
    50                  55                  60

Pro Ile Val Met Gly His Glu Phe Ser Gly Gln Val Val Glu Ile Gly
65                  70                  75                  80

Glu Gly Val Thr Lys Ile Gln Val Gly Asp Arg Val Val Glu Pro
                85                  90                  95

Val Phe Ala Cys Gly Glu Cys Asp Ala Cys Arg Gln Gly Lys Tyr Asn
            100                 105                 110

Leu Cys Asp Lys Met Gly Phe Leu Gly Leu Ala Gly Gly Gly Gly
        115                 120                 125

Phe Ser Glu Tyr Val Ala Ala Asp Glu His Met Val His Lys Ile Pro
    130                 135                 140

Glu Ser Val Ser Phe Glu Gln Gly Ala Leu Val Glu Pro Ser Ala Val
145                 150                 155                 160

Ala Leu Tyr Ala Val Arg Gln Ser Gln Leu Lys Val Gly Asp Lys Ala
                165                 170                 175

Val Val Phe Gly Ala Gly Pro Ile Gly Leu Leu Val Ile Glu Ala Leu
            180                 185                 190

Lys Ala Ser Gly Ala Ser Glu Ile Tyr Ala Val Glu Leu Ser Glu Glu
        195                 200                 205

Arg Lys Ala Lys Ala Glu Glu Leu Gly Ala Ile Val Leu Asp Pro Lys
    210                 215                 220

Thr Tyr Asp Val Val Glu Glu Leu His Lys Arg Thr Asn Gly Gly Val
225                 230                 235                 240
```

Asp Val Ala Tyr Glu Val Thr Gly Val Pro Pro Val Leu Thr Gln Ala
            245                 250                 255

Ile Glu Ser Thr Lys Ile Ser Gly Gln Ile Met Ile Val Ser Ile Phe
        260                 265                 270

Glu Lys Glu Ala Pro Ile Lys Pro Asn Asn Ile Val Met Lys Glu Arg
    275                 280                 285

Asn Leu Thr Gly Ile Ile Gly Tyr Arg Asp Val Phe Pro Ala Val Ile
        290                 295                 300

Ser Leu Met Glu Lys Gly Tyr Phe Pro Ala Asp Lys Leu Val Thr Lys
305                 310                 315                 320

Arg Ile Lys Leu Glu Glu Val Ile Glu Gln Gly Phe Glu Gly Leu Leu
            325                 330                 335

Lys Glu Lys Asn Gln Val Lys Ile Leu Val Ser Pro Lys Ala
        340                 345                 350

<210> SEQ ID NO 17
<211> LENGTH: 729
<212> TYPE: DNA
<213> ORGANISM: Klebsiella oxytoca
<220> FEATURE:
<221> NAME/KEY: source
<222> LOCATION: 1..729
<223> OTHER INFORMATION: /mol_type="DNA"
      /organism="Klebsiella oxytoca"

<400> SEQUENCE: 17
atgggtaaag tcgcattggt cactggtgct ggtcaaggta tcggtaaagc tatcgcattg      60
agattggtaa aagacggttt cgctgtcgcc atcgctgatt ataatgacgc aactgcccaa     120
gctgttgcag atgaaattaa cagaagtggt ggtagagcct ggctgttaa agtcgatgta      180 tctcaaagag accaagtctt tgctgcagta gaacaagcta gaaagggttt aggtggtttc     240
gatgttatag tcaataacgc aggtgttgcc ccatcaacac ctatcgaaga atcagagaa      300 gatgttatcg acaaggtcta caacatcaac gtaaagggtg ttatatgggg tatccaagcc     360
gctgtcgaag cctttaaaca agaaggtcat ggtggtaaaa ttattaacgc ttgttctcaa     420
gcaggtcacg taggtaaccc agaattggcc gtttactctt catccaaatt cgcagttaga     480
ggtttaactc aaacagcagc cagagatttg gctcatttgg gtatcacagt caatggttat     540
tgcccaggta ttgtaaagac ccctatgtgg gcagaaatag acagacaagt ttcagaagct     600
gcaggtaaac ctttgggtta cggtactcaa gaatttgcta agagaataac tttgggtaga     660
ttatccgaac ctgaagatgt cgctgcctgt gtctcctact ggctggtac tgactcaaac     720 tgtatgtga                                                             729

<210> SEQ ID NO 18
<211> LENGTH: 242
<212> TYPE: PRT
<213> ORGANISM: Klebsiella oxytoca
<220> FEATURE:
<221> NAME/KEY: SOURCE
<222> LOCATION: 1..242
<223> OTHER INFORMATION: /mol_type="protein"
      /organism="Klebsiella oxytoca"

<400> SEQUENCE: 18

Met Gly Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Gln Ala Val Ala Asp Glu Ile Asn Arg
        35                  40                  45

Ser Gly Gly Arg Ala Leu Ala Val Lys Val Asp Val Ser Gln Arg Asp
    50                  55                  60

Gln Val Phe Ala Ala Val Glu Gln Ala Arg Lys Gly Leu Gly Gly Phe
65                  70                  75                  80

Asp Val Ile Val Asn Asn Ala Gly Val Ala Pro Ser Thr Pro Ile Glu
                85                  90                  95

Glu Ile Arg Glu Asp Val Ile Asp Lys Val Tyr Asn Ile Asn Val Lys
            100                 105                 110

Gly Val Ile Trp Gly Ile Gln Ala Ala Val Glu Ala Phe Lys Gln Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala His Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Gln Glu Phe Ala Lys Arg Ile Thr Leu Gly Arg Leu Ser Glu Pro
    210                 215                 220

Glu Asp Val Ala Ala Cys Val Ser Tyr Leu Ala Gly Thr Asp Ser Asn
225                 230                 235                 240

Cys Met

<210> SEQ ID NO 19
<211> LENGTH: 1149
<212> TYPE: DNA
<213> ORGANISM: Saccharomyces cerevisiae
<220> FEATURE:
<221> NAME/KEY: source
<222> LOCATION: 1..1149
<223> OTHER INFORMATION: /mol_type="DNA"
     /organism="Saccharomyces cerevisiae"

<400> SEQUENCE: 19
atgagagctt tggcatattt caagaagggt gatattcact tcactaatga tatccctagg      60
ccagaaatcc aaaccgacga tgaggttatt atcgacgtct cttggtgtgg gatttgtggc     120
tcggatcttc acgagtactt ggatggtcca atcttcatgc taaagatgg agagtgccat      180 aaattatcca acgctgcttt acctctggca atgggccatg agatgtcagg aattgtttcc     240
aaggttggtc taaagtgac aaaggtgaag gttggcgacc acgtggtcgt tgatgctgcc     300
agcagttgtg cggacctgca ttgctggcca cactccaaat tttacaattc aaaccatgt     360 gatgcttgtc agaggggcag tgaaaatcta tgtacccacg ccggttttgt aggactaggt     420
gtgatcagtg gtggctttgc tgaacaagtc gtagtctctc aacatcacat tatcccggtt    480
ccaaaggaaa ttcctctaga tgtggctgct ttagttgagc ctcttttctgt cacctggcat    540 gctgttaaga tttctggttt caaaaaaggc agttcagcct tggttcttgg tgcaggtccc     600
attgggttgt gtaccatttt ggtacttaag ggaatggggg ctagtaaaat tgtagtgtct    660
gaaattgcag agagaagaat agaaatggcc aagaaactgg gcgttgaggt gttcaatccc    720

```
tccaagcacg gtcataaatc tatagagata ctacgtggtt tgaccaagag ccatgatggg      780
tttgattaca gttatgattg ttctggtatt caagttactt tcgaaacctc tttgaaggca      840
ttaacattca aggggacagc caccaacatt gcagtttggg gtccaaaacc tgtcccattc      900
caaccaatgg atgtgactct ccaagagaaa gttatgactg gttcgatcgg ctatgttgtc      960
gaagacttcg aagaagttgt tcgtgccatc cacaacggag acatcgccat ggaagattgt     1020
aagcaactaa tcactggtaa gcaaaggatt gaggacggtt gggaaaaggg attccaagag     1080
ttgatggatc acaaggaatc caacgttaag attctattga cgcctaacaa tcacggtgaa     1140
atgaagtaa                                                             1149
```

<210> SEQ ID NO 20
<211> LENGTH: 381
<212> TYPE: PRT
<213> ORGANISM: Saccharomyces cerevisiae
<220> FEATURE:
<221> NAME/KEY: SOURCE
<222> LOCATION: 1..381
<223> OTHER INFORMATION: /mol_type="protein"
      /organism="Saccharomyces cerevisiae"

<400> SEQUENCE: 20

```
Arg Ala Leu Ala Tyr Phe Lys Lys Gly Asp Ile His Phe Thr Asn Asp
1               5                   10                  15

Ile Pro Arg Pro Glu Ile Gln Thr Asp Asp Glu Val Ile Ile Asp Val
            20                  25                  30

Ser Trp Cys Gly Ile Cys Gly Ser Asp Leu His Glu Tyr Leu Asp Gly
        35                  40                  45

Pro Ile Phe Met Pro Lys Asp Gly Glu Cys His Lys Leu Ser Asn Ala
    50                  55                  60

Ala Leu Pro Leu Ala Met Gly His Glu Met Ser Gly Ile Val Ser Lys
65                  70                  75                  80

Val Gly Pro Lys Val Thr Lys Val Lys Val Gly Asp His Val Val Val
            85                  90                  95

Asp Ala Ala Ser Ser Cys Ala Asp Leu His Cys Trp Pro His Ser Lys
            100                 105                 110

Phe Tyr Asn Ser Lys Pro Cys Asp Ala Cys Gln Arg Gly Ser Glu Asn
        115                 120                 125

Leu Cys Thr His Ala Gly Phe Val Gly Leu Gly Val Ile Ser Gly Gly
    130                 135                 140

Phe Ala Glu Gln Val Val Val Ser Gln His His Ile Ile Pro Val Pro
145                 150                 155                 160

Lys Glu Ile Pro Leu Asp Val Ala Ala Leu Val Glu Pro Leu Ser Val
                165                 170                 175

Thr Trp His Ala Val Lys Ile Ser Gly Phe Lys Lys Gly Ser Ser Ala
            180                 185                 190

Leu Val Leu Gly Ala Gly Pro Ile Gly Leu Cys Thr Ile Leu Val Leu
        195                 200                 205

Lys Gly Met Gly Ala Ser Lys Ile Val Val Ser Glu Ile Ala Glu Arg
    210                 215                 220

Arg Ile Glu Met Ala Lys Lys Leu Gly Val Glu Val Phe Asn Pro Ser
225                 230                 235                 240

Lys His Gly His Lys Ser Ile Glu Ile Leu Arg Gly Leu Thr Lys Ser
                245                 250                 255

His Asp Gly Phe Asp Tyr Ser Tyr Asp Cys Ser Gly Ile Gln Val Thr
            260                 265                 270
```

```
Phe Glu Thr Ser Leu Lys Ala Leu Thr Phe Lys Gly Thr Ala Thr Asn
            275                 280                 285
Ile Ala Val Trp Gly Pro Lys Pro Val Pro Phe Gln Pro Met Asp Val
            290                 295                 300
Thr Leu Gln Glu Lys Val Met Thr Gly Ser Ile Gly Tyr Val Val Glu
305                 310                 315                 320
Asp Phe Glu Glu Val Val Arg Ala Ile His Asn Gly Asp Ile Ala Met
                325                 330                 335
Glu Asp Cys Lys Gln Leu Ile Thr Gly Lys Gln Arg Ile Glu Asp Gly
            340                 345                 350
Trp Glu Lys Gly Phe Gln Glu Leu Met Asp His Lys Glu Ser Asn Val
            355                 360                 365
Lys Ile Leu Leu Thr Pro Asn Asn His Gly Glu Met Lys
            370                 375                 380
```

<210> SEQ ID NO 21
<211> LENGTH: 1341
<212> TYPE: DNA
<213> ORGANISM: Lactococcus lactis
<220> FEATURE:
<221> NAME/KEY: source
<222> LOCATION: 1..1341
<223> OTHER INFORMATION: /mol_type="DNA"
   /organism="Lactococcus lactis"

<400> SEQUENCE: 21

```
atgggtattg tcgtaatagg tactaaccat gccggaatag ctacagcaaa taccttaatc    60
gaccaatatc caggacatga aattgttatg attgacagaa actcgaatat gagttatctt   120
ggctgtggta cagcgatttg ggttgggaga caaatcgaga aacctgatga acttttctat   180
gcaaaagcag aagatttcga aaagaagggt gttaaaatcc tgaccgagac tgaagtgtca   240
gaaatcgact ttaccaacaa aatgatatat gccaaaagca agactgggga gaaaatcacg   300
gaatcttatg ataagctagt attggcaaca ggaagcagac caatcatacc caatttgcct   360
ggtaaagatc ttaaaggaat tcatttctta aagttattcc aggaaggtca agccattgac   420
gaagaattcg caaagaatga cgtgaaaaga tcgcggtaa ttggtgctgg ttatattgga   480
acagagatag ctgaagcagc taaacgtaga gggaaagaag tgttgttgtt tgatgctgaa   540
agtacctcat tagcgtcata ctacgacgaa gaatttgcca aaggcatgga tgaaaatttg   600
gcacaacacg ggattgagtt gcactttggt gaacttgccc aagagttcaa ggcaaatgaa   660
gaaggtcatg tctcccagat tgttacaaac aaatccactt atgatgtgga tctggtcatc   720
aattgcatag gatttactgc caattcagcc ttagctggtg agcatctaga aacgtttaag   780
aacggtgcca taaaggttaa taagcatcaa caatctagtg atccagacgt gtatgcagtt   840
ggtgatgttg caactatcta ctctaacgct ttgcaagact ttacttacat cgctttagct   900
agcaatgctg ttagatcagg cattgttgct ggacacaata ttggcggtaa atccatagaa   960
tctgtcggtg ttcagggtag taacggcatt tctatattcg gatacaatat gacaagtact  1020
ggtttatcag taaaagctgc taagaagatt ggtctagaag tctccttttc tgattttgaa  1080
gataagcaaa aggcttggtt tctgcatgag aacaatgatt cggtcaaaat aaggatcgta  1140
tacgaaacaa aatccaggag aataattggc gcacaattgg catcgaaatc agagattata  1200
gcgggcaaca ttaacatgtt ctctttagcc attcaggaaa agaaaacgat tgatgagtta  1260
gccctattgg atttgttctt tctgcctcac tttaactctc cgtacaatta tatgaccgta  1320
```

```
gctgcgttga atgctaaata a                                              1341
```

<210> SEQ ID NO 22
<211> LENGTH: 446
<212> TYPE: PRT
<213> ORGANISM: Lactococcus lactis
<220> FEATURE:
<221> NAME/KEY: SOURCE
<222> LOCATION: 1..446
<223> OTHER INFORMATION: /mol_type="protein"
    /organism="Lactococcus lactis"

<400> SEQUENCE: 22

Met Gly Ile Val Val Ile Gly Thr Asn His Ala Gly Ile Ala Thr Ala
1               5                   10                  15

Asn Thr Leu Ile Asp Gln Tyr Pro Gly His Glu Ile Val Met Ile Asp
            20                  25                  30

Arg Asn Ser Asn Met Ser Tyr Leu Gly Cys Gly Thr Ala Ile Trp Val
        35                  40                  45

Gly Arg Gln Ile Glu Lys Pro Asp Glu Leu Phe Tyr Ala Lys Ala Glu
    50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Asp Leu Lys Gly Ile His
        115                 120                 125

Phe Leu Lys Leu Phe Gln Glu Gly Gln Ala Ile Asp Glu Glu Phe Ala
    130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Gln Glu Phe Lys Ala Asn Glu Glu Gly His Val
    210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asn Lys His Gln Gln Ser
            260                 265                 270

Ser Asp Pro Asp Val Tyr Ala Val Gly Asp Val Ala Thr Ile Tyr Ser
        275                 280                 285

Asn Ala Leu Gln Asp Phe Thr Tyr Ile Ala Leu Ala Ser Asn Ala Val
    290                 295                 300

Arg Ser Gly Ile Val Ala Gly His Asn Ile Gly Gly Lys Ser Ile Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Lys Ile Gly Leu

```
            340             345             350
Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
    370                 375                 380

Ser Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415

Ile Asp Glu Leu Ala Leu Leu Asp Leu Phe Phe Leu Pro His Phe Asn
                420                 425                 430

Ser Pro Tyr Asn Tyr Met Thr Val Ala Ala Leu Asn Ala Lys
            435                 440                 445

<210> SEQ ID NO 23
<211> LENGTH: 1380
<212> TYPE: DNA
<213> ORGANISM: Streptococcus pneumoniae
<220> FEATURE:
<221> NAME/KEY: source
<222> LOCATION: 1..1380
<223> OTHER INFORMATION: /mol_type="DNA"
      /organism="Streptococcus pneumoniae"

<400> SEQUENCE: 23
```

| | | | | | |
|---|---|---|---|---|---|
| atgtctaaga | tagtggtagt | tggtgctaac | catgcaggaa | ctgcttgcat | caatacgatg | 60 |
| ttggataatt | tcggcaatga | aaatgagata | gtggtgtttg | atcagaattc | caacatcagc | 120 |
| tttctaggtt | gtggtatggc | gttatggatt | ggggagcaaa | tagatggtgc | tgaagggttg | 180 |
| ttttactcag | acaaagagaa | attggaagcc | aaaggtgcca | aagtctacat | gaattcgcca | 240 |
| gtcctgagta | tagactatga | caacaaagtg | gtaactgcag | aagtagaagg | caaagagcac | 300 |
| aaagaatcct | atgagaaact | gatctttgct | actggttcaa | caccgatttt | accacctatt | 360 |
| gaaggagtcg | agatcgttaa | aggtaataga | gaatttaagg | ccacacttga | aaacgtacaa | 420 |
| tttgttaagt | tgtatcagaa | tgctgaagaa | gtcatcaaca | agctttcaga | taaaagccag | 480 |
| catttagata | ggattgctgt | tgtttgaggt | ggatacattg | tgttgaatt | ggctgaagcc | 540 |
| tttgaaagac | taggaaaaga | agttgtgtta | gttgacattg | tggacactgt | cttaaacggg | 600 |
| tattatgaca | aagatttcac | ccaaatgatg | gccaagaatc | ttgaggatca | aacattaga | 660 |
| cttgctttag | ccaaacagt | gaaggctatt | gaaggcgatg | gtaaggtaga | aaggttgatt | 720 |
| acagacaagg | agtcttttcga | tgttgacatg | gtcattttag | cagtaggatt | tagaccaaac | 780 |
| actgctttgg | cagatgggaa | aattgaattg | tttagaaatg | gtgcttttct | ggtggataag | 840 |
| aaacaagaaa | cttcaatacc | cgatgtttat | gcagttggtg | attgtgcaac | agtctatgat | 900 |
| aatgccagaa | aggatacttc | ctacatagca | ttggcatcta | atgcagttag | aacgggcatt | 960 |
| gttggtgctt | ataatgcctg | tggtcatgaa | ttggagggca | ttggtgtcca | aggttctaat | 1020 |
| ggtatatcga | tttatggcct | tcatatggtt | agtaccggat | tgactctgga | gaaggccaaa | 1080 |
| gctgctggat | acaatgcgac | agaaacaggt | ttcaacgatt | tacagaagcc | agagtttatg | 1140 |
| aaacacgaca | accatgaagt | agcgatcaaa | atcgtatttg | acaaggattc | tcgtgaaatt | 1200 |
| ctaggggcac | aaatggtttc | acacgatata | gcgataagta | tgggcatcca | tatgttctct | 1260 |
| ctagcgattc | aagaacatgt | taccatagat | aaattagcat | taccgatct | attcttcttg | 1320 |
| cctcatttca | acaaacctta | caattacatc | acgatggcag | ctttgaccgc | cgaaaagtaa | 1380 |

<210> SEQ ID NO 24
<211> LENGTH: 459
<212> TYPE: PRT
<213> ORGANISM: Streptococcus pneumoniae
<220> FEATURE:
<221> NAME/KEY: SOURCE
<222> LOCATION: 1..459
<223> OTHER INFORMATION: /mol_type="protein"
    /organism="Streptococcus pneumoniae"

<400> SEQUENCE: 24

```
Met Ser Lys Ile Val Val Gly Ala Asn His Ala Gly Thr Ala Cys
1               5                  10                  15

Ile Asn Thr Met Leu Asp Asn Phe Gly Asn Glu Asn Glu Ile Val Val
            20                  25                  30

Phe Asp Gln Asn Ser Asn Ile Ser Phe Leu Gly Cys Gly Met Ala Leu
        35                  40                  45

Trp Ile Gly Glu Gln Ile Asp Gly Ala Glu Gly Leu Phe Tyr Ser Asp
    50                  55                  60

Lys Glu Lys Leu Glu Ala Lys Gly Ala Lys Val Tyr Met Asn Ser Pro
65                  70                  75                  80

Val Leu Ser Ile Asp Tyr Asp Asn Lys Val Val Thr Ala Glu Val Glu
                85                  90                  95

Gly Lys Glu His Lys Glu Ser Tyr Glu Lys Leu Ile Phe Ala Thr Gly
            100                 105                 110

Ser Thr Pro Ile Leu Pro Pro Ile Glu Gly Val Glu Ile Val Lys Gly
        115                 120                 125

Asn Arg Glu Phe Lys Ala Thr Leu Glu Asn Val Gln Phe Val Lys Leu
    130                 135                 140

Tyr Gln Asn Ala Glu Glu Val Ile Asn Lys Leu Ser Asp Lys Ser Gln
145                 150                 155                 160

His Leu Asp Arg Ile Ala Val Val Gly Gly Gly Tyr Ile Gly Val Glu
                165                 170                 175

Leu Ala Glu Ala Phe Glu Arg Leu Gly Lys Glu Val Val Leu Val Asp
            180                 185                 190

Ile Val Asp Thr Val Leu Asn Gly Tyr Tyr Asp Lys Asp Phe Thr Gln
        195                 200                 205

Met Met Ala Lys Asn Leu Glu Asp His Asn Ile Arg Leu Ala Leu Gly
    210                 215                 220

Gln Thr Val Lys Ala Ile Glu Gly Asp Gly Lys Val Glu Arg Leu Ile
225                 230                 235                 240

Thr Asp Lys Glu Ser Phe Asp Val Asp Met Val Ile Leu Ala Val Gly
                245                 250                 255

Phe Arg Pro Asn Thr Ala Leu Ala Asp Gly Lys Ile Glu Leu Phe Arg
            260                 265                 270

Asn Gly Ala Phe Leu Val Asp Lys Lys Gln Glu Thr Ser Ile Pro Asp
        275                 280                 285

Val Tyr Ala Val Gly Asp Cys Ala Thr Val Tyr Asp Asn Ala Arg Lys
    290                 295                 300

Asp Thr Ser Tyr Ile Ala Leu Ala Ser Asn Ala Val Arg Thr Gly Ile
305                 310                 315                 320

Val Gly Ala Tyr Asn Ala Cys Gly His Glu Leu Glu Gly Ile Gly Val
                325                 330                 335

Gln Gly Ser Asn Gly Ile Ser Ile Tyr Gly Leu His Met Val Ser Thr
            340                 345                 350
```

```
Gly Leu Thr Leu Glu Lys Ala Lys Ala Ala Gly Tyr Asn Ala Thr Glu
            355                 360                 365
Thr Gly Phe Asn Asp Leu Gln Lys Pro Glu Phe Met Lys His Asp Asn
        370                 375                 380
His Glu Val Ala Ile Lys Ile Val Phe Asp Lys Asp Ser Arg Glu Ile
385                 390                 395                 400
Leu Gly Ala Gln Met Val Ser His Asp Ile Ala Ile Ser Met Gly Ile
                405                 410                 415
His Met Phe Ser Leu Ala Ile Gln Glu His Val Thr Ile Asp Lys Leu
            420                 425                 430
Ala Leu Thr Asp Leu Phe Phe Leu Pro His Phe Asn Lys Pro Tyr Asn
        435                 440                 445
Tyr Ile Thr Met Ala Ala Leu Thr Ala Glu Lys
    450                 455
```

<210> SEQ ID NO 25
<211> LENGTH: 1341
<212> TYPE: DNA
<213> ORGANISM: Enterococcus faecalis
<220> FEATURE:
<221> NAME/KEY: source
<222> LOCATION: 1..1341
<223> OTHER INFORMATION: /mol_type="DNA"
       /organism="Enterococcus faecalis"

<400> SEQUENCE: 25

```
atgtctgtgg ttgtcgtagg ctgtacacat gctggtacta gtgcagtgaa atctatccta      60
gctaatcatc ccgaagctga agtcactgtt tatgaacgta tgacaacat atccttcttg     120
tcttgtggaa ttgcacttta tgttggaggt gtagttaaga atgctgccga cttatttttac   180
agcaatcctg aggaattagc cagtttagga gccactgtga aaatggaaca caacgtagaa    240
gagatcaatg tcgatgataa gacagttacg gcaaagaatc tacaaacagg tgcaacagaa    300
accgtatcct acgataagtt ggtcatgact actggaagtt ggcctataat tccaccaata    360
cccggaattg atgctgagaa cattctactt tgcaagaatt attctcaagc gaatgtcatt    420
atcgaaaagg ccaaagatgc gaaaagagtc gttgtcgttg gtggtggcta tattggtata    480
gagttagttg aagcttttgt tgaaagcggt aaacaggtga ccctagttga tggtctagac    540
aggatttttga acaagtattt tggacaaaccg tttactgatg ttttagaaaa ggagttagtt    600
gatagaggtg tgaacttagc cttaggtgaa aatgtccaac agtttgtagc tgatgaacag    660
ggaaaagttg caaagttat cactccatct caagaattcg aagcagacat ggtcataatg    720
tgtgttggct ttagaccaaa taccgaactt ttgaaagaca agttgatat gttgcctaac    780
ggtgcaattg aggttaacga gtatatgcaa acgtccaatc cagatatctt tgctgctggt    840
gattcagccg tagtgcatta caacccatcg caaacgaaga attatattcc cttagcgact    900
aatgcagtaa gacagggtat gttggtgggg agaaacttga cagaacagaa acttgcctat    960
agaggcaccc aaggtacgtc tggcttgtac ttgttcggtt ggaaaattgg ctcaacagga   1020
gtaaccaaag aatcggcaaa attgaatggg ttagatgttg aagctacagt ctttgaggat   1080
aactatagac ctgaattcat gccaacaacc gaaaaggtgc tgatggagct ggtgtacgaa   1140
aagggggactc aaaggatagt aggtgggcaa ttgatgtcca aatacgatat cactcaatca   1200
gcgaatacac tttcattggc tgtacagaac aaaatgaccg ttgaagatct ggctatttca   1260
gacttcttct ttcaaccgca ctttgaccgt ccttggaatt acttaaattt gctagcccaa   1320
gcagctctgg agaacatgta a                                             1341
```

<210> SEQ ID NO 26
<211> LENGTH: 446
<212> TYPE: PRT
<213> ORGANISM: Enterococcus faecalis
<220> FEATURE:
<221> NAME/KEY: SOURCE
<222> LOCATION: 1..446
<223> OTHER INFORMATION: /mol_type="protein"
      /organism="Enterococcus faecalis"

<400> SEQUENCE: 26

Met Ser Val Val Val Gly Cys Thr His Ala Gly Thr Ser Ala Val
1               5                   10                  15

Lys Ser Ile Leu Ala Asn His Pro Glu Ala Glu Val Thr Val Tyr Glu
            20                  25                  30

Arg Asn Asp Asn Ile Ser Phe Leu Ser Cys Gly Ile Ala Leu Tyr Val
        35                  40                  45

Gly Gly Val Val Lys Asn Ala Ala Asp Leu Phe Tyr Ser Asn Pro Glu
    50                  55                  60

Glu Leu Ala Ser Leu Gly Ala Thr Val Lys Met Glu His Asn Val Glu
65                  70                  75                  80

Glu Ile Asn Val Asp Asp Lys Thr Val Thr Ala Lys Asn Leu Gln Thr
                85                  90                  95

Gly Ala Thr Glu Thr Val Ser Tyr Asp Lys Leu Val Met Thr Thr Gly
            100                 105                 110

Ser Trp Pro Ile Ile Pro Pro Ile Pro Gly Ile Asp Ala Glu Asn Ile
        115                 120                 125

Leu Leu Cys Lys Asn Tyr Ser Gln Ala Asn Val Ile Ile Glu Lys Ala
    130                 135                 140

Lys Asp Ala Lys Arg Val Val Val Gly Gly Gly Tyr Ile Gly Ile
145                 150                 155                 160

Glu Leu Val Glu Ala Phe Val Glu Ser Gly Lys Gln Val Thr Leu Val
                165                 170                 175

Asp Gly Leu Asp Arg Ile Leu Asn Lys Tyr Leu Asp Lys Pro Phe Thr
            180                 185                 190

Asp Val Leu Glu Lys Glu Leu Val Asp Arg Gly Val Asn Leu Ala Leu
        195                 200                 205

Gly Glu Asn Val Gln Gln Phe Val Ala Asp Glu Gln Gly Lys Val Ala
    210                 215                 220

Lys Val Ile Thr Pro Ser Gln Glu Phe Glu Ala Asp Met Val Ile Met
225                 230                 235                 240

Cys Val Gly Phe Arg Pro Asn Thr Glu Leu Leu Lys Asp Lys Val Asp
                245                 250                 255

Met Leu Pro Asn Gly Ala Ile Glu Val Asn Glu Tyr Met Gln Thr Ser
            260                 265                 270

Asn Pro Asp Ile Phe Ala Ala Gly Asp Ser Ala Val Val His Tyr Asn
        275                 280                 285

Pro Ser Gln Thr Lys Asn Tyr Ile Pro Leu Ala Thr Asn Ala Val Arg
    290                 295                 300

Gln Gly Met Leu Val Gly Arg Asn Leu Thr Glu Gln Lys Leu Ala Tyr
305                 310                 315                 320

Arg Gly Thr Gln Gly Thr Ser Gly Leu Tyr Leu Phe Gly Trp Lys Ile
                325                 330                 335

Gly Ser Thr Gly Val Thr Lys Glu Ser Ala Lys Leu Asn Gly Leu Asp
            340                 345                 350

```
Val Glu Ala Thr Val Phe Glu Asp Asn Tyr Arg Pro Glu Phe Met Pro
        355                 360                 365

Thr Thr Glu Lys Val Leu Met Glu Leu Val Tyr Glu Lys Gly Thr Gln
    370                 375                 380

Arg Ile Val Gly Gly Gln Leu Met Ser Lys Tyr Asp Ile Thr Gln Ser
385                 390                 395                 400

Ala Asn Thr Leu Ser Leu Ala Val Gln Asn Lys Met Thr Val Glu Asp
                405                 410                 415

Leu Ala Ile Ser Asp Phe Phe Phe Gln Pro His Phe Asp Arg Pro Trp
            420                 425                 430

Asn Tyr Leu Asn Leu Leu Ala Gln Ala Ala Leu Glu Asn Met
                435                 440                 445

<210> SEQ ID NO 27
<211> LENGTH: 1356
<212> TYPE: DNA
<213> ORGANISM: Lactobacillus brevis
<220> FEATURE:
<221> NAME/KEY: source
<222> LOCATION: 1..1356
<223> OTHER INFORMATION: /mol_type="DNA"
      /organism="Lactobacillus brevis"

<400> SEQUENCE: 27
atgtctaagg ttaccgtggt aggttgtaca catgccggta cttttgcaat caaacagatt      60
ttggcagaac atcctgatgc agaagtaaca gtctatgaga gaaatgacgt gattagcttc     120
ttgtcgtgtg gcatagcgtt gtacttgggt gggaaagttg ctgaccctca agggcttttc     180
tactcatcac cagaagagtt acaaaagctt ggggcgaatg tccaaatgaa ccacaacgtt     240
ttagcgatag atccagatca aaagactgtt actgttgaag atctaacgag tcatgctcag     300
acaacagaat cctatgacaa gttagtcatg acttcaggtt cttggccgat agttcccaaa     360
ataccaggta ttgactccga tagagtcaag ctgtgcaaga attgggctca tgcacaagct     420
ttgattgaag atgctaaaga agcgaaaaga attactgtca ttggcgctgg ttatatcggt     480
gccgaattgg ccgaagcgta ttctactaca ggtcacgacg taacgttgat agacgcaatg     540
gatagagtaa tgcccaaata ctttgatgca gattttaccg atgtcattga gcaagattat     600
cgtgatcatg gagtgcaatt agccttgagt gaaactgttg aatcgtttac agacagtgct     660
acaggattga ccataaagac tgacaagaat agttacgaaa cagatcttgc catcttatgc     720
attggcttta gaccaaatac ggatctgctg aaaggaaaag ttgatatggc accaaatggt     780
gctattatta ccgatgacta tatgcgttcc tctaatccgg acatatttgc tgcaggagac     840
tctgctgcag ttcactataa ccctacacac cagaatgcat atatcccact agccacaaat     900
gctgtgagac aaggtatatt agtaggcaag aatttggtca aaccgaccgt aaatacatg      960 ggtacgcaaa gctcttcagg tcttgccctg tacgatagga ctattgtttc gaccggctta    1020
acgctagcag cagctaaaca acagggtgtt aatgctgaac aggtgatcgt tgaggacaat    1080
tatagacctg agtttatgcc ttcaactgaa cccgtgctaa tgagcttagt ctttgatcca    1140
gatactcata ggatcttagg aggagctttg atgtccaaat acgatgtatc ccagtctgca    1200
aacaccttgt ctgtgtgtat ccaaaacgag aatactattg atgacttagc catggttgat    1260
atgcttttcc aacctaactt cgatagacca ttcaactatc taaacatttt ggctcaagct    1320
gctcaagcca aagtagctca atcagtaaac gcctag                              1356
```

```
<210> SEQ ID NO 28
<211> LENGTH: 451
<212> TYPE: PRT
<213> ORGANISM: Lactobacillus brevis
<220> FEATURE:
<221> NAME/KEY: SOURCE
<222> LOCATION: 1..451
<223> OTHER INFORMATION: /mol_type="protein"
      /organism="Lactobacillus brevis"

<400> SEQUENCE: 28
```

| | | | | | | | | | | | | | | |
|---|---|---|---|---|---|---|---|---|---|---|---|---|---|---|
| Met | Ser | Lys | Val | Thr | Val | Val | Gly | Cys | Thr | His | Ala | Gly | Thr | Phe | Ala |
| 1 | | | | 5 | | | | | 10 | | | | | 15 | |

Ile Lys Gln Ile Leu Ala Glu His Pro Asp Ala Glu Val Thr Val Tyr
              20                  25                  30

Glu Arg Asn Asp Val Ile Ser Phe Leu Ser Cys Gly Ile Ala Leu Tyr
          35                  40                  45

Leu Gly Gly Lys Val Ala Asp Pro Gln Gly Leu Phe Tyr Ser Ser Pro
    50                  55                  60

Glu Glu Leu Gln Lys Leu Gly Ala Asn Val Gln Met Asn His Asn Val
65                  70                  75                  80

Leu Ala Ile Asp Pro Asp Gln Lys Thr Val Thr Val Glu Asp Leu Thr
                85                  90                  95

Ser His Ala Gln Thr Thr Glu Ser Tyr Asp Lys Leu Val Met Thr Ser
            100                 105                 110

Gly Ser Trp Pro Ile Val Pro Lys Ile Pro Gly Ile Asp Ser Asp Arg
        115                 120                 125

Val Lys Leu Cys Lys Asn Trp Ala His Ala Gln Ala Leu Ile Glu Asp
130                 135                 140

Ala Lys Glu Ala Lys Arg Ile Thr Val Ile Gly Ala Gly Tyr Ile Gly
145                 150                 155                 160

Ala Glu Leu Ala Glu Ala Tyr Ser Thr Thr Gly His Asp Val Thr Leu
                165                 170                 175

Ile Asp Ala Met Asp Arg Val Met Pro Lys Tyr Phe Asp Ala Asp Phe
            180                 185                 190

Thr Asp Val Ile Glu Gln Asp Tyr Arg Asp His Gly Val Gln Leu Ala
        195                 200                 205

Leu Ser Glu Thr Val Glu Ser Phe Thr Asp Ser Ala Thr Gly Leu Thr
    210                 215                 220

Ile Lys Thr Asp Lys Asn Ser Tyr Glu Thr Asp Leu Ala Ile Leu Cys
225                 230                 235                 240

Ile Gly Phe Arg Pro Asn Thr Asp Leu Leu Lys Gly Lys Val Asp Met
                245                 250                 255

Ala Pro Asn Gly Ala Ile Ile Thr Asp Asp Tyr Met Arg Ser Ser Asn
            260                 265                 270

Pro Asp Ile Phe Ala Ala Gly Asp Ser Ala Ala Val His Tyr Asn Pro
        275                 280                 285

Thr His Gln Asn Ala Tyr Ile Pro Leu Ala Thr Asn Ala Val Arg Gln
    290                 295                 300

Gly Ile Leu Val Gly Lys Asn Leu Val Lys Pro Thr Val Lys Tyr Met
305                 310                 315                 320

Gly Thr Gln Ser Ser Ser Gly Leu Ala Leu Tyr Asp Arg Thr Ile Val
                325                 330                 335

Ser Thr Gly Leu Thr Leu Ala Ala Ala Lys Gln Gln Gly Val Asn Ala
            340                 345                 350

Glu Gln Val Ile Val Glu Asp Asn Tyr Arg Pro Glu Phe Met Pro Ser

```
                355             360             365
Thr Glu Pro Val Leu Met Ser Leu Val Phe Asp Pro Asp Thr His Arg
    370             375             380

Ile Leu Gly Gly Ala Leu Met Ser Lys Tyr Asp Val Ser Gln Ser Ala
385             390             395             400

Asn Thr Leu Ser Val Cys Ile Gln Asn Glu Asn Thr Ile Asp Asp Leu
                405             410             415

Ala Met Val Asp Met Leu Phe Gln Pro Asn Phe Asp Arg Pro Phe Asn
            420             425             430

Tyr Leu Asn Ile Leu Ala Gln Ala Ala Gln Ala Lys Val Ala Gln Ser
        435             440             445

Val Asn Ala
    450
```

<210> SEQ ID NO 29
<211> LENGTH: 550
<212> TYPE: DNA
<213> ORGANISM: Artificial Sequence
<220> FEATURE:
<221> NAME/KEY: source
<222> LOCATION: 1..550
<223> OTHER INFORMATION: Synthetic "pENO2"

<400> SEQUENCE: 29

```
cgctcagcat ctgcttcttc ccaaagatga acgcggcgtt atgtcactaa cgacgtgcac    60
caacttgcgg aaagtggaat cccgttccaa aactggcatc cactaattga tacatctaca   120
caccgcacgc cttttttctg aagcccactt tcgtggactt tgccatatgc aaaattcatg   180
aagtgtgata ccaagtcagc atacacctca ctagggtagt ttctttggtt gtattgatca   240
tttggttcat cgtggttcat taattttttt tctccattgc tttctggctt tgatcttact   300
atcatttgga tttttgtcga aggttgtaga attgtatgtg acaagtggca ccaagcatat   360
ataaaaaaaa aaagcattat cttcctacca gagttgattg ttaaaaacgt atttatagca   420
aacgcaattg taattaattc ttatttgta tcttttcttc ccttgtctca atcttttatt   480
tttattttat ttttcttttc ttagtttctt tcataacacc aagcaactaa tactataaca   540
tacaataata                                                         550
```

<210> SEQ ID NO 30
<211> LENGTH: 419
<212> TYPE: DNA
<213> ORGANISM: Artificial Sequence
<220> FEATURE:
<221> NAME/KEY: source
<222> LOCATION: 1..419
<223> OTHER INFORMATION: Synthetic "pTEF2.Kl"

<400> SEQUENCE: 30

```
ctctctcgca ataacaatga acactgggtc aatcatagcc tacacaggtg aacagagtag    60
cgtttataca gggtttatac ggtgattcct acggcaaaaa ttttcattt ctaaaaaaaa   120
aaagaaaaat ttttctttcc aacgctagaa ggaaagaaa aatctaatta aattgatttg   180
gtgattttct gagagttccc tttttcatat atcgaatttt gaatataaaa ggagatcgaa   240
aaaattttc tattcaatct gttttctggt tttatttgat agttttttg tgtattatta   300
ttatggatta gtactggttt atatgggttt tctgtataa cttcttttta ttttagtttg   360
tttaatctta ttttgagtta cattatagtt ccctaactgc aagagaagta acattaaaa   419
```

<210> SEQ ID NO 31
<211> LENGTH: 598
<212> TYPE: DNA
<213> ORGANISM: Artificial Sequence
<220> FEATURE:
<221> NAME/KEY: source
<222> LOCATION: 1..598
<223> OTHER INFORMATION: Synthetic "pTEF3"

<400> SEQUENCE: 31

```
ggctgataat agcgtataaa caatgcatac tttgtacgtt caaaatacaa tgcagtagat      60
atatttatgc atattacata taatacatat cacataggaa gcaacaggcg cgttggactt     120
ttaattttcg aggaccgcga atccttacat cacacccaat cccccacaag tgatccccca     180
cacaccatag cttcaaaatg tttctactcc ttttttactc ttccagattt tctcggactc     240
cgcgcatcgc cgtaccactt caaaacaccc aagcacagca tactaaattt cccctctttc     300
ttcctctagg gtgtcgttaa ttacccgtac taaaggtttg gaaaagaaaa aagagaccgc     360
ctcgtttctt tttcttcgtc gaaaaaggca ataaaaattt ttatcacgtt tcttttttctt    420
gaaaattttt ttttttgatt ttttctctt tcgatgacct cccattgata tttaagttaa      480
taaacggtct tcaatttctc aagtttcagt ttcattttc ttgttctatt acaacttttt     540
ttacttcttg ctcattagaa agaaagcata gcaatctaat ctaagtttta attacaaa      598
```

<210> SEQ ID NO 32
<211> LENGTH: 700
<212> TYPE: DNA
<213> ORGANISM: Artificial Sequence
<220> FEATURE:
<221> NAME/KEY: source
<222> LOCATION: 1..700
<223> OTHER INFORMATION: Synthetic "pADH1"

<400> SEQUENCE: 32

```
gggtgtacaa tatggacttc ctcttttctg gcaaccaaac ccatacatcg ggattcctat      60
aataccttcg ttggtctccc taacatgtag gtggcggagg ggagatatac aatagaacag     120
ataccagaca agacataatg ggctaaacaa gactacacca attacactgc ctcattgatg     180
gtggtacata acgaactaat actgtagccc tagacttgat agccatcatc atatcgaagt     240
ttcactaccc ttttccatt tgccatctat tgaagtaata ataggcgcat gcaacttctt      300
ttcttttttt ttcttttctc tctccccgt tgttgtctca ccatatccgc aatgacaaaa      360
aaatgatgga agacactaaa ggaaaaaatt aacgacaaag acagcaccaa cagatgtcgt     420
tgttccagag ctgatgaggg gtatctcgaa gcacacgaaa ctttttcctt ccttcattca     480
cgcacactac tctctaatga gcaacggtat acggccttcc ttccagttac ttgaatttga     540
aataaaaaaa agtttgctgt cttgctatca agtataaata gacctgcaat tattaatctt     600
ttgtttcctc gtcattgttc tcgttccctt tcttccttgt ttcttttttct gcacaatatt     660
tcaagctata ccaagcatac aatcaactat ctcatataca                           700
```

<210> SEQ ID NO 33
<211> LENGTH: 549
<212> TYPE: DNA
<213> ORGANISM: Artificial Sequence
<220> FEATURE:
<221> NAME/KEY: source
<222> LOCATION: 1..549
<223> OTHER INFORMATION: Synthetic "pGPM1"

<400> SEQUENCE: 33

```
gccaaacttt tcggttaaca catgcagtga tgcacgcgcg atggtgctaa gttacatata    60
tatatatata tatatatata tatatatata gccatagtga tgtctaagta acctttatgg   120
tatatttctt aatgtggaaa gatactagcg cgcgcaccca cacacaagct tcgtcttttc   180
ttgaagaaaa gaggaagctc gctaaatggg attccacttt ccgttccctg ccagctgatg   240
gaaaaaggtt agtggaacga tgaagaataa aagagagat ccactgaggt gaaatttcag   300
ctgacagcga gtttcatgat cgtgatgaac aatggtaacg agttgtggct gttgccaggg   360
agggtggttc tcaacttta atgtatggcc aaatcgctac ttgggtttgt tatataacaa   420
agaagaaata atgaactgat tctcttcctc cttcttgtcc tttcttaatt ctgttgtaat   480
taccttcctt tgtaattttt tttgtaatta ttcttcttaa taatccaaac aaacacacat   540
attacaata                                                           549
```

<210> SEQ ID NO 34
<211> LENGTH: 650
<212> TYPE: DNA
<213> ORGANISM: Artificial Sequence
<220> FEATURE:
<221> NAME/KEY: source
<222> LOCATION: 1..650
<223> OTHER INFORMATION: Synthetic "pFBA1"

<400> SEQUENCE: 34

```
acgcaagccc taagaaatga ataacaatac tgacagtact aaataattgc ctacttggct    60
tcacatacgt tgcatacgtc gatatagata ataatgataa tgacagcagg attatcgtaa   120
tacgtaatag ttgaaaatct caaaaatgtg tgggtcatta cgtaaataat gataggaatg   180
ggattcttct attttcctt tttccattct agcagccgtc gggaaaacgt ggcatcctct   240
ctttcgggct caattggagt cacgctgccg tgagcatcct ctctttccat atctaacaac   300
tgagcacgta accaatggaa aagcatgagc ttagcgttgc tccaaaaaag tattggatgg   360
ttaataccat ttgtctgttc tcttctgact ttgactcctc aaaaaaaaaa aatctacaat   420
caacagatcg cttcaattac gccctcacaa aaacttttt ccttcttctt cgcccacgtt   480
aaattttatc cctcatgttg tctaacggat ttctgcactt gatttattat aaaaagacaa   540
agacataata cttctctatc aatttcagtt attgttcttc cttgcgttat tcttctgttc   600 ttcttttct tttgtcatat ataaccataa ccaagtaata catattcaaa               650
```

<210> SEQ ID NO 35
<211> LENGTH: 700
<212> TYPE: DNA
<213> ORGANISM: Artificial Sequence
<220> FEATURE:
<221> NAME/KEY: source
<222> LOCATION: 1..700
<223> OTHER INFORMATION: Synthetic "pPDC1"

<400> SEQUENCE: 35

```
ttatttacct atctctaaac ttcaacacct tatatcataa ctaatatttc ttgagataag    60
cacactgcac ccataccttc cttaaaaacg tagcttccag tttttggtgg ttccggcttc   120
cttcccgatt ccgcccgcta aacgcatatt tttgttgcct ggtggcattt gcaaaatgca   180
taacctatgc atttaaaaga ttatgtatgc tcttctgact tttcgtgtga tgaggctcgt   240
ggaaaaaatg aataatttat gaatttgaga acaattttgt gttgttacgg tattttacta   300
tggaataatc aatcaattga ggattttatg caaatatcgt ttgaatattt ttccgaccct   360
ttgagtactt ttcttcataa ttgcataata ttgtccgctg cccctttttc tgttagacgg   420
```

```
tgtcttgatc tacttgctat cgttcaacac caccttattt tctaactatt ttttttttag      480
ctcatttgaa tcagcttatg gtgatggcac attttttgcat aaacctagct gtcctcgttg     540
aacataggaa aaaaaatat ataaacaagg ctctttcact ctccttgcaa tcagatttgg      600
gtttgttccc tttattttca tatttcttgt catattcctt tctcaattat tattttctac    660
tcataacctc acgcaaaata acacagtcaa atcaatcaaa                            700
```

<210> SEQ ID NO 36
<211> LENGTH: 700
<212> TYPE: DNA
<213> ORGANISM: Artificial Sequence
<220> FEATURE:
<221> NAME/KEY: source
<222> LOCATION: 1..700
<223> OTHER INFORMATION: Synthetic "pPGK1"

<400> SEQUENCE: 36

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaaaaaac ccagacacgc    240
tcgacttcct gtcttcctat tgattgcagc ttccaatttc gtcacacaac aaggtcctag    300
cgacggctca caggttttgt aacaagcaat cgaaggttct ggaatggcgg gaaagggttt    360
agtaccacat gctatgatgc ccactgtgat ctccagagca agttcgttc gatcgtactg     420 ttactctctc tctttcaaac agaattgtcc gaatcgtgtg acaacaacag cctgttctca    480
cacactcttt tcttctaacc aagggggtgg tttagtttag tagaacctcg tgaaacttac    540
atttacatat atataaactt gcataaattg gtcaatgcaa gaaatacata tttggtcttt    600
tctaattcgt agtttttcaa gttcttagat gctttctttt tctcttttttt acagatcatc    660 aaggaagtaa ttatctactt tttacaacaa atataaaaca                           700
```

<210> SEQ ID NO 37
<211> LENGTH: 535
<212> TYPE: DNA
<213> ORGANISM: Artificial Sequence
<220> FEATURE:
<221> NAME/KEY: source
<222> LOCATION: 1..535
<223> OTHER INFORMATION: Synthetic "pRPLA1"

<400> SEQUENCE: 37

```
tcaagttgga tactgatctg atctctccgc cctactacca gggaccctca tgattaccgc      60
tcgaatgcga cgtttcctgc ctcataaaac tggcttgaaa atatttattc gctgaacagt    120
agcctagctt ataaaaattt catttaatta atgtaatatg aaaactcaca tgccttctgt    180
ttctaaaatt gtcacagcaa gaaataacat taccatacgt gatcttatta aactctagta    240
tcttgtctaa tacttcattt aaaagaagcc ttaaccctgt agcctcatct atgtctgcta    300
catatcgtga ggtacgaata tcgtaagatg ataccacgca actttgtaat gatttttttt    360 ttttcattt ttaaagaatg cctttacatg gtatttgaaa aaaatatctt tataagttt     420 gcgatctctt ctgttctgaa taattttttag taaagaaat caaagaata aagaaatagt    480 ccgctttgtc caatacaaca gcttaaaccg attatctcta aaataacaag aagaa          535
```

<210> SEQ ID NO 38

```
<211> LENGTH: 383
<212> TYPE: DNA
<213> ORGANISM: Artificial Sequence
<220> FEATURE:
<221> NAME/KEY: source
<222> LOCATION: 1..383
<223> OTHER INFORMATION: Synthetic "pTEF1"

<400> SEQUENCE: 38
gtttagcttg cctcgtcccc gccgggtcac ccggccagcg acatggaggc ccagaatacc    60
ctccttgaca gtcttgacgt gcgcagctca ggggcatgat gtgactgtcg cccgtacatt   120
tagcccatac atccccatgt ataatcattt gcatccatac attttgatgg ccgcacggcg   180
cgaagcaaaa attacggctc ctcgctgcag acctgcgagc agggaaacgc tcccctcaca   240
gacgcgttga attgtcccca cgccgcgccc ctgtagagaa atataaaagg ttaggatttg   300
ccactgaggt tcttctttca tatacttcct tttaaaatct tgctacgata cagttctcac   360
atcacatccg aacataaaca acc                                          383

<210> SEQ ID NO 39
<211> LENGTH: 574
<212> TYPE: DNA
<213> ORGANISM: Artificial Sequence
<220> FEATURE:
<221> NAME/KEY: source
<222> LOCATION: 1..574
<223> OTHER INFORMATION: Synthetic "pTDH3"

<400> SEQUENCE: 39
ctgctgtaac ccgtacatgc ccaaaatagg gggcgggtta cacagaatat ataacatcgt    60
aggtgtctgg gtgaacagtt tattcctggc atccactaaa tataatggag cccgcttttt   120
aagctggcat ccagaaaaaa aaagaatccc agcaccaaaa tattgttttc ttcaccaacc   180
atcagttcat aggtccattc tcttagcgca actacagaga acaggggcac aaacaggcaa   240
aaaacgggca caacctcaat ggagtgatgc aacctgcctg gagtaaatga tgacacaagg   300
caattgaccc acgcatgtat ctatctcatt ttcttacacc ttctattacc ttctgctctc   360
tctgatttgg aaaaagctga aaaaaaaggt tgaaaccagt tccctgaaat tattccccta   420
cttgactaat aagtatataa agacggtagg tattgattgt aattctgtaa atctatttct   480
taaacttctt aaattctact tttatagtta gtcttttttt tagttttaaa acaccaagaa   540
cttagtttcg aataaacaca cataaacaaa caaa                              574

<210> SEQ ID NO 40
<211> LENGTH: 300
<212> TYPE: DNA
<213> ORGANISM: Artificial Sequence
<220> FEATURE:
<221> NAME/KEY: source
<222> LOCATION: 1..300
<223> OTHER INFORMATION: Synthetic "tTHD2"

<400> SEQUENCE: 40
atttaactcc ttaagttact ttaatgattt agttttttatt attaataatt catgctcatg    60
acatctcata tacgcgttta taaaacttaa atagattgaa aatgtattaa agattcctca   120
gggattcgat ttttttggaa gttttgtttt tttttttcctt gagatgctgt agtatttggg   180
aacaattata caatcgaaag atatatgctt acattcgacc gttttagccg tgatcattat   240
cctatagtaa cataacctga agcataactg acactactat catcaatact tgtcacatga   300
```

<210> SEQ ID NO 41
<211> LENGTH: 300
<212> TYPE: DNA
<213> ORGANISM: Artificial Sequence
<220> FEATURE:
<221> NAME/KEY: source
<222> LOCATION: 1..300
<223> OTHER INFORMATION: Synthetic "tCYC1"

<400> SEQUENCE: 41

```
acaggcccct tttcctttgt cgatatcatg taattagtta tgtcacgctt acattcacgc    60
cctcctccca catccgctct aaccgaaaag gaaggagtta gacaacctga agtctaggtc   120
cctatttatt ttttttaata gttatgttag tattaagaac gttatttata tttcaaattt   180
ttcttttttt tctgtacaaa cgcgtgtacg catgtaacat tatactgaaa accttgcttg   240
agaaggtttt gggacgctcg aaggctttaa tttgcaagct tcgcagttta cactctcatc   300
```

<210> SEQ ID NO 42
<211> LENGTH: 300
<212> TYPE: DNA
<213> ORGANISM: Artificial Sequence
<220> FEATURE:
<221> NAME/KEY: source
<222> LOCATION: 1..300
<223> OTHER INFORMATION: Synthetic "tTDH3"

<400> SEQUENCE: 42

```
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt cttttttcgcc acatgtaata tctgtagtag   180
atacctgata cattgtggat gctgagtgaa attttagtta ataatggagg cgctcttaat   240
aattttgggg atattggctt ttttttttaa agtttacaaa tgaattttttt ccgccaggat   300
```

<210> SEQ ID NO 43
<211> LENGTH: 354
<212> TYPE: DNA
<213> ORGANISM: Artificial Sequence
<220> FEATURE:
<221> NAME/KEY: source
<222> LOCATION: 1..354
<223> OTHER INFORMATION: Synthetic "tADH1"

<400> SEQUENCE: 43

```
actagttcta gagcggccgc caccgcggtg gcgaattctc ttatgattta tgatttttat    60
tattaaataa gttataaaaa aaataagtgt atacaaattt taaagtgact cttaggtttt   120
aaaacgaaaa ttcttattct tgagtaactc tttcctgtag gtcaggttgc tttctcaggt   180
atagcatgag gtcgctctta ttgaccacac ctctaccggc atgccgagca aatgcctgca   240
aatcgctccc catttcaccc aattgtagat atgctaactc cagcaatgag ttgatgaatc   300
tcggtgtgta tttatgtcc tcagaggaca acacctgttg taatcgttct tcca           354
```

<210> SEQ ID NO 44
<211> LENGTH: 299
<212> TYPE: DNA
<213> ORGANISM: Artificial Sequence
<220> FEATURE:
<221> NAME/KEY: source
<222> LOCATION: 1..299
<223> OTHER INFORMATION: Synthetic "tTPI1"

<400> SEQUENCE: 44

```
gattaatata attatataaa aatattatct tcttttcttt atatctagtg ttatgtaaaa      60
taaattgatg actacggaaa gcttttttat attgtttctt tttcattctg agccacttaa     120
atttcgtgaa tgttcttgta agggacggta gatttacaag tgatacaaca aaaagcaagg     180 cgcttttct aataaaaaga agaaaagcat ttaacaattg aacacctcta tatcaacgaa      240
gaatattact ttgtctctaa atccttgtaa aatgtgtacg atctctatat gggttactc     299
```

<210> SEQ ID NO 45
<211> LENGTH: 299
<212> TYPE: DNA
<213> ORGANISM: Artificial Sequence
<220> FEATURE:
<221> NAME/KEY: source
<222> LOCATION: 1..299
<223> OTHER INFORMATION: Synthetic "tMET25"

<400> SEQUENCE: 45

```
gtgtgcgtaa tgagttgtaa aattatgtat aaacctactt tctctcacaa gtactatact      60
tttataaaac gaactttatt gaaatgaata tccttttttt cccttgttac atgtcgtgac     120
tcgtactttg aacctaaatt gttctaacat caaagaacag tgttaattcg cagtcgagaa     180
gaaaaatatg gtgaacaaga ctcatctact tcatgagact actttacgcc tcctataaag     240
ctgtcacact ggataaattt attgtaggac caagttacaa aagaggatga tggaggttt      299
```

<210> SEQ ID NO 46
<211> LENGTH: 305
<212> TYPE: DNA
<213> ORGANISM: Artificial Sequence
<220> FEATURE:
<221> NAME/KEY: source
<222> LOCATION: 1..305
<223> OTHER INFORMATION: Synthetic "tENO2"

<400> SEQUENCE: 46

```
ggatcctaaa gtgcttttaa ctaagaatta ttagtctttt ctgcttattt tttcatcata      60
gtttagaaca ctttatatta acgaatagtt tatgaatcta tttaggttta aaaattgata     120 cagtttata agttactttt tcaaagactc gtgctgtcta ttgcataatg cactggaagg      180 ggaaaaaaa ggtgcacacg cgtggctttt tcttgaattt gcagtttgaa aaataactac     240
atggatgata agaaaacatg gagtacagtc actttgagaa ccttcaatca gctggtaacg     300
tcttc                                                                 305
```

<210> SEQ ID NO 47
<211> LENGTH: 300
<212> TYPE: DNA
<213> ORGANISM: Artificial Sequence
<220> FEATURE:
<221> NAME/KEY: source
<222> LOCATION: 1..300
<223> OTHER INFORMATION: Synthetic "tMET3"

<400> SEQUENCE: 47

```
tcgtcataaa atgctcccat ctcaaaagta gggcaaaatt catgatcgac cgcgcaaaat      60
aaatagattt gcaaataagt tttgtatgta catttattaa tatatataat atatcaaaag     120
aaaaaaatca aaaaaaaaaa aaaaaaaaa ttgcactctt attcagtcat caattacaaa     180
acctagagat agcgatggtg catattcaat aaaaaactcc ttatactgtc gagaaagctt     240
attattggta cttctcgaag atactaaaaa aggttaattt ttggagacgg aggcaatagc     300
```

<210> SEQ ID NO 48
<211> LENGTH: 301
<212> TYPE: DNA
<213> ORGANISM: Artificial Sequence
<220> FEATURE:
<221> NAME/KEY: source
<222> LOCATION: 1..301
<223> OTHER INFORMATION: Synthetic "tPGK1"

<400> SEQUENCE: 48
attgaattga attgaaatcg atagatcaat ttttttcttt tctctttccc catcctttac    60
gctaaaataa tagtttattt tattttttga atatttttta tttatatacg tatatataga   120
ctattattta tcttttaatg attattaaga ttttttattaa aaaaaaattc gctcctcttt   180
taatgccttt atgcagtttt ttttttcccat tcgatatttc tatgttcggg ttcagcgtat   240
tttaagttta ataactcgaa aattctgcgt tcgttaaagc tttcgagaag gatattattt   300
a                                                                   301

<210> SEQ ID NO 49
<211> LENGTH: 700
<212> TYPE: DNA
<213> ORGANISM: Artificial Sequence
<220> FEATURE:
<221> NAME/KEY: source
<222> LOCATION: 1..700
<223> OTHER INFORMATION: Synthetic "pPYK1"

<400> SEQUENCE: 49
aaaaggaaag attattgaaa gagaaagaaa gaaaaaaaaa aaatgtacac ccagacatcg    60
ggcttccaca atttcggctc tattgttttc catctctcgc aacggcggga ttcctctatg   120
gcgtgtgatg tctgtatctg ttacttaatc cagaaactgg cacttgaccc aactctgcca   180
cgtgggtcgt tttgccatcg acagattggg agattttcat agtagaattc agcatgatag   240
ctacgtaaat gtgttccgca ccgtcacaaa gtgttttcta ctgttctttc ttctttcgtt   300
cattcagttg agttgagtga gtgctttgtt caatggatct tagctaaaat gcatattttt   360
tctcttggta aatgaatgct tgtgatgtct tccaagtgat ttcctttcct tcccatatga   420
tgctaggtac ctttagtgtc ttcctaaaaa aaaaaaaagg ctcgccatca aaacgatatt   480
cgttggcttt ttttttctgaa ttataaatac tctttggtaa cttttcattt ccaagaacct   540
cttttttcca gttatatcat ggtcccctt caaagttatt ctctactctt tttcatattc   600 attcttttc atcctttggt tttttattct taacttgttt attattctct cttgtttcta   660
tttacaagac accaatcaaa acaaataaaa catcatcaca                         700

<210> SEQ ID NO 50
<211> LENGTH: 500
<212> TYPE: DNA
<213> ORGANISM: Artificial Sequence
<220> FEATURE:
<221> NAME/KEY: source
<222> LOCATION: 1..500
<223> OTHER INFORMATION: Synthetic "pTPI1"

<400> SEQUENCE: 50
atttaaactg tgaggacctt aatacattca gacacttctg cggtatcacc ctacttattc    60
ccttcgagat tatatctagg aacccatcag gttggtggaa gattacccgt tctaagactt   120
ttcagcttcc tctattgatg ttacacctgg acaccccttt tctggcatcc agttttttaat  180 cttcagtggc atgtgagatt ctccgaaatt aattaaagca atcacacaat tctctcggat   240

```
accacctcgg ttgaaactga caggtggttt gttacgcatg ctaatgcaaa ggagcctata    300
tacctttggc tcggctgctg taacagggaa tataaagggc agcataattt aggagtttag    360
tgaacttgca acatttacta tttttccttc ttacgtaaat attttctttt ttaattctaa    420
atcaatcttt ttcaattttt tgtttgtatt cttttcttgc ttaaatctat aactacaaaa    480
aacacataca taaactaaaa                                                500

<210> SEQ ID NO 51
<211> LENGTH: 300
<212> TYPE: DNA
<213> ORGANISM: Artificial sequences
<220> FEATURE:
<221> NAME/KEY: source
<222> LOCATION: 1..300
<223> OTHER INFORMATION: Synthetic "tDIT1"

<400> SEQUENCE: 51
taaagtaaga gcgctacatt ggtctacctt tttgttcttt tacttaaaca ttagttagtt     60
cgttttcttt ttctcatttt tttatgtttc cccccaaag ttctgatttt ataatatttt    120
atttcacaca attccattta acagaggggg aatagattct ttagcttaga aaattagtga   180
tcaatatata tttgcctttc ttttcatctt ttcagtgata ttaatggttt cgagacactg   240
caatggccct agttgtctaa gaggatagat gttactgtca aagatgatat tttgaatttc   300

<210> SEQ ID NO 52
<211> LENGTH: 33
<212> TYPE: DNA
<213> ORGANISM: Artificial sequences
<220> FEATURE:
<221> NAME/KEY: source
<222> LOCATION: 1..33
<223> OTHER INFORMATION: Synthetic "loxP"

<400> SEQUENCE: 52
ataacttcgt ataatgtatg ctatacgaag tta                                  33

<210> SEQ ID NO 53
<211> LENGTH: 2085
<212> TYPE: DNA
<213> ORGANISM: Saccharomyces
<220> FEATURE:
<221> NAME/KEY: source
<222> LOCATION: 1..2085
<223> OTHER INFORMATION: /mol_type="DNA"
      /note="HAA-1 gene"
      /organism="Saccharomyces"

<400> SEQUENCE: 53
atggtcttga taaatggcat aaagtatgcc tgtgagaggt gcataagagg ccatagagta     60
acaacatgca atcatacaga tcaaccgctt atgatgatca aacccaaagg tagaccttcc   120
actacatgcg actattgtaa acaacttcga aaaacaaga atgcaaatcc tgaaggtgtt   180
tgcacgtgtg gccggctaga aagaaaaaa ctggcacaga aagccaaaga agaagcaaga   240
gctaaagcca agaaaaaaca agaaaacag tgtacctgcg ggactgatga ggtttgcaaa   300
tatcatgctc aaaagagaca tctaagaaag tccccttcaa gttctcaaaa gaaggaaga   360 tccatttctc gttctcaacc aatgtttgaa agggtattgt cttctacttc acttgacagc   420
aatatgttat ccggccacgg agcactatca gatacctcta gcatactgac gagcacattt   480
ttagacagtg agccgggtgt tggtaaaatt tcaaaagatt accatcatgt cccttcattg   540
gcctccattt catccttaca atcctcgcaa tcgttagatc aaaatttcag tataccacaa   600
```

```
agcccgccgt tatcttcaat gtcatttaat tttctcacgg gaaatatcaa tgaaaccaac    660
caaaatcaca gtaatcatca gcattcaaaa tcaggcaata actggcaaga tagttcggta    720
agcttgccag cgaaagctga ttcacgtctt aacatgatgg ataaaaacaa ctctgtgggt    780
cttgacctat taggccattc aaaacgaata tcgccgatat caaactctcg tgtgggcgaa    840
gttagcgttc cgctagaaga atatattcct tctgacattg atggggttgg aagagttact    900
gataaaagct ctttggtcta cgattggcca tttgatgaaa gtattgagag aaatttcagt    960
acaaccgcaa ccgctgcaac tggtgaaagt aagttcgaca ttaacgacaa ctgtaataga   1020
attaatagca aaagttatag taagactaat agtatgaatg gaaacggtat gaacaatagc   1080
aataataata atatcaacag taatggcaac gacaagaaca ataacaactc ttctagacaa   1140
gaacatcaag gaaatggact atttgacatg tttacagatt catcgtcgat ttcaacgctt   1200
tcccgtgcaa acttattatt gcaagaaaaa attggttcgc aagaaaactc tgtcaaacaa   1260
gaaaactatt cgaaaaatcc tcaacttcgt catcaattaa cttccagaag tagatcattt   1320
attcatcatc cggcaaacga gtatttgaag aatacttttg gaaattcaca tagtaatgac   1380
atcggaaagg gagttgaagt gctatctttg acaccgagtt ttatggatat tcccgaaaaa   1440
gaaagagaaa cggaaagatc gccatcatcc aattacatta ctgacagacc tttcactcga   1500
aaacctagat cttctagcat tgacgtaaac cataggtatc cacctatggc accaacaacc   1560
gtagcgacat ctcccggtgc attgaacaat gccgtagcaa gcaatctcga cgatcaactg   1620
agtttaacat cactaaactc tcagccatca tcgatagcaa atatgatgat ggacccttca   1680
aacctagctg agcaaagttc tattcattca gttcctcagt caataaactc tccgagaatg   1740
cctaaaactg gaagtcgcca agacaagaac attcacacta agaaggaaga agaaatccg    1800 ctaaataaca tacgcgatct gtcacaattg gaaaatgtac cagacgagat gaaccaaatg   1860
ttctccccac cattaaaaag tatgaataga ccggatgcca aagggaaaa ttcatctagt   1920 agtaatttca taatccaagg aaatagcatg atctctacgc cttccggaag gaatgacctt   1980
ccagatacct ctccaatgag tagtattcaa acagcgtcac caccaagtca attactgacc   2040
gatcaaggat ttgcggattt ggataatttc atgtcttcgt tatga                  2085
```

<210> SEQ ID NO 54
<211> LENGTH: 694
<212> TYPE: PRT
<213> ORGANISM: Saccharomyces
<220> FEATURE:
<221> NAME/KEY: SOURCE
<222> LOCATION: 1..694
<223> OTHER INFORMATION: /mol_type="protein"
      /note="HAA-1 protein"
      /organism="Saccharomyces"

<400> SEQUENCE: 54

```
Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
                20                  25                  30

Ile Lys Pro Lys Gly Arg Pro Ser Thr Thr Cys Asp Tyr Cys Lys Gln
            35                  40                  45

Leu Arg Lys Asn Lys Asn Ala Asn Pro Glu Gly Val Cys Thr Cys Gly
        50                  55                  60

Arg Leu Glu Lys Lys Lys Leu Ala Gln Lys Ala Lys Glu Glu Ala Arg
65                  70                  75                  80
```

-continued

Ala Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
        130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
                180                 185                 190

Asp Gln Asn Phe Ser Ile Pro Gln Ser Pro Pro Leu Ser Ser Met Ser
            195                 200                 205

Phe Asn Phe Leu Thr Gly Asn Ile Asn Glu Thr Asn Gln Asn His Ser
        210                 215                 220

Asn His Gln His Ser Lys Ser Gly Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Asn Ser Asn Asn Asn Ile Asn Ser Asn
            355                 360                 365

Gly Asn Asp Lys Asn Asn Asn Ser Ser Arg Gln Glu His Gln Gly
        370                 375                 380

Asn Gly Leu Phe Asp Met Phe Thr Asp Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Gln Glu Asn Tyr Ser Lys Asn Pro Gln Leu Arg His Gln
                420                 425                 430

Leu Thr Ser Arg Ser Arg Ser Phe Ile His His Pro Ala Asn Glu Tyr
            435                 440                 445

Leu Lys Asn Thr Phe Gly Asn Ser His Ser Asn Asp Ile Gly Lys Gly
        450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
                485                 490                 495

```
Pro Phe Thr Arg Lys Pro Arg Ser Ser Ser Ile Asp Val Asn His Arg
            500                 505                 510

Tyr Pro Pro Met Ala Pro Thr Val Ala Thr Ser Pro Gly Ala Leu
            515                 520                 525

Asn Asn Ala Val Ala Ser Asn Leu Asp Asp Gln Leu Ser Leu Thr Ser
        530                 535                 540

Leu Asn Ser Gln Pro Ser Ser Ile Ala Asn Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
        675                 680                 685

Asn Phe Met Ser Ser Leu
    690

<210> SEQ ID NO 55
<211> LENGTH: 1089
<212> TYPE: DNA
<213> ORGANISM: Kluyveromyces lactis
<220> FEATURE:
<221> NAME/KEY: source
<222> LOCATION: 1..1089
<223> OTHER INFORMATION: /mol_type="DNA"
      /note="LEU2.Kl"
      /organism="Kluyveromyces lactis"

<400> SEQUENCE: 55
atgtctaaga atatcgttgt cctaccgggt gatcacgtcg gtaaagaagt tactgacgaa      60
gctattaagg tcttgaatgc cattgctgaa gtccgtccag aaattaagtt caatttccaa     120
catcacttga tcgggggtgc tgccatcgat gccactggca ctcctttacc agatgaagct     180
ctagaagcct ctaagaaagc cgatgctgtc ttactaggtg ctgttggtgg tccaaaatgg     240
ggtacgggcg cagttagacc agaacaaggt ctattgaaga tcagaaagga attgggtcta     300
tacgccaact tgagaccatg taactttgct tctgattctt actagatct ttctcctttg     360 aagcctgaat atgcaaaggg taccgatttc gtcgtcgtta gagaattggt tggtggtatc     420
tactttggtg aaagaaaaga agatgaaggt gacggagttg cttgggactc tgagaaatac     480
agtgttcctg aagttcaaag aattacaaga atggctgctt tcttggcatt gcaacaaaac     540
ccaccattac caatctggtc tcttgacaag gctaacgtgc ttgcctcttc cagattgtgg     600
agaaagactg ttgaagaaac catcaagact gagttcccac aattaactgt tcagcaccaa     660
ttgatcgact ctgctgctat gattttggtt aaatcaccaa ctaagctaaa cggtgttgtt     720
attaccaaca acatgtttgg tgatattatc tccgatgaag cctctgttat tccaggttct     780
```

-continued

```
ttgggtttat taccttctgc atctctagct tccctacctg acactaacaa ggcattcggt    840
ttgtacgaac catgtcatgg ttctgcccca gatttaccag caaacaaggt taacccaatt    900
gctaccatct tatctgcagc tatgatgttg aagttatcct tggatttggt tgaagaaggt    960
agggctcttg aagaagctgt tagaaatgtc ttggatgcag gtgtcagaac cggtgaccct   1020
ggtggttcta actctaccac tgaggttggc gatgctatcg ccaaggctgt caaggaaatc   1080
ttggcttaa                                                           1089
```

<210> SEQ ID NO 56
<211> LENGTH: 362
<212> TYPE: PRT
<213> ORGANISM: Kluyveromyces lactis
<220> FEATURE:
<221> NAME/KEY: SOURCE
<222> LOCATION: 1..362
<223> OTHER INFORMATION: /mol_type="protein"
     /note="LEU2.Kl"
     /organism="Kluyveromyces lactis"

<400> SEQUENCE: 56

```
Met Ser Lys Asn Ile Val Val Leu Pro Gly Asp His Val Gly Lys Glu
1               5                   10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270

Pro Asp Thr Asn Lys Ala Phe Gly Leu Tyr Glu Pro Cys His Gly Ser
        275                 280                 285
```

-continued

```
Ala Pro Asp Leu Pro Ala Asn Lys Val Asn Pro Ile Ala Thr Ile Leu
    290                 295                 300

Ser Ala Ala Met Met Leu Lys Leu Ser Leu Asp Leu Val Glu Glu Gly
305                 310                 315                 320

Arg Ala Leu Glu Glu Ala Val Arg Asn Val Leu Asp Ala Gly Val Arg
                325                 330                 335

Thr Gly Asp Leu Gly Gly Ser Asn Ser Thr Thr Glu Val Gly Asp Ala
            340                 345                 350

Ile Ala Lys Ala Val Lys Glu Ile Leu Ala
        355                 360
```

MICROORGANISM STRAINS FOR THE PRODUCTION OF 2.3-BUTANEDIOL

FIELD OF THE INVENTION

The present invention relates to microorganism having an improved 2,3-butanediol pathway. The recombinant microorganism is modified to improve the production of 2,3-butanediol compared to the unmodified microorganism. The invention also provides methods for using such microorganism to produce 2,3-butanediol.

BACKGROUND OF THE INVENTION 2,3-Butanediol (2,3-BDO) is a multi-functional platform chemical that can be used to produce other bulk chemicals and synthesize diverse products, such as drugs, cosmetics, and industrial solvents (Celinska and Grajek, 2009; Syu, 2001).

More particularly, 2,3-BDO may be used in considerable industrial applications on important markets, as herein after summarized.

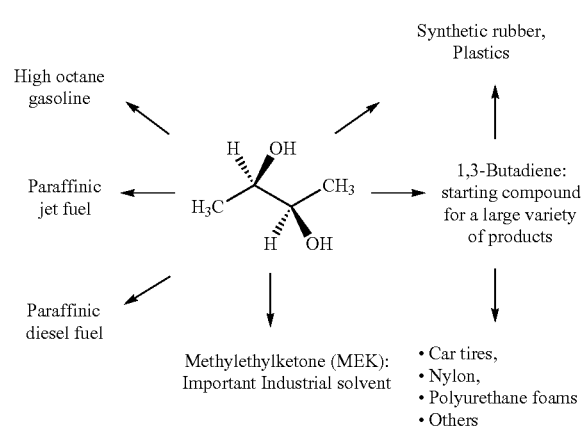

Two of the most interesting 2,3-BDO applications are the Methyl Ethyl Ketone (MEK solvent) and the butadiene (BDE), a major monomer in the manufacture of synthetic rubber and tires.

The traditional chemical synthesis of 2,3-BDO is faced the drawback of the petroleum deficiency and environmental pollution, whereas the manufacturing of 2,3-BDO is currently still growing by an annual rate of 4-7% (Jiayang et al., 2006).

Many chemicals that could only be produced by traditional chemical processes in the past can now have the potential to be generated biologically, using renewable resources (Danner & Braun, 1999; Hatti-Kaul et al., 2007). Microbial production of 2,3-BDO is one such example. Interest in this bioprocess has increased remarkably because 2,3-BDO has a large number of industrial applications, as above-mentioned, and microbial production will alleviate the dependence on oil supply for the production of platform chemicals (Celmska & Grajek, 2009; Wu et al., 2008). Saccharomyces cerevisiae is an especially well suited platform for such bioprocesses (Nielsen et al., 2013).

However, at the time being, the 2,3-BDO produced by microbial processes is a compound rarely used on an industrial scale, due to its high production costs notably linked to poor production yield. The chemical industry uses indeed preferentially other C4 chemicals compounds, such as 1,4-BDO and succinic acid.

Regarding the microbial production of 2,3-BDO, most studies used bacteria, such as *Klebsiella pneumonia, Klebsiella oxytoca, Enterobacter aerogenes*, and *Paenibacillus polymyxa* to produce 2,3-BDO (Cho et al., 2012; Han et al., 2013; Hassler et al., 2012; Jung et al., 2012). While these bacteria are capable of producing 2,3-BDO with high yields and productivities, they are however classified as pathogenic bacteria so that large-scale fermentation might be difficult in terms of safety and industrialization (Celinska and Grajek, 2009).

2,3-BDO production by a GRAS (i.e. generally recognized as safe) microorganism would thus be desirable. Yeast, and more particularly *Saccharomyces cerevisiae*, is an appropriate microorganism in this context. *S. cerevisiae* is known to produce 2,3-BDO naturally, but the yield and productivity of 2,3-BDO production are poor. Ethanol production is indeed the most obvious barrier for the efficient 2,3-BDO production in *S. cerevisiae* because pyruvate, a key intermediate, is preferentially used for producing ethanol rather than 2,3-BDO.

In order to minimize ethanol production and maximize 2,3-BDO production, a pyruvate decarboxylase (Pdc)-deficient mutant has been utilized for 2,3-BDO production. However, Pdc-deficient strains have potential defects for industrial fermentations (Flikweert et al., FEMS Microbiology Letters 174, 1999 73-79).

WO 2013/076144, WO 2011/040901 and US 2011/0124060 discloses non-naturally occurring microorganism having an improved 2,3-BDO pathway. Ethanol and acetate production pathways being disrupted, US 2011/0124060 and WO 2013/076144 describe that it leads to an unbalanced redox state to which the proposed solution consists to increase the activity of a NADH-dependent enzyme and, possibly, the pool of NAD+.

In Soo-Jung Kim et al. (Bioresource Technology 146 (2013) 274-281) was constructed Pdc-deficient strain and evolved for growing on glucose. The evolved Pdc-deficient strain was genotyped to identify necessary genetic changes which enable the Pdc-deficient strain to grow on high glucose concentration. However, these strains grow slowly has compared to strains that have retain some pdc activity. Subsequently, the 2,3-BDO biosynthetic pathway from *Bacillus subtilis* was introduced into the evolved Pdc-deficient strain to produce 2,3-BDO from glucose efficiently in *S. cerevisiae*. This strain is displayed as producing 96.2 g/L after 244 h cultivation, with a 2,3-BDO yield (0.28 g 2,3-BDO/g glucose) and volumetric productivity (0.39 g 2,3-BDO/Lh$^{-1}$). However, this 2,3-BDO yield appears not appropriate to be economically viable on an industrial point of view.

Therefore, for obvious reasons, to improve the production of 2,3-BDO through microbial processes, and more particularly of the conversion of pyruvate to 2,3-BDO, remains a constant aim. More particularly, there is still a need in a stable recombinant microorganism having an enhanced production yield of 2,3-butanediol, in particular compatible with industrialization requirements.

SUMMARY OF THE INVENTION

The present invention relates to a recombinant yeast having a reduced pyruvate decarboxylase activity, in the genome of which has been inserted:

one or more nucleic acids encoding an acetolactate synthase or ALS,
one or more nucleic acids encoding an acetolactate decarboxylase or ALD,
one or more nucleic acids encoding a butanediol dehydrogenase or BDH, and
one or more copies of a nucleic acids encoding a NADH oxidase or NOXE.

According to a particular embodiment, the recombinant yeast according to the present invention may comprise one or more DNA constructs selected in a group comprising the following formulae:

$$5'\text{-[Gene 1]}_{x1}\text{-3' and } 5'\text{-[Gene 2]}_{x2}\text{-3' and } 5'\text{-[Gene 3]}_{x3}\text{-3' and } 5'\text{-[Gene 4]}_{x4}\text{-3'}, \quad (I)$$

$$5'\text{-[Gene 1]}_{x1}\text{-[Gene 2]}_{x2}\text{-[Gene 3]}_{x3}\text{-3' and } 5'\text{-[Gene 4]}_{x4}\text{-3'}, \quad (II)$$

$$5'\text{-[Gene 1]}_{x1}\text{-[Gene 2]}_{x2}\text{-3' and } 5'\text{-[Gene 3]}_{x3}\text{-[Gene 4]}_{x4}\text{-3'}, \quad (III)$$

$$5'\text{-[Gene 1]}_{x1}\text{-[Gene 2]}_{x2}\text{-[Gene 3]}_{x3}\text{-[Gene 4]}_{x4}\text{-3'}, \text{ and} \quad (IV)$$

a combination thereof,
wherein:
"Gene 1" means a nucleic acid selected from a group comprising ALS, ALD, BDH or NOXE;
"Gene 2" means a nucleic acid selected from a group comprising ALS, ALD, BDH or NOXE but different from gene 1;
"Gene 3" means a nucleic acid selected from a group comprising ALS, ALD, BDH or NOXE but different from genes 1 and 2;
"Gene 4" means a nucleic acid selected from a group comprising ALS, ALD, BDH or NOXE but different from genes 1 to 3;
"ALS" is a nucleic acid encoding an acetolactate synthase;
"ALD" is a nucleic acid encoding an acetolactate decarboxylase;
"BDH" is a nucleic acid encoding a butanediol dehydrogenase;
"NOXE" is a nucleic acid encoding a NADH oxidase;
each of "x1", "x2", "x3" and "x4", one independently from the others, represents an integer ranging from 0 to 50, preferably from 0 to 20, most preferably one, and provided that said recombinant yeast comprises at least one nucleic acid encoding for each of ALS, ALD, BDH and NOXE.

Preferably, each among "x1", "x2", "x3" and "x4", independently the ones of the others, represents an integer ranging from 0 to 10, more particularly ranging from 0 to 5, in particular ranging from 0 to 3, and still better represents an integer equal to 1.

According to another particular embodiment, the recombinant yeast according to the invention may comprise at least one, preferably at least two, DNA construct(s) of above-mentioned formula (II), identical or different, wherein "Gene 4" means a nucleic acid encoding NADH oxidase.

According to yet another particular embodiment, the recombinant yeast according to the invention may comprise at least one, preferably at least two, DNA construct(s) of formula (IIa), identical or different, wherein each formula (IIa) has the following formula:

$$5'\text{-[(prom5)}_{y1}\text{-Gene 1-term5]}_{x5}\text{-[prom1-Gene 1-term1]}_{x1}\text{-[prom2-Gene 2-term2]}_{x2}\text{-[prom3-Gene 3-(term3)}_{z1}]_{x3}\text{-3' and } 5'\text{-[(prom4)}_{y2}\text{-Gene 4-(term4)}_{z2}]_{x4}\text{-3'} \quad (IIa)$$

wherein:
Gene 1, Gene 2, Gene 3, Gene 4, "x1", "x2", "x3" and "x4" are such as above-defined;
"x5" represents an integer equal to 0 or 1;
"y1", "y2", "y2" "z1" and "z2", one independently from the others, represent an integer equal to 0 or 1;
when said recombinant yeast comprises at least two DNA constructs of formula (IIa), then "x1" to "x5", "y1", "y2", "z1" and "z2" may be identical or different;
"prom 1" is a regulatory sequence which controls the expression of the sequence encoding the gene 1;
"prom 2" is a regulatory sequence which controls the expression of the sequence encoding the gene 2;
"prom 3" is a regulatory sequence which controls the expression of the sequence encoding the gene 3;
"prom 4" is a regulatory sequence which controls the expression of the sequence encoding the gene 4;
"prom5" is a regulatory sequence which controls the expression of Gene 1, said prom5 being identical or different from prom1;
"term1" is a transcription terminator sequence that ends expression of the sequence encoding the gene 1;
"term2" is a transcription terminator sequence that ends expression of the sequence encoding the gene 2;
"term3" is a transcription terminator sequence that ends expression of the sequence encoding the gene 3;
"term4" is a transcription terminator sequence that ends expression of the sequence encoding the gene 4; and
"term5" is a transcription terminator sequence that ends expression of Gene 1, said term5 being identical or different from term1.

According to another particular embodiment, the recombinant yeast according to the invention may comprise at least one, preferably at least two, DNA construct(s) of formula (IIb), identical or different, wherein each formula (IIb) has the following formula:

$$5'\text{-[(prom5)}_{y1}\text{-}ALS\text{-term5]}_{x5}\text{-[prom1-}ALS\text{-term1]}_{x1}\text{-}$$
$$[\text{prom2-}ALD\text{-term2]}_{x2}\text{-[prom3-}BDH\text{-}$$
$$(\text{term3})_{z1}]_{x3}\text{-3' and } 5'\text{-[(prom4)}_{y2}\text{-}NOXE\text{-}$$
$$(\text{term4})_{z2}]_{x4}\text{-3'} \quad (IIb)$$

wherein:
ALS, ALD, BDH, NOXE, "x1", "x2", "x3", "x4", "x5" "y1", "y2", "z1" and "z2" are such as above-defined;
when said recombinant yeast comprises at least two DNA constructs of formula (IIb), then "x1" to "x5", "y1", "y2", "z1" and "z2" may be identical or different;
"prom 1" is a regulatory sequence which controls the expression of the sequence encoding the acetolactate synthase;
"prom 2" is a regulatory sequence which controls the expression of the sequence encoding the acetolactate decarboxylase;
"prom 3" is a regulatory sequence which controls the expression of the sequence encoding the butanediol dehydrogenase;
"prom 4" is a regulatory sequence which controls the expression of the sequence encoding the NADH oxidase;
"prom5" is a regulatory sequence which controls the expression of the sequence encoding the acetolactate synthase, said prom5 being identical or different from prom1;
"term1" is a transcription terminator sequence that ends expression of the sequence encoding the acetolactate synthase;

"term2" is a transcription terminator sequence that ends expression of the sequence encoding the acetolactate decarboxylase;

"term3" is a transcription terminator sequence that ends expression of the sequence encoding the butanediol dehydrogenase;

"term4" is a transcription terminator sequence that ends expression of the sequence encoding the NADH oxidase; and "term5" is a transcription terminator sequence that ends expression of the sequence encoding the acetolactate synthase, said term5 being identical or different from term1.

According to another particular embodiment, the recombinant yeast according to the invention may comprise at least two DNA constructs of formula (II), (IIa) or (IIb), provided that all copies of NOXE's nucleic acid are located at a single of the at least two DNA constructs of formula (II), (IIa) or (IIb).

According to another particular embodiment, the recombinant yeast according to the invention may comprise at least two, preferably strictly two, DNA constructs of the following formulae (IIc) and (IId):

$$5'\text{-}[(\text{prom}5)_{y1}\text{-}ALS\text{-}\text{term}5]_{x5}\text{-}[\text{prom}1\text{-}ALS\text{-}\text{term}1]_{x1}\text{-}[\text{prom}2\text{-}ALD\text{-}\text{term}2]_{x2}\text{-}[\text{prom}3\text{-}BDH\text{-}(\text{term}3)_{z1}]_{x3}\text{-}3' \text{ and } 5'\text{-}[(\text{prom}4)_{y2}\text{-}NOXE\text{-}(\text{term}4)_{z2}]_{x6}\text{-}3'; \text{ and} \quad (\text{IIc})$$

$$5'\text{-}[(\text{prom}5)_{y1}\text{-}ALS\text{-}\text{term}5]_{x5}\text{-}[\text{prom}1\text{-}ALS\text{-}\text{term}1]_{x1}\text{-}[\text{prom}2\text{-}ALD\text{-}\text{term}2]_{x2}\text{-}[\text{prom}3\text{-}BDH\text{-}(\text{term}3)_{z1}]_{x3}\text{-}3' \text{ and } 5'\text{-}[(\text{prom}4)_{y2}\text{-}NOXE\text{-}(\text{term}4)_{z2}]_{x7}\text{-}3'; \text{ and} \quad (\text{IId})$$

wherein:

ALS, ALD, BDH, NOXE, "prom1", "prom2", "prom3", "prom4", "prom5", "term1", "term2", "term3", "term4", "term5", "x1", "x2", "x3", "x5", "y1", "y2", "z1" and "z2" are such as above-defined;

"x1" to "x3" for each of formula (IIc) and (IId) being identical or different;

"x1" to "x3", "x5", "y1", "y2", "z1" and "z2" for each formulae (IIc) and (IId) being identical or different; and "x6" and "x7" represent integers ranging from 0 to 50, preferably from 0 to 20, preferably from 0 to 12, more particularly from 2 to 5, preferably from 3 to 4, and better still equal to 3, provided that only one among "x6" and "x7" represents 0.

This invention also pertains to a use of a recombinant yeast according to the present invention, for the production of 2,3-butanediol (BDO) and/or direct derivatives thereof.

In particular, said direct derivatives of 2,3-butanediol (BDO) may be selected from the group consisting of butanediene (BDE), Methyl-Ethyl-Ketone (MEK) or a mixture thereof.

The invention also concerns a method for producing 2,3-butanediol (BDO), said method comprising the steps of:

(a) culturing a recombinant yeast according to the present invention in an appropriate culture medium; and (c) recovering the 2,3-butanediol (BDO).

Preferably, the said culture medium comprises a carbon source, preferably selected in a group comprising glucose and sucrose.

DESCRIPTION OF THE FIGURES

FIG. 1 shows the metabolic pathway in a recombinant yeast strain so as to replace the production of ethanol in favor of 2,3-BDO.

DETAILED DESCRIPTION OF THE INVENTION

Definitions

The terms 2,3-butanediol, 2,3-BDO or BDO are used interchangeably in the present description and refer to butane-2,3-diol, also called dimethylene glycol.

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of 2,3-butanediol.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotidic sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Homologous promoters known to allow a high level of expression in yeast are the ones selected in the following group: ADH1, GPDH, TEF1, truncated HXT7, PFK1, FBA1, PGK1, TDH3, etc. Promoters particularly interesting in the present invention are hereinafter defined more in details.

In yeast, nucleic acid expression construct preferably comprises regulatory sequences, such as promoter and terminator sequences, which are operatively linked with the nucleic acid sequence coding for each of the considered genes, and more particularly for each of the above-mentioned ALS, ALD, BDH and NOXE enzymes according to the present invention.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of several copies of the said nucleic acid between a promoter, especially a strong promoter, and a terminator.

The "activity" of an enzyme is used interchangeably with the term "function" and designates, in the context of the invention, the capacity of an enzyme to catalyze the desired reaction.

The terms "reduced activity" or "attenuated activity" of an enzyme mean either a reduced specific catalytic activity of the protein obtained by mutation in the aminoacids sequence and/or decreased concentrations of the protein in the cell obtained by mutation of the nucleotidic sequence or by deletion of the cognate corresponding gene.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non-modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, the disrupted pyruvate decarboxylase gene(s) in which the above-mentioned DNA construct(s) is/are intended to be inserted may advantageously comprise one or more selectable marker(s) useful for the selection of transformed microbial cells. Preferably, said selectable markers are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces, Candida*, etc.) and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be effected by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from pyruvate. For maximal production of 2,3-BDO, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose, maltose, galactose or sucrose; polysaccharides such as starch or cellulose; or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is sucrose.

According to a particular embodiment, a carbon substrate according to the present invention does not consist of xylose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The presence of weak acids is known to be a limitation for growth and are often present in cellulose or molasses derived media.

Additional genetic modifications such as the disruption of the JEN1 gene (or systematic name: YKL217W or protein accession number P36035 (UniProtKB swiss-Prot)) and/or the over-expression of the HAA-1 gene (systematic name: YPR008W or accession number Q12753 (UniProtKB swiss-Prot)) lead to improve the strains resistance to weak acids in the implemented culture medium.

Jen 1 is a membrane protein responsible for lactate import in the cell (Casal M, et al. (1999), J. Bacteriol., 181(8): 2620-3).

HAA-1 is a transcriptional activator that controls the expression of membrane stress proteins responsible for resistance to weak acids. Its over expression enhances the resistance of yeast to acetic acids (Tanaka et al. (2012) Appl Environ Microbiol., 78(22): 8161-3).

The disruption of the JEN1 gene and the overexpression of the HAA-1 gene belong to the general knowledge of a man skilled in the art and may be notably carried out in using methods herein displayed.

In view of the herein after equation for the synthesis of 2,3-BDO in yeast, the conditions to consider in the present invention are necessarily aerobic conditions.

The terms "aerobic conditions" refers to concentrations of oxygen in the culture medium that are sufficient for an aerobic or facultative anaerobic microorganism to use di-oxygene as a terminal electron acceptor.

"Microaerobic condition" refers to a culture medium in which the concentration of oxygen is less than that in air, i.e. oxygen concentration up to 6% $O_2$.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

Recombinant Yeast According to the Invention

As above-mentioned, the present invention relates to a recombinant yeast having a reduced pyruvate decarboxylase activity, in the genome of which has been inserted:
- one or more nucleic acids encoding an acetolactate synthase or ALS,
- one or more nucleic acids encoding an acetolactate decarboxylase or ALD,
- one or more nucleic acids encoding a butanediol dehydrogenase or BDH, and
- one or more copies of a nucleic acids encoding a NADH oxidase or NOXE.

As shown in the examples herein, the inventors unexpectedly found that the presence of a nucleic acid encoding a NADH oxidase, advantageously the presence of a plurality of copies thereof, in a recombinant yeast in which the pyruvate decarboxylase activity has been reduced and in which it has been further integrated genes allowing expression of the ALS, ALD and BDH enzymes required for the synthesis of 2,3-BDO, not only contributes to stabilize said recombinant yeast but also allows a significant enhancing of the growth of this strain, as well as the yield of 2,3-BDO production.

The use of Crabtree positive yeast organisms such as *Saccharomyces cerevisiae*, and especially of recombinant yeast organisms such as *Saccharomyces cerevisiae*, for producing metabolites of interest is advantageous since, in contrast to bacteria, yeast cells have the ability to perform fermentation in the presence of oxygen in presence of sufficient amount of sugar such as glucose or sucrose. In contrast, bacteria perform fermentation in anaerobic conditions only. Further, yeast organisms are not subject to viral infection in contrast to bacteriophage for bacteria. Yet further, culture of yeast organisms are rarely subject to contamination by non-desired microorganisms such as bacteria because yeast cells cause rapid acidification of their environment up to pH4, e;g. the culture medium supporting their growth. Still further, yeast cells do not excrete number of undesired metabolites such as lactic acid, the presence of which in the culture medium is an actual drawback for subsequent purification of metabolite(s) of interest. Yet further, yeast organisms, including recombinant yeast organisms, have a higher genetic stability as compared to bacteria.

The equation for the synthesis of 2,3-BDO in yeast is:

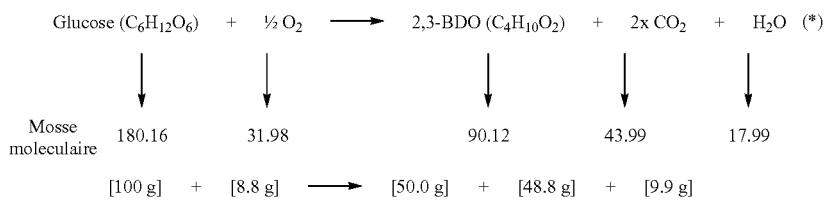

(*) possible due to the fact that *S. cerevisiae* can ferment even in the presence of oxygen.

In view of the above equation, the maximum theoretical yield of 2,3-BDO would be 100 g for an input of 200 g of glucose.

As it is shown in the examples herein, the effective yield of 2,3-BDO with recombinant yeast according to the present invention is very close to this maximum theoretical yield. According to the inventor's knowledge, such yield was never obtained until now.

Thus, the production with a high yield of 2,3-BDO is successfully reached in a recombinant yeast according to the invention, paving the way for industrial production of 2,3-BDO in using yeast.

Surprisingly, as it is also shown in the examples herein, no toxicity of the produced 2,3-BDO on the yeast cells is observed, even at high concentrations of synthesized 2,3-BDO. What is more, the synthesized 2,3-BDO is entirely exported outside the cells, thus substantially simplifying the purification process.

The NADH oxidase used in the recombinant yeast according to the present invention is a very specific "NADH-dependent" enzyme as it does not consume any carbonated acceptor. For this reason, the selected NADH oxidase does not interfere directly with the carbonated metabolism but replenishes the NAD$^+$ pool in producing water.

In this regard, the NADH oxidase used in the recombinant yeast according to the present invention differs notably from the "NADH-dependent" enzyme disclosed in the above-mentioned prior art documents, and especially in US 2011/0124060 and WO 2013/076144.

According to certain embodiments, the recombinant yeast may comprise one or more DNA construct(s) selected in a group comprising the following formulae:

$$5'\text{-[Gene 1]}_{x1}\text{-3' and 5'-[Gene 2]}_{x2}\text{-3' and 5'-[Gene 3]}_{x3}\text{-3' and 5'-[Gene 4]}_{x4}\text{-3'}, \quad (I)$$

$$5'\text{-[Gene 1]}_{x1}\text{-[Gene 2]}_{x2}\text{-[Gene 3]}_{x3}\text{-3' and 5'-[Gene 4]}_{x4}\text{-3'}, \quad (II)$$

$$5'\text{-[Gene 1]}_{x1}\text{-[Gene 2]}_{x2}\text{-3' and 5'-[Gene 3]}_{x3}\text{-[Gene 4]}_{x4}\text{-3'}, \quad (III)$$

$$5'\text{-[Gene 1]}_{x1}\text{-[Gene 2]}_{x2}\text{-[Gene 3]}_{x3}\text{-[Gene 4]}_{x4}\text{-3'}, \text{ and} \quad (IV)$$

a combination thereof,
wherein:
"Gene 1" means a nucleic acid selected from a group comprising ALS, ALD, BDH or NOXE;
"Gene 2" means a nucleic acid selected from a group comprising ALS, ALD, BDH or NOXE but different from gene 1;
"Gene 3" means a nucleic acid selected from a group comprising ALS, ALD, BDH or NOXE but different from genes 1 and 2;
"Gene 4" means a nucleic acid selected from a group comprising ALS, ALD, BDH or NOXE but different from genes 1 to 3;
"ALS" is a nucleic acid encoding an acetolactate synthase;
"ALD" is a nucleic acid encoding an acetolactate decarboxylase;
"BDH" is a nucleic acid encoding a butanediol dehydrogenase;
"NOXE" is a nucleic acid encoding a NADH oxidase;
each of "x1", "x2", "x3" and "x4", one independently from the others, represents an integer ranging from 0 to 50, preferably from 0 to 20, and provided that said recombinant yeast comprises at least one nucleic acid encoding for each of ALS, ALD, BDH and NOXE.

Preferably, each among "x1", "x2", "x3" and "x4", independently the ones of the others, represents an integer ranging from 0 to 10, more particularly ranging from 0 to 5, in particular ranging from 0 to 3, and still better represents an integer equal to 1.

As intended herein, each of x1, x2, x3 and x4 may have a value selected in a group comprising 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

In certain embodiments wherein, in a DNA construct of formulae (I) to (IV) above, one or more of the integers "x1", "x2", "x3" and/or "x4", one independently from the others, has a value of two or more, then each of the two or more copies of the corresponding gene among related Gene 1, Gene 2, Gene 3 and/or Gene 4 may be identical or different. Various distinct sequences of ALS, ALD, BDH and NOXE are depicted in Table 1 herein.

In illustrative embodiments of a DNA construct selected among those of formulae (I) to (IV) above, wherein "x1" is an integer equal to 2 and Gene 1 is a nucleic acid encoding an acetolactate synthase (ALS), then the two ALS-coding sequences contained in the said DNA construct may be identical or different, For example, according to this particular embodiment, it means that the first copy of the nucleic acid encoding an acetolactate synthase may be the nucleic acid encoding ALS.Bs and the second copy of the nucleic acid encoding an acetolactate synthase may be the nucleic acid encoding ALS.Pp.

In the embodiments of a recombinant yeast according to the invention wherein the said recombinant yeast comprises at least two DNA constructs selected in the group comprising the DNA constructs of formulae (I) to (IV), each DNA construct, and more particularly each of gene among related Gene 1, Gene 2, Gene 3 and/or Gene 4 contained therein, may be identical or different.

Herein after are presented some illustrative embodiments of a DNA construct selected in a group comprising the DNA constructs of formula (I), (II), (III) and (IV).

Recombinant Yeast Comprising One DNA Construct of Formula (I):

$$5'\text{-[ALS]}_2\text{-3' and 5'-[ALD]}_2\text{-3' and 5'-[BDH]}_2\text{-3' and }5'\text{-[NOXE]}_3\text{-3'}, \quad (I)$$

A recombinant yeast comprising a DNA construct of formula (I) above has a reduced pyruvate decarboxylase activity, and possesses the four following DNA sub-constructs (i) to (iv) that have been introduced in the genome thereof:

(i) a DNA sub-construct comprising two nucleic acids, identical or distinct one from the other(s), each nucleic acid encoding ALS, said DNA sub-construct being introduced at a first location in the genome of said recombinant yeast;

(ii) a DNA sub-construct comprising two nucleic acids, identical or distinct one from the other, each nucleic acid encoding ALD, said DNA sub-construct being introduced at a second location in the genome of said recombinant yeast, distinct from the location wherein the nucleic acids encoding ALS have been inserted;

(iii) a DNA sub-construct comprising two nucleic acids, identical or distinct one from the other, each nucleic acid encoding BDH, said DNA sub-construct being introduced at a third location in the genome of said recombinant yeast, distinct from the first and second locations wherein the nucleic acids encoding ALS and the nucleic acids encoding ALD have been inserted; and (iv) a DNA sub-construct comprising three nucleic acids, identical or distinct one from the other(s), each nucleic acid encoding NOXE, said DNA sub-construct being introduced at a fourth location in the genome of said recombinant yeast, distinct from the first, second and third locations wherein the nucleic acids encoding ALS and the nucleic acids encoding ALD and BDH, respectively, have been inserted.

In some embodiments, the required reduced pyruvate decarboxylase activity of the said specific recombinant yeast may be obtained by insertion in at least one of the yeast pdc genes of at least one DNA sub-construct (i) to (iv), or alternatively a combination thereof.

Recombinant Yeast Comprising One DNA Construct of Formula (II):

$$5'\text{-[ALS]}_1\text{-[ALD]}_1\text{-[BDH]}_1\text{-3' and 5'-[NOXE]}_3\text{-3'} \quad (II)$$

The resulting recombinant yeast has a reduced pyruvate decarboxylase activity, and has a genome wherein has been inserted the two following DNA sub-constructs (A) and (B), namely:

(A) a first DNA sub-construct 5'-[ALS]$_1$-[ALD]$_1$-[BDH]$_1$-3', said first DNA sub-construct being introduced at a first location in the genome of said recombinant yeast, and said first DNA sub-construct comprising;

(i) one nucleic acid encoding ALS;
(ii) one nucleic acid encoding ALD; and
(iii) one nucleic acid encoding BDH;
(B) a second DNA sub-construct 5'-[NOXE]$_3$-3', said DNA sub-construct being introduced at a second location in the genome of said recombinant yeast, distinct from the first location wherein the first DNA sub-construct has been inserted, and said second DNA sub-construct comprising
(iv) three nucleic acids, identical or distinct one from the other(s), each nucleic acid encoding NOXE.

In certain embodiments, the required reduced pyruvate decarboxylase activity of said specific recombinant yeast may be obtained by insertion in at least one of the yeast pdc genes of first DNA sub-construct.

Recombinant Yeast Comprising Two DNA Constructs of Formula (II):

$$5'\text{-}[ALS]_1\text{-}[ALD]_1\text{-}[BDH]_1\text{-}3' \text{ and } 5'\text{-}[NOXE]_3\text{-}3', \text{ and} \quad \text{(II-1)}$$

$$5'\text{-}[ALS]_1\text{-}[ALD]_1\text{-}[BDH]_1\text{-}3' \text{ and } 5'\text{-}[NOXE]_0\text{-}3' \quad \text{(II-2)}$$

The resulting recombinant yeast has a reduced pyruvate decarboxylase activity, and has a genome wherein has been inserted the three following DNA sub-constructs (A), (B) and (C), namely:
(A) a first DNA sub-construct 5'-[ALS]$_1$-[ALD]$_1$-[BDH]$_1$-3', said first DNA sub-construct being introduced at a first location in the genome of said recombinant yeast, and said first DNA sub-construct comprising;
(i) one nucleic acid encoding ALS;
(ii) one nucleic acid encoding ALD; and
(iii) one nucleic acid encoding BDH;
(B) a second DNA sub-construct 5'-[ALS]$_1$-[ALD]1-[BDH]$_1$-3', said second DNA sub-construct being introduced at a second location in the genome of said recombinant yeast, and said second DNA sub-construct comprising;
(i) one nucleic acid encoding ALS;
(ii) one nucleic acid encoding ALD; and
(iii) one nucleic acid encoding BDH;
and
(C) a third DNA sub-construct 5'-[NOXE]$_3$-3', said DNA sub-construct being introduced at a third location in the genome of said recombinant yeast, distinct from the first location wherein the first DNA sub-construct has been inserted, and distinct from the second location wherein the second DNA sub-construct has been inserted and said third DNA sub-construct comprising (iv) three nucleic acids, identical or distinct one from the other(s), each nucleic acid encoding NOXE.

In certain embodiments, the required reduced pyruvate decarboxylase activity of said specific recombinant yeast may be obtained by insertion in at least one of the yeast pdc genes of first DNA sub-construct and/or of second DNA sub-construct.

Recombinant Yeast Comprising One DNA Construct of Formula (III):

$$5'\text{-}[ALS]_2\text{-}[ALD]_2\text{-}3' \text{ and } 5'\text{-}[BDH]_2\text{-}[NOXE]_3\text{-}3', \quad \text{(III)}$$

A recombinant yeast comprising a DNA construct of formula (III) above has a reduced pyruvate decarboxylase activity, and possesses a genome wherein been inserted the two following DNA sub-constructs (A) and (B), namely:
(A) a first DNA sub-construct 5'-[ALS]$_1$-[ALD]$_4$-3', said first DNA sub-construct being introduced at a first location in the genome of said recombinant yeast, and said first DNA sub-construct comprising;
(i) two nucleic acids, identical or distinct one from the other, each nucleic acid encoding ALS; and
(ii) two nucleic acids, identical or distinct one from the other, each nucleic acid encoding ALD;
(B) a second DNA sub-construct 5'-[BDH]$_3$-[NOXE]$_3$-3', said DNA sub-construct being introduced at a second location in the genome of said recombinant yeast, distinct from the first location wherein the first DNA sub-construct has been inserted, and said second DNA sub-construct comprising:
(iii) two nucleic acids, identical or distinct one from the other, each nucleic acid encoding BDH; and
(iv) three nucleic acids, identical or distinct one from the other(s), each nucleic acid encoding NOXE.

In certain embodiments, the required reduced pyruvate decarboxylase activity of said specific recombinant yeast may be obtained by insertion in at least one of the yeast pdc genes of first DNA sub-construct and/or of second DNA sub-construct.

Recombinant Yeast Comprising One DNA Construct of Formula (IV):

$$5'\text{-}[ALS]_2\text{-}[ALD]_2\text{-}[BDH]_2\text{-}[NOXE]_3\text{-}3', \quad \text{(IV)}$$

A recombinant yeast comprising a DNA construct of formula (IV) above has a reduced pyruvate decarboxylase activity and possesses a genome wherein has been inserted one DNA construct located at a desired location in the genome of said recombinant yeast, said DNA construct comprising;
(i) two nucleic acids, identical or distinct one from the other, each nucleic acid encoding ALS;
(ii) two nucleic acids, identical or distinct one from the other, each nucleic acid encoding ALD;
(iii) two nucleic acids, identical or distinct one from the other, each nucleic acid encoding BDH; and
(iv) three nucleic acids, identical or distinct one from the other(s), each nucleic acid encoding NOXE.

In certain embodiments, the required reduced pyruvate decarboxylase activity of said specific recombinant yeast may be obtained by insertion of said DNA construct in at least one of the yeast pdc genes.

For each of these five illustrative embodiments above of a recombinant yeast according to the invention, and as above-mentioned, when "x1" to "x4", one independently from the others, represent(s) an integer having a value of two or more, then:

one copy of ALS within a single DNA construct may be identical to another copy of ALS comprised in the said DNA construct or may be identical to all the other copies of ALS contained in the said DNA construct, or alternatively the said one copy of ALS may be distinct from each other copy of ALS contained in the said DNA construct.

one copy of ALD within a single DNA construct may be identical to another copy of ALD comprised in the said DNA construct or may be identical to all the other copies of ALD contained in the said DNA construct, or alternatively the said one copy of ALD may be distinct from each other copy of ALD contained in the said DNA construct.

one copy of BDH within a single DNA construct may be identical to another copy of BDH comprised in the said DNA construct or may be identical to all the other copies of BDH contained in the said DNA construct, or alternatively the said one copy of BDH may be distinct from each other copy of BDH contained in the said DNA construct.

one copy of NOXE within a single DNA construct may be identical to another copy of NOXE comprised in the said DNA construct or may be identical to all the other copies of NOXE contained in the said DNA construct, or alternatively the said one copy of NOXE may be distinct from each other copy of NOXE contained in the said DNA construct.

According to certain specific embodiments, a recombinant yeast according to the invention may comprise at least one, preferably at least two, DNA construct(s) of the above-mentioned formula (II), wherein "Gene 4" means a nucleic acid encoding a NADH oxidase (NOXE).

According to these specific embodiments, each nucleic acid among Gene 1, Gene 2 and Gene3 necessarily means a nucleic acid selected from a group comprising ALS, ALD and BDH. In these embodiments, at least one copy of the inserted ALS, ALD and BDH is present. In the embodiments wherein only one construct of formula (II) is inserted in the yeast genome, then each nucleic acid among Gene 1, Gene 2 and Gene3 necessarily means a nucleic acid selected from a group comprising ALS, ALD and BDH and one copy of each of ALS, ALD and BDH is present. In the embodiments wherein a set of two or more constructs of formula (II) are inserted in the yeast genome, then each nucleic acid among Gene 1, Gene 2 and Gene3 necessarily means a nucleic acid selected from a group comprising ALS, ALD and BDH and at least one copy of each of ALS, ALD and BDH is present in the said set of two or more DNA constructs of formula (II).

In addition, when the said recombinant yeast according to the invention comprises at least two DNA constructs of the above-formula (II), then said DNA constructs of the above-mentioned formula (II) may be identical or different.

According to a preferred embodiment, a recombinant yeast according to the invention may comprise at least one, preferably at least two, DNA construct(s) of formula (IIa), identical or different, wherein each formula (IIa) has the following formula:

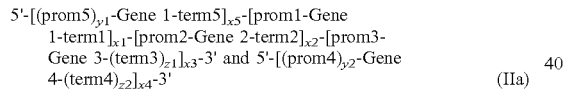

(IIa)

wherein:
Gene 1, Gene 2, Gene 3 and Gene 4, "x1", "x2", "x3" and "x4" are such as above-defined;
"x5" represents an integer equal to 0 or 1;
"y1", "y2", "z1" and "z2", one independently from the others, represent an integer equal to 0 or 1;
when said recombinant yeast comprises at least two DNA construct(s) of formula (IIa), then "x1" to "x5", "y1", "y2", "z1" and "z2" may be identical or different;
"prom 1" is a regulatory sequence which controls the expression of the sequence encoding the gene 1;
"prom 2" is a regulatory sequence which controls the expression of the sequence encoding the gene 2;
"prom 3" is a regulatory sequence which controls the expression of the sequence encoding the gene 3;
"prom 4" is a regulatory sequence which controls the expression of the sequence encoding the gene 4;
"prom5" is a regulatory sequence which controls the expression of Gene 1, said prom5 being identical or different from prom1;
"term1" is a transcription terminator sequence that ends expression of the sequence encoding the gene 1;
"term2" is a transcription terminator sequence that ends expression of the sequence encoding the gene 2;
"term3" is a transcription terminator sequence that ends expression of the sequence encoding the gene 3;
"term4" is a transcription terminator sequence that ends expression of the sequence encoding the gene 4; and
"term5" is a transcription terminator sequence that ends expression of Gene 1, said term5 being identical or different from term1.

For a better clarity regarding the characteristics "x5" and "y1", is herein after presented examples to illustrate more in details related particular embodiments:
when "x5" is an integer equal to 1 and "y1" represents an integer equal to 0, then it means that the considered Gene 1 is under the control of the promoter of the gene of the recombinant yeast in which the considered DNA construct has been inserted; or
when "x5" is an integer equal to 1 and "y1" represents an integer equal to 1, then it means that the considered Gene 1 is under the control of the promoter "prom5". In this regard, the sequence of promoter of the endogenous gene, preferably of pdc gene, in which the DNA construct is inserted is eliminated, or at least interrupted, as well as the sequence of its related coding region.

In addition, regarding notably the characteristics "y2" and "z2", is herein after presented examples to illustrate more in details related particular embodiments (of course, in these herein after examples, "x4" represents an integer equal to 1 or more):
when "y2" is an integer equal to 0, then it means that the considered Gene 4 is under the control of the promoter of the gene of the recombinant yeast in which the considered DNA construct has been inserted; or
when "y2" is an integer equal to 1, then it means that the considered Gene 4 is under the control of the promoter "prom4". In this regard, the sequence of promoter of the endogenous gene in which the DNA construct is inserted is eliminated, or at least interrupted, as well as the sequence of its related coding region.
when "z2" is an integer equal to 0, then it means that the considered Gene 4 is linked to the transcription terminator of the gene of the recombinant yeast in which the considered DNA construct has been inserted; or
when "z2" is an integer equal to 1, then it means that the considered Gene 4 is linked to the transcription terminator "term4". In this regard, the sequence of the transcription terminator of the endogenous gene in which the DNA construct is inserted is eliminated, or at least interrupted, as well as the sequence of its related coding region.

Regarding "z1" when present in formulas described in the present specification, the above-mentioned regarding "z2" apply mutatis mutandis.

According to another preferred embodiment, a recombinant yeast according to the invention may comprise at least one, preferably at least two, DNA construct(s) of the following formula (IIb):

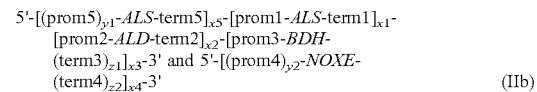

(IIb)

wherein:
ALS, ALD, BDH, NOXE, "x1", "x2", "x3", "x4", "x5", "y1", "y2", "z1" and "z2" are such as above-defined:
when said recombinant yeast comprises at least two DNA construct(s) of formula (IIb), then "x1" to "x5", "y1", "y2", "z1" and "z2" may be identical or different;
"prom 1" is a regulatory sequence which controls the expression of the sequence encoding the acetolactate synthase;

"prom 2" is a regulatory sequence which controls the expression of the sequence encoding the acetolactate decarboxylase;

"prom 3" is a regulatory sequence which controls the expression of the sequence encoding the butanediol dehydrogenase;

"prom 4" is a regulatory sequence which controls the expression of the sequence encoding the NADH oxidase;

"prom5" is a regulatory sequence which controls the expression of the sequence encoding the acetolactate synthase, said prom5 being identical or different from prom1;

"term1" is a transcription terminator sequence that ends expression of the sequence encoding the acetolactate synthase;

"term2" is a transcription terminator sequence that ends expression of the sequence encoding the acetolactate decarboxylase;

"term3" is a transcription terminator sequence that ends expression of the sequence encoding the butanediol dehydrogenase;

"term4" is a transcription terminator sequence that ends expression of the sequence encoding the NADH oxidase; and "term5" is a transcription terminator sequence that ends expression of the sequence encoding the acetolactate synthase, said term5 being identical or different from term1.

According to another preferred embodiment, a recombinant yeast according to the invention may comprise at least two DNA constructs of formula (II), (IIa) or (IIb), provided that all copies of NOXE's nucleic acid are located at a single of the at least two DNA constructs of formula (II), (IIa) or (IIb).

According to another preferred embodiment, a recombinant yeast according to the invention may comprise at least two, preferably strictly two, DNA constructs of following formulae (IIc) and (IId):

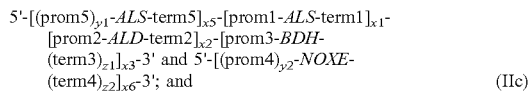
(IIc)

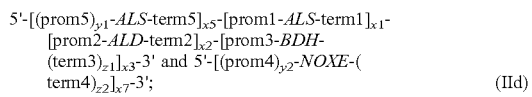
(IId)

wherein:

ALS, ALD, BDH, NOXE, "prom1", "prom2", "prom3", "prom4", "prom5", "term1", "term2", "term3", "term4" and "term5", "x1", "x2", "x3", "x5", "y1", "y2", "z1" and "z2" are such as above-defined; and "x1" to "x3", "x5", "y1", "y2", "z1" and "z2" for each formulae (IIc) and (IId) being identical or different; and "x6" and "x7" represent integers ranging from 0 to 50, preferably from 0 to 20, preferably from 0 to 12, more particularly from 2 to 5, preferably from 3 to 4, and better still equal to 3, provided that only one among "x6" and "x7" represents 0.

Advantageously, the first gene 1 in 5'- in a DNA construct of formulae (I) to (IV), preferably a gene represented by a nucleic acid encoding ALS, is under the control of the promoter of the gene of the recombinant yeast in which the considered DNA construct have been inserted.

More particularly, it means that, for a DNA construct of formula (IIa), (IIb), (IIc) or (IId), "x5" advantageously represents an integer equal to 1 and "y1" represents an integer equal to 0.

In view of the complexity of the above-mentioned DNA constructs and DNA sub-constructs according to the present invention, it is emphasized that:

regarding one DNA construct of the invention, when "x1", "x2", "x3" and/or "x4" represent(s) an integer greater than or equal to 2, then:

each copy for a related nucleic acid among Gene 1, Gene 2, Gene 3 and/or Gene 4 may be identical or different; and/or the promoter and/or terminator for each copy for a related nucleic acid among Gene 1, Gene 2, Gene 3 and/or Gene 4 may be identical or different;

when a recombinant yeast comprises at least two DNA constructs, said at least two DNA constructs may be identical or different regarding:

(i) their general formula in that a DNA construct may be characterized by a formula selected among the group comprising formulae (I) to (IV);

(ii) the value of "x1" to "x7", "y1", "y2", "z1" and/or "z2";

(iii) the nature of the promoter regarding a same gene;

(iv) the nature of the terminator regarding a same gene; and/or (v) the nature of same gene itself in that ALS, ALD, BDH and NOXE may derive from organisms belonging to different genera, as notably hereinafter displayed in Table 1.

Methods implemented to realize a DNA construct such as above-defined belong to the general knowledge of the man of the art.

In this regard, the one skilled in the art may advantageously refer to the method described in Shao et al. (Nucleic Acids Research, 2009, Vol. 37, No. 2: e16) and Shao et al. (Methods in Enzymology, 2012 Elsevier Inc., Vol. 517: 203, eventually with only minor variation, and is more particularly developed in the herein after examples.

Reduced Pyruvate Decarboxylase Activity

Endogenous pyruvate decarboxylase activity in yeast converts pyruvate to acetaldehyde, which is then converted to ethanol or to acetyl-CoA via acetate.

As previously mentioned, the present invention relates to a recombinant yeast having reduced pyruvate decarboxylase activity, in the genome of which has been inserted a specific DNA construct.

According to a particular embodiment, the recombinant yeast is characterized by the fact that one or more endogenous pyruvate decarboxylase-encoding gene(s) may be switched off.

The pyruvate decarboxylase activity of a recombinant yeast according to the invention may be reduced by all methods known by a man skilled in the art.

In this regard, the pyruvate decarboxylase activity of a recombinant yeast according to the invention may for example be reduced by (i) disrupting at least one gene encoding a pyruvate decarboxylase by inserting within said at least one gene encoding a pyruvate decarboxylase at least one exogenous DNA construct, (ii) mutations in regulatory regions, (iii) mutations in a start codon, notably by replacing AUG by GUG, and (iv) mutations in coding sequences altering the enzymatic activity (v) mutations, insertions or deletion in the coding sequence altering the protein stability (vi) mutations altering the pyruvate decarboxylase mRNA half life. Regarding the first option (i), the DNA construct implemented to disrupt a considered pdc gene may be an exogenous DNA construct different from DNA constructs according to the invention as previously described, a DNA construct according to the invention, or a combination thereof.

Also, and as above-mentioned, DNA constructs according to the invention of formula (I), (II) and (III) are each composed of two or more DNA sub-constructs.

Therefore, according to a particular variant of realization, the pyruvate decarboxylase activity of a recombinant yeast according to the invention may be reduced by disrupting at least one gene encoding a pyruvate decarboxylase by inserting within said gene only at least one DNA sub-constructs of at least one DNA constructs according to the invention of formula (I), (II) and (III).

Preferably, the endogenous pyruvate decarboxylase activity may be reduced by disruption of at least one pdc gene.

Indeed, yeasts may have one or more genes encoding pyruvate decarboylase. For example, there is one gene encoding pyruvate decarboxylase in *Kluyveromryces lactis*, while there are three isozymes of pyruvate decarboxylase encoded by the PDC1, PCD5, and PDC6 genes in *Saccharomyces cerevisiae*, as well as a pyruvate decarboxylase regulatory gene PDC2.

Preferably, and as herein after defined, a recombinant yeast according to the invention may be a recombinant *Saccharomyces* genus, and preferably a recombinant *Saccharomyces cerevisiae* species.

Accordingly, the recombinant yeast preferably belongs to the *Saccharomyces* genus, and preferably to the *Saccharomyces cerevisiae* species.

In this regard, and according to a first variant, the pyruvate decarboxylase activity may be reduced by disruption of at least one pdc gene, preferably of at least two pdc genes, and more particularly of only two pdc genes.

In addition, the disrupted pdc gene(s) may be selected from the group consisting of pdc1, pdc5, pdc6 and a mixture thereof, and preferably of pdc1 and pdc6.

Preferably, when the recombinant yeast belongs to the *Saccharomyces* genus, then the pyruvate decarboxylase activity may be reduced by disruption of at least two pdc genes, preferably selected from the group consisting of pdc1, pdc5, pdc6 and a combination thereof, and more particularly from the group consisting of pdc1 and pdc6.

Indeed, the interruption of the three pdc genes in *Saccharomyces* genus, preferably, *Saccharomyces cerevisiae* species, dramatically reduces strain growth, rendering it incompatible with any industrial application.

According to a particular variant, in *Saccharomyees* genus, preferably *Saccharomyces cerevisiae* species, only pdc1 and pdc6 genes are disrupted and the expression of pdc5 is attenuated.

The method implemented to attenuate the expression of a specific gene belongs to the general knowledge of the man of the art.

In this regard, the one skilled in the art may advantageously refer to any method that is well known in the art.

Advantageously, for attenuating the expression of pdc 5, its transcription may be placed under the control of a weak promoter, such as notably RPLA1, URA3, MET25, HIS3, TRP1, GAP1, NUP57 or TFC1, and preferably RPLA1 (=Sequence SEQ ID NO: 37).

A method implemented to measure the activity level of a pyruvate decarboxylase belongs to the general knowledge of the man of the art.

In this regard, the one skilled in the art may advantageously refer to the method described in Wang et al. (Biochemistry, 2001, 40: 1755-1763).

Acetolactate Synthase

The acetolactate synthase (ALS) enzyme (also known as acetohydroxy acid synthase (AHAS), α-acetohydroxy acid synthetase, α-acetohydroxyacid synthase, α-acetolactate synthase, α-acetolactate synthetase, acetohydroxy acid synthetase, acetohydroxyacid synthase, acetolactate pyruvate-lyase (carboxylating), acetolactic synthetase) is a protein which catalyzes the first step in the synthesis of the branched-chain amino acids (valine, leucine, and isoleucine).

ALS is an enzyme specifically involved in the chemical reaction involving the conversion of two pyruvate molecules to an acetolactate molecule and carbon dioxide. The reaction uses thyamine pyrophosphate in order to link the two pyruvate molecules.

A method implemented to measure the activity level of an acetolactate synthase belongs to the general knowledge of the man of the art.

In this regard, the one skilled in the art may advantageously refer to the method described in Poulsen et al. (Eur. J. Biochem. 185, 1989: 433-439).

Preferred acetolactate synthase in the present invention is known by the EC number 2.2.1.6.

According to a preferred embodiment, the nucleic acid(s) encoding an acetolactate synthase or ALS may be nucleic acid(s) preferably selected from a group comprising *Bacillus subtilis*, *Nicotiana tabacum*, *Paenibacillus polymyxa*, and a mixture thereof, and preferably *Nicotiana tabacum* and *Paenibacillus polymyxa*.

According to a yet preferred embodiment, the nucleic acid(s) encoding an acetolactate synthase may be nucleic acid(s) selected from the group consisting of sequences having at least 65%, preferably at least 80%, nucleic acid identity with the nucleic acid sequences SEQ ID NO: 1, 3 and 5.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding an acetolactate synthase may be nucleic acid(s) encoding an amino acid sequence selected from the group consisting of sequences having at least 65%, preferably at least 80%, identity with sequences SEQ ID NO: 2, 5 and 6.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of ALS in the present invention is regulated by at least one promoter and at least one terminator, such as herein after defined more in details, which are present in 5' and 3' position respectively of the nucleic acid sequence encoding the ALS.

Acetolactate Decarboxylase

The acetolactate decarboxylase (ALD) enzyme (also known as α-acetolactate decarboxylase, (S)-2-hydroxy-2-methyl-3-oxobutanoate carboxy-lyase, (S)-2-hydroxy-2-methyl-3-oxobutanoate carboxy-lyase [(R)-2-acetoin-forming] or (S)-2-hydroxy-2-methyl-3-oxobutanoate carboxy-lyase [(3R)-3-hydroxybutan-2-one-forming]) belongs to the family of lyases, specifically the carboxy-lyases, which cleave carbon-carbon bonds and participates in butanoate metabolism and c5-branched dibasic acid metabolism.

ALD is an enzyme specifically involved in the chemical reaction involving the conversion of α-acetolactate molecule to an acetoine molecule and carbon dioxide.

A method implemented to measure the activity level of an acetolactate decarboxylase belongs to the general knowledge of the man of the art.

In this regard, the one skilled in the art may advantageously refer to the method described in Dulieu et al. (Enzyme and Microbial Technology 25, 1999: 537-542).

Preferred acetolactate decarboxylase in the present invention is known by the EC number 4.1.1.5.

According to a preferred embodiment, the nucleic acid(s) encoding an acetolactate decarboxylase or ALD may be nucleic acid(s) selected from the group comprising *Brevibacillus brevis*, *Enterobacter aerogenes*, *Lactococcus lactis*, and a mixture thereof, and preferably *Brevibacillus brevis* and *Enterobacter aerogenes*.

According to a yet preferred embodiment, the nucleic acid(s) encoding an acetolactate decarboxylase or ALD may be nucleic acid(s) selected from the group consisting of sequences having at least 36%, preferably at least 80%, nucleic acid identity with the nucleic acid sequences SEQ ID NO: 7, 9 and 11.

As described herein, a nucleic acid sequence having at least 36% nucleotide identity with a reference nucleic acid sequence encompasses nucleic acid sequences having at least 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding an acetolactate decarboxylase may be nucleic acid(s) encoding an amino acid sequence selected from the group consisting of sequences having at least 36%, preferably at least 80% identity with sequences SEQ ID NO: 8, 10 and 12.

As described herein, an amino acid sequence having at least 36% amino acid identity with a reference amino acid sequence encompasses amino acid sequences having at least 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of ALD in the present invention is regulated by at least one promoter and at least one terminator, such as herein after defined more in details, which are respectively present in 5' and 3' position of the nucleic acid sequence encoding the ALD.

Butanediol Dehydrogenase

The butanediol dehydrogenase (BDH) enzyme (also known as (R,R)-butanediol dehydrogenase, (R)-2,3-butanediol dehydrogenase, (R)-diacetyl reductase, 1-amino-2-propanol dehydrogenase, 1-amino-2-propanol oxidoreductase, 2,3-butanediol dehydrogenase, aminopropanol oxidoreductase, butylene glycol dehydrogenase, butyleneglycol dehydrogenase, D-(−)-butanediol dehydrogenase, D-1-amino-2-propanol dehydrogenase, D-1-amino-2-propanol:NAD(2) oxidoreductase, D-aminopropanol dehydrogenase, D-butanediol dehydrogenase, Diacetyl (acetoin) reductase) belongs to the family of oxidoreductases, specifically those acting on the CH—OH group of donor with NAD+ or NADP+ as acceptor.

BDH is an enzyme specifically involved in the chemical reaction involving the conversion of an acetoin molecule using NADH$^+$ and H$^+$ to a butane-2,3-diol molecule and NAD$^+$.

A method implemented to measure the activity level of α-butanediol dehydrogenase belongs to the general knowledge of the man of the art.

In this regard, the one skilled in the art may advantageously refer to the protocol described in Gao et al. (2012), journal of basic microbiology 52, 1-9. In particular, the BDH activity is monitored following the appearance of NADH through the absorbance at 340 nm.

Preferred butanediol dehydrogenase in the present invention is known by the EC number 1.1.1.4.

According to a preferred embodiment, the nucleic acid(s) encoding a butanediol dehydrogenase or BDH may be nucleic acid(s) selected from the group comprising *Enterobacter aerogenes*, *Paenibacillus polymyxa*, *Klebsiella oxycota*, *Saccharomyces cerevisiae* and a mixture thereof, and preferably *Enterobacter aerogenes* and *Saccharomyces cerevisiae*.

More particularly, when the nucleic acid(s) encoding a butanediol dehydrogenase is a nucleic acid selected from *Saccharomyces cerevisiae*, it means that there is an overexpression of the nucleic acid encoding the endogeneous butanediol dehydrogenase.

According to another preferred embodiment, the nucleic acid(s) encoding a butanediol dehydrogenase may be nucleic acid(s) selected from the group consisting of sequences having at least 63%, preferably at least 80%, identity with sequences SEQ ID NO: 13, 15, 17 and 19.

As described herein, a nucleic acid sequence having at least 63% nucleotide identity with a reference nucleic acid sequence encompasses nucleic acid sequences having at least 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding a butanediol dehydrogenase may be nucleic acid(s) encoding an amino acid sequence selected from the group consisting of sequences having at least 63%, preferably at least 80%, nucleic acid identity with the nucleic acid sequences SEQ ID NO: 14, 16, 18 and 20.

As described herein, an amino acid sequence having at least 63% amino acid identity with a reference amino acid sequence encompasses amino acid sequences having at least 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

According to a particular embodiment, when the nucleic acid(s) encoding the butanediol dehydrogenase is/are nucleic acid(s) selected from the group comprising *Enterobacter aerogenes, Paenibacillus polymyxa, Klebsiella oxycota* and a mixture thereof, then the gene encoding the endogenous butanediol dehydrogenase is switched off.

As above-mentioned, the expression level of BDH in the present invention is regulated by at least one promoter and at least one terminator, such as herein after defined more in details, which are respectively present in 5' and 3' position of the nucleic acid sequence encoding the BDH.

NADH Oxidase

The inactivation or reduction of activity of at least one pdc gene inactivates or reduces the ethanol fermentation pathway in yeast. In consequence, this induces an unbalanced redox state which is only partially relieved by the expression of BDH. Indeed, the pathway from glucose to 2 pyruvate generates 2 NADH equivalent, while the transformation of 2 pyruvate to butanediol recycles only 1 NADH into NAD$^+$ (see FIG. 1).

The inventors found that a bacterial water forming NADH oxidase (also called in the present description NOXE oxidase or NOXE) enzyme, in a specific expression level, can not only allow to equilibrate the redox state which allows enhancing the stability of this strain but also allows enhancing the growth of this strain and further improving the yield of 2,3-BDO.

A bacterial water forming NADH oxidase is an enzyme that catalyses the following reaction:

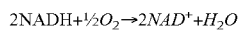

$$2NADH + \tfrac{1}{2}O_2 \rightarrow 2NAD^+ + H_2O$$

Preferred water forming NADH oxidase in the present invention are known by the EC number 1.6.3.1 and 1.6.99.3 (also known as NAD(P)H oxidase (H(2)O(2)-forming), dual oxidase, NAD(P)H oxidase, ThOX, THOX2, Thyroid NADPH oxidase, Thyroid oxidase Thyroid oxidase 2 for EC 1.6.3.1 and NADH dehydrogenase, Beta-NADH dehydrogenase dinucleotide, Cytochrome c reductase, Diaphorase, Dihydrocodehydrogenase I dehydrogenase, Dihydronicotinamide adenine dinucleotide dehydrogenase, Diphosphopyrinase, DPNH diaphorase, NADH diaphorase, NADH hydrogenase, NADH oxidoreductase, NADH-menadione oxidoreductase, NADH:cytochrome c oxidoreductase, Reduced diphosphopyridine nucleotide diaphorase, Type 1 dehydrogenase, Type I dehydrogenase for EC 1.6.99.3).

A water forming NADH oxidase which may be considered in the present invention is notably described in WO 2006/134277.

A method implemented to measure the activity level of a NADH oxidase according to the invention belongs to the general knowledge of the man of the art.

In this regard, the one skilled in the art may advantageously refer to the method described in Lopez D E FELIPE et al. (International Daily Journal, 2001, vol. 11: 37-44 (ISSN 0958-6946)).

According to a preferred embodiment, the nucleic acid(s) encoding a NADH oxidase or NOXE may be nucleic acid(s) selected from the group comprising *Streptococcus pneumoniae, Lactococcus lactis, Enterococcus faecalis, Lactobacillus brevis* and a mixture thereof, and preferably *Streptococcus pneumoniae*.

According to another preferred embodiment, the nucleic acid(s) encoding a NADH oxidase may be nucleic acid(s) selected from the group consisting of sequences having at least 78%, preferably at least 80%, nucleic acid identity with the nucleic acid sequences SEQ ID NO: 21, 23, 25 and 27.

As described herein, a nucleic acid sequence having at least 78% nucleotide identity with a reference nucleic acid sequence encompasses nucleic acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding a NADH oxidase may be nucleic acid(s) encoding an amino acid sequence selected from the group consisting of sequences having at least 78%, preferably at least 80%, identity with sequences SEQ ID NO: 22, 24, 26 and 28.

As described herein, an amino acid sequence having at least 78% amino acid identity with a reference amino acid sequence encompasses amino acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of NADH oxidase in the present invention is regulated by at least one promoter and at least one terminator, such as herein after defined more in details, which are respectively present in 5'- and -3' position of the nucleic acid sequence encoding the NADH oxidase.

In addition, the above-mentioned advantageous technical effects are linked to the expression level of said NADH oxidase. Indeed, and as it emerges from the herein after examples, not only the mere presence of a NADH oxidase is important but the level of NADH oxidase expression has also an extreme importance on 2,3-BDO production.

As above-mentioned, a recombinant yeast according to the invention has a reduced pyruvate decarboxylase activity, and in the genome of which has been inserted, notably, one or more copies of a nucleic acid encoding a NADH oxidase or NOXE.

In this regard, a recombinant yeast according to the invention may comprise notably from 1 to 20 copies of a nucleic acid encoding a NADH oxidase.

Preferably, a recombinant yeast according to the invention may comprise from 1 to 12, in particular from 2 to 5, preferably from 3 to 4, and better still equal to 3, copies of a nucleic acid encoding a NADH oxidase.

According to a particular embodiment, the DNA construct(s) of formulae (I) to (IV) comprising at least the NOXE gene(s) may be inserted in the endogenous URA3 gene of said recombinant yeast.

In view of the above, each of nucleic acids encoding acetolactate synthase, acetolactate decarboxylase, butanediol dehydrogenase and NADH oxidase is under the control of a promoter and of a terminator so as to avoid unwanted regulation, notably such as herein after defined.

Promoter

For obvious reasons, each of nucleic acids encoding acetolactate synthase, acetolactate decarboxylase, butanediol dehydrogenase and NADH oxidase is under the control of a promoter, identical or different.

Said promoters, identical or different, allowing the constitutive over-expression of a given gene, may be found in literature (velculescu et al (1997) Cell 88, 243-251).

Promoters more particularly interesting in the present invention may be selected from the group comprising:
- pADH1 from gene coding for the alcool deshydrogenase (ADH1 gene=Sequence SEQ ID NO: 32),
- pTDH3 from gene coding for the Glyceraldehyde-3-phosphate dehydrogenase (TDH3 gene=Sequence SEQ ID NO: 39),
- pTEF2.K1 from the gene coding for the Translational elongation factor EF-1 alpha (TEF2 gene=Sequence SEQ ID NO: 30).
- pGPM1 from the gene coding for Glycerate Phospho-Mutase (GPM1 gene=Sequence SEQ ID NO: 33),
- pPDC1 from the gene coding for pyruvate decarboxylase (PDC 1 gene=Sequence SEQ ID NO: 35),
- pENO2 from the gene coding for Enolase II (ENO2 gene=Sequence SEQ ID NO: 29),
- pTEF3 from the gene coding for the Gamma subunit of translational elongation factor eEF1B (TEF3 gene=Sequence SEQ ID NO: 31),
- pFBA1 from the gene encoding for the Fructose 1,6-bisphosphate aldolase II (FBA1 gene=Sequence SEQ ID NO: 34).
- pPGK1 from the gene encoding for the 3-phosphoglycerate kinase (PGK1 gene=Sequence SEQ ID NO: 36),
- pPYK1 from the gene encoding for the pyruvate kinase (PYK1 gene=Sequence SEQ ID NO: 49),
- pTP1 from the gene encoding for the Triose Phosphate Isomerase (TP11 gene=Sequence SEQ ID NO: 50), or
- pTEF1 from the gene coding for the Translational elongation factor EF-1 alpha (TEF1 gene=Sequence SEQ ID NO: 38).

In addition, homologous promoters from other closely related yeasts can also be used as promoters form other yeast form the *Saccharomyces* genus, or yeast from other genus such as *Candida, Debaryomyces, Pichia* or *Kluveromyces*.

Synthetic promoters as described in Blazeck & Alper (2013) Biotechnol. J. 8 46-58 can also be used.

More particularly, said promoters, identical or different, may be preferably characterized by a sequence of nucleic acid selected from the group consisting of sequences having at least 80% nucleic acid identity with the nucleic acid sequences SEQ ID NO: 29 to 39, 49 and 50.

Terminator

For obvious reasons, each of nucleic acids encoding acetolactate synthase, acetolactate decarboxylase, butanediol dehydrogenase and NADH oxidase is linked to a transcription terminator (which may be also termed "terminator" herein), identical or different.

Said transcription terminators, identical or different, may be found in literature Yamanishi et al., (2013) ACS synthetic biology 2, 337-347.

Terminators more particularly interesting in the present invention may be selected from the group comprising:
- tTP11 from the gene encoding for the Triose Phosphate Isomerase (TP11 gene=Sequence SEQ ID NO: 44),
- tMET25 from the gene encoding for the O-acetyl homoserine-O-acetyl serine sulfhydrylase (Met25 gene=Sequence SEQ ID NO: 45),
- tADH1 from gene coding for the alcool deshydrogenase (ADH1 gene=Sequence SEQ ID NO: 43),
- tENO2 from the gene coding for Enolase II (ENO2 gene=Sequence SEQ ID NO: 46),
- tTDH2 from the gene coding for Glyceraldehyde-3-phosphate dehydrogenase, isozyme 2 (TDH2 gene=Sequence SEQ ID NO: 40),
- tPGK1 from the gene encoding for the 3-phosphoglycerate kinase (PGK1 gene=Sequence SEQ ID NO: 48),
- tCYC1 (=Sequence SEQ ID NO: 41),
- tMET3 (=Sequence SEQ ID NO: 47),
- tTDH3 (=Sequence SEQ ID NO: 42), and
- tDIT1 (=Sequence SEQ ID NO: 51).

More particularly, said terminator, identical or different, may be preferably characterized by a sequence of nucleic acid selected from the group consisting of sequences having at least 80% identity with sequences SEQ ID NO: 40 to 48 and 51.

According to a particular embodiment, each of nucleic acids encoding acetolactate synthase, acetolactate decarboxylase, butanediol dehydrogenase, and NADH oxidase is under the control of a transcription terminator, identical or different, said transcription terminators being characterized by a sequence of nucleic acid selected from the group consisting of sequences having at least 80% nucleic acid identity with the nucleic acid sequence of SEQ ID NO: 40 to 48.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus *Saccharomyces, CandidaAshbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* or *Malassezia*.

More preferably, the yeast may be Crabtree positive yeast of genus of *Saccharomyces, Dekkera, Schizosaccharomyces, Kluyveromyces, Torulaspora Zigosaccharomyces, or. Brettanomycces*

More preferably, the yeast may be from the species Saccharomyces cerevisiae, Saccharomyces boulardii, Saccharomyces douglasii, Saccharomyces bayanus or.or *Zigosaccharomyces bailii, Schizosaccharomyces pombe, Dekkera brucelensis, Dekkera intermedia, Brettanomnycces custersii, Brettanomycces intermedius, Kluyveromyces themotolerens, Torulaspora globosa, Torulaspora glabrata*

As above-mentioned, a recombinant yeast according to the invention preferably has a pyruvate decarboxylase activity which is reduced by insertion of at least one DNA construct(s) selected from the group comprising formulae (I) to (IV), and preferably of at least one of said DNA construct(s) comprising only at least one nucleic acid(s) encoding ALS, ALD and/or BDH.

According to a preferred embodiment, the recombinant yeast may be a recombinant *Saccharomyces cerevisiae* and the pyruvate decarboxylase activity is reduced by disruption of only two pdc genes.

More preferably, the disrupted pdc gene(s) may be selected from the group consisting of pdc1, pdc5, pdc6 and a mixture thereof, and preferably of pdc1 and pdc6.

Methods implemented to insert a specific DNA construct within a gene, and more particularly a pyruvate decarboxylase gene, belong to the general knowledge of a man skilled in the art. A related method is described in more details in the herein after examples.

Most Preferred Embodiments

Advantageously, the nucleic acids encoding enzymes implemented in the present invention are advantageously chosen among ALS.Bs, ALS.Pp, ALD.L1, ALD.Ea, BDH.Ea, BDH.Sc, NOXSpn, NOXE.L1 and a mixture thereof.

According to a preferred embodiment, a recombinant yeast according to the present invention may be characterized in that it belongs to the *Saccharomyces* genus, in particular *Saccharomyces cerevisiae* species, wherein the endogenous pyruvate decarboxylase activity is reduced by disruption of at least two of pdc genes, in particular by disruption of pdc 1 and pdc 6 genes, wherein:

one of pdc genes, preferably the pdc 1 gene, is disrupted by insertion of a DNA construct of the formula (IIe) below:

$$5'\text{-}[(\text{prom5})_{y1}\text{-}ALS.Bs\text{-term5}]_{x5}\text{-}[\text{prom1-}ALS.Bs\text{-}\\\text{term1}]_{x1}\text{-}[\text{prom2-}ALD.L1\text{-term2}]_{x2}\text{-}[\text{prom3-}BD\text{-}\\H.Ea\text{-}(\text{term3})_{z1}]_{x3}\text{-}3' \quad (\text{IIe}),\text{ and}$$

the at least other pdc gene, distinct from the above-mentioned disrupted pdc gene, and preferably the pdc 6 gene, is disrupted by insertion of a DNA construct of the formula (IIf) below:

$$5'\text{-}[(\text{prom5})_{y1}\text{-}ALS.Pp\text{-term5}]_{x5}\text{-}[\text{prom1-}ALS.Pp\text{-}\\\text{term1}]_{x1}\text{-}[\text{prom2-}ALD.Ea\text{-term2}]_{x2}\text{-}[\text{prom3-}\\BDH.Sc\text{-}(\text{term3})_{z1}]_{x3}\text{-}3' \quad (\text{IIf}),$$

and wherein the DNA construct of following formula (IIf"):

$$5'\text{-}[(\text{prom4})_{y2}\text{-}NOXE.Spn\text{-}(\text{term4})_{z2}]_{x4}\text{-}3' \quad (\text{IIf"}),$$

is inserted in the URA3 gene,
wherein:
prom1, prom2, prom3, prom4, prom5, term1, term2, term3, term4, term5, "y1", "y2", "z1" and "z2" are such as above-defined and ALS.Bs, ALS.Pp, ALD.L1, ALD.Ea, BDH.Ea, BDH.Sc and NOXE.Spn, NOXE.L1 are such as defined in hereinafter Table 1,
each of "x1", "x2" and "x3", independently the ones of the others, represents an integer ranging from 0 to 50, preferably from 0 to 20, preferably from 0 to 10, more particularly from 0 to 3, and in particular equal to 1;
"x4" represents an integer ranging from 0 to 50, preferably from 0 to 20, preferably from 0 to 12, more particularly from 2 to 5, preferably from 3 to 4, and better still equal to 3,
provided that said recombinant yeast comprises at least one nucleic acid encoding for each ALS, ALD, BDH and NOXE, and more particularly provided that each DNA construct of formula (IIe) and (IIf) comprises each at least one nucleic acid encoding for each ALS, ALD and BDH.

In view of the above, and although it is implicitly disclosed, it is specifies that, between each formulae (IIe) and (IIf):

"x1" to "x3", "x5", "y1", "y2", "z1" and "z2"; and/or
the promoter and/or terminator for each copy of nucleic acid for a considered gene,
may be identical or different.

According to a particular preferred embodiment, a recombinant yeast according to the present invention may be characterized in that it belongs to the *Saccharomyces* genus, in particular *Saccharomyces cerevisiae* species, wherein the endogenous pyruvate decarboxylase activity is reduced by disruption of at least two of pdc genes, in particular by disruption of pdc 1 and pdc 6 genes, wherein:

one of pdc genes, preferably the pdc 1 gene, is disrupted by insertion of a DNA construct of the formula (IIg) below:

$$5'\text{-}[ALS.Bs\text{-}tTDH2]_1\text{-}[pENO2\text{-}ALD.L1\text{-}tCYC1]_1\text{-}\\ [pTEF3\text{-}BDH.Ea\text{-}tTDH3]_1\text{-}3' \quad (\text{IIg}),$$

the at least other pdc gene, distinct from the above-mentioned disrupted pdc gene, and preferably the pdc 6 gene, is disrupted by insertion of a DNA construct of the formula (IIh') below:

$$5'\text{-}[pADH1\text{-}ALS.Pp\text{-}tDPI1]_1\text{-}[pTDH3\text{-}ALD.Ea\text{-}\\tMET25]_1\text{-}[pGMP1\text{-}BDH.Sc\text{-}tENO2]_1\text{-}3'$$

and wherein the DNA construct of following formula (IIh"):

$$5'\text{-}[pENO2\text{-}NOXE.Spn\text{-}tPGK1]\text{-}3' \quad (\text{IIh"})$$

is inserted in the URA3 gene,
wherein:
the "ALS.Bs" gene of DNA construct of formula (IIg) is under the control of the promoter of the pdc gene in which said DNA construct of formula (IIg) is inserted,
pENO2, pTEF3, pADH1, pTDH3, pGMP1, tTDH2, tCYC1, tTDH3, tDPI1, tMET25, tENO2 and tPGK1 are such as defined in the present description and more particularly in the hereinafter sequences listing,
ALS.Bs, ALS.Pp, ALD.L1, ALD.Ea, BDH.Ea, BDH.Sc and NOXE.Spn, NOXE.L1 are such as defined in hereinafter table 1 and mode particularly in the hereinafter sequences listing.

Optimisation of 2,3-Butanediol Production
According to a particular embodiment, the recombinant yeast according to the invention may be further modified to optimize 2,3-butanediol production.

Use of Alternate Sources of Sugar:
The direct use of alternate source of sugar such as starch her requires the over expression in yeast of exogenous α-amylase and glucoamylase (Buscke et al. biosource technology 2013).

Sugar Import—Improvement of C5 Sugar Import:
The import of pentoses by recombinant microorganism is a major issue for industrial process since C5 sugars are major constituents of hydrolysed lignocellulosic biomass. Native strains of *S. cerevisiae*, like many other types of yeast, are unable to utilize either xylose or arabinose as fermentative substrates (Hahn-Hagerdal et al., 2007; Jin et al., 2004). Interestingly, it is able to uptake xylose even though the sugar is not a natural substrate (Hamacher et al., 2002).

*S. cerevisiae* GAL2, HXT1, HXT2, HXT4, HXT5, and HXT7 catalyze the uptake of xylose because they have a broad substrate specificity (Hamacher et al., 2002; Saloheimo et al., 2007; Sedlak & Ho 2004). However, their affinity for xylose is much lower than that for glucose and the xylose uptake by the transporters is strongly inhibited by glucose (Saloheimo et al., 2007).

Several changes are needed to obtain a strain able to grow and consume xylose and/or arabinose. These different modifications are a part of the invention.

Overexpression of Heterologous Xylose Transporters:
In order to improve the xylose and arabinose uptake, the recombinant 2,3-BDO producer strain has to be modified to express heterologous genes coding for xylose or arabinose transporters. For example, genes GXF1, SUT1 and AT5g59250 from *Candida intermedia, Pichia stipitis* and *Arabidopsis thaliana*, respectively, are overexpressed to improve xylose utilization by the yeast (Runquist et al., 2010).

Overexpression of Pathways Involved in the Metabolism of Xylose and Arabinose:

Yeast strains are able to take up xylose even though the sugar is not a natural substrate. Even though genes for xylose assimilation are present in *S. cerevisiae* they are not expressed at a sufficient level to enable significant sugar assimilation. Thus genetic modifications are necessary to improve the assimilation of pentose sugars. All enzymes that allow the transformation of xylose or arabinose to xylitol need to be enhanced as well as the enzymes which convert xylitol in xylulose, and xylulose into xylulose-5-phosphate. Either, the homologous genes from the xylose and arabinose pathways have to be overexpressed or heterologous genes from bacteria have to be overexpressed.

In one embodiment of the invention, the xylose uptake and its assimilation by the strain are improved by overexpressing for example:

1) Genes XYL1 or GRE3 coding the aldolase reductase of *P. stipitis* and *S. cerevisiae*, respectively, associated to overexpression of XYL2 encoding the xylitol dehydrogenase from *P. stipitis*, combined with the overexpression of genes XKS 1 or XYL3 encoding the xylulokinase from *S. cerevisiae* and *P. stipitis*, respectively, 2) The gene xylA encoding a xylose isomerase from bacteria or *Piromyces* associated to the overexpression of genes XKS1 or XYL3 encoding the xylulokinase from *S. cerevisiae* and *P. stipitis*, respectively.

In another embodiment of the invention, arabinose uptake and its assimilation by the strain are improved by overexpressing for example:

1) Homologous genes XYL1 or GRE3 coding the aldolase reductase of *P. stipitis* and *S. cerevisiae*, respectively, associated to lad1 encoding the L-arabinitol 4-hydrogenase and Ixr1 encoding a L-xylulose reductase from *Trichoderma reesei*, in combination with the overexpression of XYL2 encoding the xylitol dehydrogenase from *P. stipitis*, and in addition the overexpression of genes XKS1 or XYL 3 encoding the xylulokinase from *S. cerevisiae* and *P. stipitis*, respectively, 2) Heterologous genes araA and araB encoding bacterial arabinose isomerase and ribulose kinase.

Optimization of the Pentose Phosphate Pathway:

This can be done by overexpressing at least one gene belonging to the non oxidative pentose phosphate pathway; TAL1, TKL1, RKL1 and RPE1 from the yeast strain.

Optimization of the availability of NAPDH cofactors required by the enzymes involved in the metabolism of C5-sugars This is attained by expressing the transhydrogenases of *E. coli* in the yeast strain. The genes udhA and or pntAB from *E. coli* will be overexpressed in the producer strain.

Prevention of the Glucose Consumption Towards Glycerol Synthesis:

This can be done by disruptiong the GPD1 gene encoding the glycerol-3-phosphate dehydrogenase EC 1.1.1.8. (GPDH).

The present invention according to this embodiment is interesting notably in view of the yield in 2,3-BDO despite the fact that the disruption of the GPD1 gene leads to removing an enzyme activity which consumes NADH in favor of NAD. To counterbalance the redox disequilibrium thus generated, GPD1 disrupted strain may require additional expression of NOXE.

According to a particular embodiment, a recombinant strain according to the present invention is such that it does not comprise any genetic modification(s) which has the effect of reducing the glucose repression, as disclosed in WO 2011/041426 or Kim et al. (Bioresource Technology, vol. 146, 2013: 274).

According to a particular embodiment, a recombinant strain according to the present invention is such that it does not comprise any genetic modification(s) for allowing expressing any xylose assimilation pathways, as disclosed in Kim et al. (Journal of Biotechnology, 2014.

Culture Conditions

The present invention also relates to the use of a recombinant yeast such as above-defined, for the production of 2,3-butanediol (BDO) and/or direct derivatives thereof, in particular said direct derivatives of 2,3-butanediol (BDO) being selected from the group consisting of butane-diene (BDE), Methyl-Ethyl-Ketone (MEK) or a mixture thereof.

The present invention further relates to a method of production of 2,3-butanediol (BDO) comprising the following steps:

providing a recombinant microorganism as previously described, cultivating the recombinant microorganism in a culture medium containing a source of carbon, and recovering the 2,3-butanediol.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

Purification of 2,3-Butanediol

According to a specific aspect of the invention, the fermentative production of 2,3-butanediol comprises a step of isolation of the 2,3-butanediol from the culture medium. Recovering the 2,3-butanediol from the culture medium is a routine task for a man skilled in the art. It may be achieved by a number of techniques well known in the art including but not limiting to distillation, gas-stripping, pervaporation or liquid extraction. The expert in the field knows how to adapt parameters of each technique dependant on the characteristics of the material to be separated.

The yeast as model of microorganism in the present invention has been retained in that the synthesized 2,3-BDO is entirely exported outside the cells, thus simplifying the purification process.

The synthesized 2,3-BDO may be collected by distillation. Distillation may involve an optional component different from the culture medium in order to facilitate the isolation of 2,3-butanediol by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane, dodecane.

The purification conditions may be specifically adapted to the downstream transformation of 2,3-BDO to Methyl Ethyl Ketone and/or 1,3-butadiene, including keeping several co-products in the partially purified 2,3-BDO.

Throughout the description, including the claims, the expression "comprising a" should be understood as being synonymous with "comprising at least one", unless otherwise specified.

In addition, the expression "formulae (I) to (IV), according to the considered context and unless contrary indications, means a DNA construct of formulae (I), (II), (III) and (IV) but also (IIa), (IIb), (IIc), (IId), (IIe), (IIf'), (IIf"), (IIg), (IIh') and/or (IIh").

The terms "between . . . and . . . " and "ranging from . . . to . . . " should be understood as being inclusive of the limits, unless otherwise specified.

The examples and FIGURES which follow are presented by way of illustration and without implied limitation of the invention.

EXAMPLES a) Protocol for Making a Recombinant *Saccharomyces cerevisiae* Strain According to the Invention All the hereinafter implemented recombinant *Saccharomyces cerevisiae* strains were constructed from the standard strain W303 (Thomas and Rothstein (1989), Cell. 56, 619-630) using standard yeast molecular genetics procedure (Methods in yeast Genetics—A cold spring harbor laboratory course Manual (2000) by D. Burke, D. Dawson, T. Steams CSHL Press).

In these strains, pyruvate decarboxylase activity is reduced by disruption of at least one of the pdc genes (pdc1, pdc5, pdc6) or by replacement of their cognate transcription promoter by a weak promoter.

In the most efficient strains, only pdc1 and pdc6 were deleted.

A variety of exogenous enzymes were expressed in the considered recombinant *Saccharomyces cerevisiae* strains. They were chosen according to their Michaelis Menten enzymatic parameters when available (see herein after table 1). High kcat for high efficiency, and variety of Km to cover different concentration in substrate. *Paenibacillus polymyxa* enzymes were chosen because this organism is a natural 2,3-BDO producer.

The genes nomenclature relatives to the implemented exogenous enzymes acetolactate synthase, acetolactate decarboxylase, butanediol dehydrogenase and water forming NADH oxydase is displayed in the hereinafter Table 1.

These genes are designated by the acronym of the enzyme followed by the acronym of the organism of origin as follows:

TABLE 1

| Enzyme | Gene | Organism | Km (mM) | kcat (s$^{-1}$) | Accession number |
|---|---|---|---|---|---|
| Acetolactate synthase E.C.2.2.1.6 (ALS) | ALS.Bs | Bacillus subtilis | 13 | 121 | YP008831756.1 |
| | ALS.Nt | Nicotiana tabacum | 11-16 | 3 | P09114.1 |
| | ALS.Pp | Paenibacillus polymyxa | — | — | YP003869749.1 |
| Acetolactate decarboxylase E.C.4.4.4.5 (ALD) | ALD.Bb | Brevibacillus brevis | 0.06 | — | YP002775372.1 |
| | ALD.Ea | Enterobacter cloacae | 10-13 | — | YP006476615.1 |
| | ALD.Ll | Lactococcus lactis | 10 | — | NP267263.1 |
| Butanediol dehydrogenase E.C.1.1.1.4 (BDH) | BDH.Ea | Enterobacter aerogenes | 0.4 | — | YP004593688.1 |
| | BDH.Pp | Paenibacillus polymyxa | 0.5 | — | WP016821825.1 |
| | BDH.Ko | Klebsiella oxycota | — | — | ACT82245.1 |
| | BDH1.Sc | Saccharomyces Cerevisiae | 4.5 | — | NP009341.2 |
| Water forming NADH Oxydase (NOX) | NOXE.Ll | Lactococcus lactis | | | YP003352913.1 |
| | NOXE.Spn | Streptococcus pneumoniae | | | YP002742271.1 |
| | NOXE.Ef | Enterococcus faecalis | | | NP815302.1 |
| | NOXE.Lb | Lactobacillus brevis | | | WP021742768.1 |

In addition, for a better comprehension of following genotypes:

ade2, his3, leu2, trp1 and ura3 are auxotrophy marker genes.

Lowercase letters mean that the considered gene is inactive, uppercase letters reflect an active gene.

"::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.

"gene.K1" means that the gene originates from *Kluyveromyces lactis*.

Transcription Promoters allowing the constitutive overexpression of a given gene are found in literature (Velculescu et al. (1997) Cell 88, 243-251). Promoters herein used are designated by "p" followed by their cognate gene name. Their respective sequence number is also hereinafter mentioned.

Transcription terminators are also placed after each gene. To avoid unwanted regulation promoters and terminators framing one inserted gene were not taken from the same original gene. The terminators herein used are designated by "t" followed by their cognate gene name. Their respective sequence number is also hereinafter mentioned.

Cluster of above-mentioned genes were integrated in recombinant yeast at once using the ability of yeast to efficiently recombine free DNA ends which have sequence homology.

Recombinant yeast were obtained according to published methods available to the man of the art. Notably, it may be followed the method described in Shao et al. (Nucleic Acids Research, 2009, Vol. 37, No. 2: e16) and Shao et al. (Methods in Enzymology, 2012 Elsevier Inc., Vol. 517: 203), eventually with only minor variation.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. One of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

b) Regarding the ALS and ALD Enzymes

ALS and ALD enzymes were not evaluated individually, but in pairs (ALS+ALD) through the yield of acetoin. Three exogenous ALD and ALS were chosen according to their kinetic parameters: ALS.Nt, ALS.Pp, ALS.Bs and ALD.Bb, ALD.Ll, ALD.Ea (see above).

Eight of the nine possible combinations of ALS and ALD were conjointly inserted on the chromosome of a ura3-yeast strain behind promoters and followed by one terminator.

The insertion of these two genes disrupts the pdc1 gene. The URA3 marker gene is concomitantly inserted to select the transformant. ALS/ALD combination were inserted in strain YA747, namely a W303 derivative having the following genotype:

YA747: MAT-a, ade2, bdh1::TRP1.K1, his3, leu2, pdc1:: HIS5.Sp, pdc6::LEU2.K1, trp1, ura3.

The following strains were constructed:

YA768: MAT-a, ade2, bdh1::TRP1.K1, his3, leu2, pdc1::[-ALS.Bs-tTPI1, pTDH3-ALD.Ea-tMET25, URA3.K1], pdc6::LEU2.K1, trp1, ura3

NB: in this case, the gene "ALS.Bs" is under the control of the natural promoter of pdc1, namely the promoter pPDC1.

YA769: MAT-a, ade2, bdh1::TRP1.K1, his3, leu2, pdc1::[-ALS.Nt-tTPI1, pTDH3-ALD.Ea-tMET25, URA3.K1], pdc6::LEU2.K1, trp1, ura3

YA770: MAT-a, ade2, bdh1::TRP1.K1, his3, leu2, pdc1::[-ALS.Pp-tTPI1, pTDH3-ALD.Ea-tMET25, URA3.K1], pdc6::LEU2.K1, trp1, ura3

YA771: MAT-a, ade2, bdh1::TRP1.K1, his3, leu2, pdc1::[-ALS.Nt-tTPI1, pTDH3-ALD.Bb-tMET25, URA3.K1], pdc6::LEU2.K1, trp1, ura3

YA772: MAT-a, ade2, bdh1::TRP1.K1, his3, leu2, pdc1::[-ALS.Nt-tTPI1, pTDH3-ALD.L1-tMET25, URA3.K1], pdc6::LEU2.K1, trp1, ura3

YA773: MAT-a, ade2, bdh1::TRP1.K1, his3, leu2, pdc1::[-ALS.Pp-tTPI1, pTDH3-ALD.L1-tMET25, URA3.K1], pdc6::LEU2.K1, trp1, ura3

YA810: MAT-a, ade2, bdh1::TRP1.K1, his3, leu2, pdc1::[-ALS.Bs-tTPI1, pTDH3-ALD.Bb-tMET25, URA3.K1], pdc6::LEU2.K1, trp1, ura3

YA811: MAT-a, ade2, bdh1::TRP1.K1, his3, leu2, pdc1::[-ALS.Pp-tTPI1, pTDH3-ALD.Bb-tMET25, URA3.K1], pdc6::LEU2.K1, trp1, ura3

All these strains were grown for 24 hours in 8% glucose YPA (Yeast Extract 1%, Bacto peptone 2%, adenine 0.1 mM, glucose 8%). They were harvested and acetoin, ethanol and 2,3-BDO content was determined according to standard methods with specificity adapted from in Gonzales et al. (2010), Applied and environmental Microbiology 76 670-679.

For some strains, several clones were assayed, the last number after the "-" is the clone number. Note that as the endogenous bdh enzyme is disrupted, no 2,3-BDO is produced.

The ethanol, acetoin and 2,3-BDO production are monitored following standard methods and Gonzales et al. (2010), Applied and environmental Microbiology 76 670-679.

Results

Table 2 hereinafter displays the acetoin production of the above-mentioned tested strains.

TABLE 2

| Strains | Ethanol (g/l) | Acetoin (g/l) | 2,3-BDO (g/l) | ALS | ALD |
|---|---|---|---|---|---|
| YA747-8 | 32.2 | 0.2 | 0.03 | | |
| YA772-6 | 31.4 | 0.6 | 0.02 | Nt | L1 |
| YA772-10 | 29.5 | 1.2 | 0.03 | Nt | L1 |
| YA773-3 | 31.8 | 0.2 | 0.02 | Pp | L1 |
| YA810-1 | 32.3 | 0.2 | 0.02 | Bs | Bb |
| YA768-4 | 31.1 | 1.0 | 0.09 | Bs | Ea |
| YA768-7 | 31.0 | 2.1 | 0.16 | Bs | Ea |
| YA770-6 | 25.5 | 4.85 | 0.25 | Pp | Ea |
| YA770-12 | 21.8 | 6.7 | 0.27 | Pp | Ea |
| YA811-4 | 19.8 | 6 | 0.22 | Pp | Bb |
| YA811-5 | 21.15 | 5.75 | 0.22 | Pp | Bb |
| YA771-5 | 20.6 | 5.5 | 0.16 | Nt | Bb |
| YA769-1 | 22.25 | 6.05 | 0.23 | Nt | Ea |
| YA769-8 | 25.65 | 4.4 | 0.21 | Nt | Ea |

From these results, it may be conclude that, taken separately, the best enzymes to enhance acetoin production are ALS Pp, ALS Nt, ALD Ea and ALD Bb which indeed appears as being the most efficient enzyme. Most combination of ALS and ALD couples have been assayed in strains also overexpressing BDH. These strains were first ranked on their growth on glucose. Then two of the fastest growing strains were assayed for butanediol production, namely:

YA538-5C: MAT-a, his3, leu2, pdc1::[-ALS.Bs-tTDH2, pENO2-ALD.L1-tCYC1, pTEF3-BDH.Ea-tTDH3, URA3.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3

YA 919-19: MAT-a, his3, leu2, pdc1::[-ALD.Bb-tPGK1, pTEF3-BDH.Ea-tTDH3, pENO2-ALS.Nt-tCYC1, LEU2.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3

Both clones were grown for 48 hours in YPA glucose 16% in a 250 ml baffled flask under vigorous agitation at 28° C. Samples were harvested at 24 h, 32 h and 48 h. Ethanol, acetoin and butanediol content in the lysate were assayed, according to the same protocols as above-referenced.

Results

Table 3 hereinafter displays these ethanol, acetoin and 2,3-BDO contents in 16% glucose YPA.

TABLE 3

| Strain | Time (Hour) | Optical density | Ethanol (g/l) | Acetoin (g/l) | RR 2,3-BDO (g/l) | MESO 2,3-BDO (g/l) | RR + MESO (g/l) |
|---|---|---|---|---|---|---|---|
| YA538-5C | 24 | 25.7 | 3.6 | 0.94 | 26.20 | 6.80 | 33.00 |
| | 32 | 37.7 | 5.2 | 1.59 | 35.23 | 11.52 | 46.75 |
| | 48 | 42.0 | 4.3 | 8.31 | 29.57 | 14.62 | 44.19 |
| YA919-16 | 24 | 35.2 | 26.3 | 0.28 | 5.29 | 4.95 | 10.24 |
| | 32 | 43.8 | 42.4 | 0.15 | 5.53 | 6.38 | 11.92 |
| | 48 | 42.3 | 44.7 | 3.65 | 4.83 | 5.77 | 10.59 |

From these results, it is concluded that overexpression of two ALS and two ALD significantly increases 2,3-BDO (and therefore transiently acetoin) production as compare to only one ALS and one ALD (see results in table 3 vs table 2).

The best combination is ALS.Bs, ALS.Pp, ALD.Bb and ALD.Ea, although ALS.Bs and ALD.Bb do not support a strong acetoin production on their own.

c) Determination of the Most Efficient BDH Enzymes

Four exogenous enzymes were overexpressed using the pTEF1 promoter in a yeast strain in which the endogenous BDH1 enzyme has been inactivated. The BDH activity present in the different cell lysates was assayed and compare to the endogenous activity.

The BDH activity is monitored following the appearance of NADH through the absorbance at 340 nm, following the protocol described in Gao et al., (2012) journal of basic microbiology 52, 1-9.

Results

Table 4 hereinafter displays the BDH activity.

TABLE 4

| Strain | Genotype | Activity (nmol/mg/min) |
|---|---|---|
| CC788-2B | BDH.Sc | 276 ± 55 |
| pAL06 | bdh1::LEU2 + empty vector (pRS 316) | Not Detected |
| pAD320 | bdh1::LEU2 + pRS316-pTEF1-BDH.Ea-tADH1 | 763 ± 41 |

Enzymes from *Saccharomyces cerevisiae* (Sc) and from *Enterobacter aerogenes* (Ea) thus appears efficient.

d) The Advantageous Technical Effect of the NOXE Enzyme on the 2,3-BDO Yield

Three copies of pENO2-NOXE.Spn-tPGK1 were inserted in the above-mentioned strain YA538-5C, thus yielding the strain YA724-2. The two strains were compared for their respective 2,3-BDO production:

YA538-5C: MAT-a, his3, leu2, pdc1::[-ALS.Bs-tTDH2, pENO2-ALD.L1-tCYC1, pTEF3-BDH.Ea-tTDH3, URA3.K1-], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3

YA724-2: MAT-a, his3, leu2, pdc1::[-ALS.Bs-tTDH2, pENO2-ALD.L1-tCYC1, pTEF3-BDH.Ea-tTDH3, LEU2.K1-], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3::[pENO2-NOXE.Spn-URA3K1-tPGK1]×3

YA538-5C and YA724-2 were grown in YPA 24% glucose. Aliquots were taken along the culture, and ethanol, acetoin and BDO and glucose contents in the culture were assayed according to standard procedure.

Ethanol, acetoin and butanediol content were assayed according to the same protocols as above-referenced.

The glucose consumption is also monitored following standard methods and Gonzales et al. (2010), Applied and environmental Microbiology 76 670-679.

Results

Results are reported in tables 5a and 5b hereinafter.

TABLE 5a

| Strain | Glucose (%) | Time (Hour) | Optical density | Ethanol (g/l) | Acetoin (g/l) | 2,3-BDO (g/l) | Glucose |
|---|---|---|---|---|---|---|---|
| YA538-5C | 24% | 4 | 1.8 | 0.0 | 0.3 | 0.4 | 250.4 |
|  |  | 8 | 2.8 | 0.2 | 0.7 | 1.7 | 246.5 |
|  |  | 24 | 21.5 | 0.5 | 0.9 | 33.6 | 156.0 |
|  |  | 32 | 34.8 | 0.9 | 0.8 | 69.9 | 63.7 |
|  |  | 48 | 44.2 | 0.8 | 5.1 | 90.6 | ND* |
|  |  | 52 | 46.7 | 0.5 | 7.6 | 89.0 | ND* |

*ND: Not Detected.

TABLE 5b

| Strain | Glucose (%) | Time (Hour) | Optical density | Ethanol (g/l) | Acetoin (g/l) | 2,3-BDO (g/l) | Glucose |
|---|---|---|---|---|---|---|---|
| YA724-2 | 24% | 8 | 9.7 | 0.4 | 1.6 | 3.4 | 230.0 |
|  |  | 24 | 51.9 | 1.8 | 1.1 | 76.3 | 4.4 |
|  |  | 28 | 54.1 | 2.5 | 0.7 | 92.3 | 1.0 |
|  |  | 32 | 53.9 | 2.5 | 5.3 | 88.1 | 0.01 |
|  |  | 48 | 54.9 | 1.0 | 10.7 | 83.5 | ND* |

*ND: Not Detected

These results show that overexpression of NOXE leads to a faster accumulation of 2,3-BDO than without NOXE. Long culture leads to a oxidation of 2,3-BDO back into acetoin.

NOXE genes from different origin where inserted in the YA388-1C strain, having the following genotype: MAT-a, his3, leu2, pdc1::HIS5.Sp, pdc6::[pADH1-ALS.Pp-tDPI1, pTDH3-ALD.Ea-tMET25,pTEF2.K1-TRP1.Sc-tADH1, pGMP1-BDH.Sc-tENO2], trp1, ura3

YA679-8, YA679-6 and YA 679-4 contains 1, 2 and 12 copies of pENO2-NOXE.L1-tPGK1 respectively.

YA680-2, YA680-3, YA724-2 et YA721-2D contains 1, 2, 3 and 4 copies of pENO2-NOXE.Spn-tPGK1 respectively.

NOXE activity in yeast lysate was determined according to Lopez de Felipe and Hungenholtz (2001) International Diary Journal 11, 37-44.

Results

Results are reported in table 6 hereinafter.

TABLE 6

| Strain | Genotype | NOXE activity (nmol/mg/min) |
|---|---|---|
| YA388-1C | pdc1::HIS5.Sp, pdc6::[ALS.Pp-ALD.Ea-TRP1.Sc-BDH.Sc] | — |
| YA583-1 | pdc1::[ALS.Bs-ALD.Ll-BDH.Ea-URA3.Sc], pdc6::[ALS.Pp-ALD.Bb-NOXE.Ll-BDH.Pp-TRP1.Kl-] | 39 ± 7 |
| YA679-8 | pdc1::HIS5.Sp, pdc6::[ALS.Pp-ALD.Ea-TRP1.Sc-BDH.Sc],ura3::[NOXE.Ll-URA3]x1 | 183 ± 21 |
| YA679-6 | pdc1::HIS5.Sp, pdc6::[ALS.Pp-ALD.Ea-TRP1.Sc-BDH.Sc], ura3::[NOXE.Ll-URA3]x2 | 155 ± 32 |
| YA679-4 | pdc1::HIS5.Sp, pdc6::[ALS.Pp-ALD.Ea-TRP1.Sc-BDH.Sc], ura3::[NOXE.Ll-URA3]x12 | 1764 ± 226 |
| YA719-2 | pdc1::[ALS.Bs-ALD.Ll-BDH.Ea-LEU2.K1], pdc6::[ALS.Pp-ALD.Ea-TRP1.Sc-BDH.Sc],trp1, ura3::[NOXE.Ll-URA3]x12 | 1835 |
| YA680-2 | pdc1::HIS5.Sp, pdc6::[ALS.Pp-ALD.Ea-TRP1.Sc-BDH.Sc], ura3::[NOXE.Spn-URA3]x1 | 443 ± 52 |
| YA680-3 | pdc1::HIS5.Sp, pdc6::[ALS.Pp-ALD.Ea-TRP1.Sc-BDH.Sc], ura3::[NOXE.Spn-URA3]x2 | 473 ± 55 |
| YA724-2 | pdc1::[ALS.Bs-ALD.Ll-BDH.Ea-LEU2.Kl], pdc6::[ALS.Pp-ALD.Ea-TRP1.Sc-BDH.Sc], trp1, ura3:: [NOXE.Spn-URA3]x3 | 360 ± 33 |
| YA721-2D | pdc1::[ALS.Bs-ALD.Ll-BDH.Ea-URA3.Sc], pdc6::[ALS.Pp-ALD.Ea-TRP1.Sc-BDH.Sc],trp1, ura3::[NOXE.Spn-URA3]x4 | 937 ± 150 |

All the NOXE genes display an interesting NOXE activity. However, NOXE.Spn appears more active than NOXE.L1.

In order to optimize 2,3-BDO production, NOXE genes from diverse origin and in different copy numbers were expressed in YA538-5C.

Thus, the followings recombinant strains were obtained.

YA719-2: MAT-a, his3, leu2, pdc1::[-ALS.Bs-tTDH2, pENO2-ALD.L1-tCYC1, pTEF3-BDH.Ea-tTDH3, LEU2.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3::[pENO2-NOXE.L1-tPGK1-URA3]×12

YA721-2D: MAT-a, his3, leu2, pdc1::[-ALS.Bs-tTDH2, pENO2-ALD.L1-tCYC1, pTEF3-BDH.Ea-tTDH3, LEU2.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3::[pENO2-NOXE.Spn-tPGK1-URA3]×4

YA724-2: MAT-a, his3, leu2, pdc1::[-ALS.Bs-tTDH2, pENO2-ALD.L1-tCYC1, pTEF3-BDH.Ea-tTDH3, LEU2.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3::[pENO2-NOXE.Spn-tpGK1-URA3K1]×3

These strains were grown in 1.5 L of YPA 30% glucose in a 3 L fermentator at 30° C. under agitation (800 rpm) a constant oxygenation was maintained by bubbling 0.5 L/min-1 of air. Aliquots were taken at 24, 32, 48, 56 h, ethanol and 2,3-BDO and glucose content in the medium was determined according to standard methods and Gonzales et al. (2010), Applied and environmental Microbiology 76 670-679.

Results

Results are reported in tables 7a, 7b and 7c hereinafter.

TABLE 7a

| Strain | Glucose (%) | Time (Hour) | Optical density | Ethanol (g/l) | 2,3 BDO (g/l) | Glucose (g/l) |
|---|---|---|---|---|---|---|
| YA719-2 | 30% | 24 | 59 | 0.0 | 4.0 | 245 |
|  |  | 32 | 83 | 0.0 | 6.9 | 160 |
|  |  | 48 | 96 | 0.0 | 28.8 | 15 |
|  |  | 56 | 95 | 0.0 | 32.9 | 1.2 |

TABLEs 7b

| Strain | Glucose (%) | Time (Hour) | Optical density | Ethanol (g/l) | 2,3 BDO (g/l) | Glucose (g/l) |
|---|---|---|---|---|---|---|
| YA721-2D | 30% | 24 | 80 | 6.5 | 79.4 | 130 |
|  |  | 32 | 86 | 9.6 | 101.7 | 10 |
|  |  | 48 | 96 | 8.6 | 106.7 | 0.025 |
|  |  | 56 | 89 | 7.9 | 106.9 | 0.014 |

TABLEs 7c

| Strain | Glucose (%) | Time (Hour) | Optical density | Ethanol (g/l) | 2,3 BDO (g/l) | Glucose (g/l) |
|---|---|---|---|---|---|---|
| YA724-2 | 30% | 24 | 71 | 0.8 | 55.5 | 170 |
|  |  | 28 | 90 | 0.9 | 75.0 | 105 |
|  |  | 32 | 95 | 1.0 | 90.3 | 80 |
|  |  | 48 | 86 | 1.1 | 125.9 | 23 |
|  |  | 52 | 89 | 1.1 | 135.5 | 14 |

TABLEs 7c-continued

In conclusion, the level of NOXE expression has an extreme importance on 2,3-BDO production. YA724-2 which expresses less NOXE than the two other strains reaches an optimum. The other strain that express higher levels of NOXE, do not accumulate as much 2,3 BDO. It is further to notice that 135.5 g of 2,3-BDO represents 90% of the optimal theoretical yield (150 g) when starting from 300 g of glucose.

e) Prototrophic Recombinant Strain by Insertion of HIS3 Gene

The above-described strain YA724-2 was rendered prototrophic by insertion of HIS3 gene.

The resulting recombinant strain is called YA1044, and has the following genotype:

YA1044-4: MAT-a, his3::HIS3, leu2, pdc1::[-ALS.Bs-tTDH2, pENO2-ALD.L1-tCYC1, pTEF3-BDH.Ea-tTDH3, LEU2.K1], pdc6::[pADH1-ALS.Pp-tDPI1,pTDH3-ALD.Ea-tMET25,pTEF2.K1-TRP1.Sc-tADH1,pGMP1-BDH.Sc-tENO2], trp1, ura3::[pENO2-NOXE.Spn-tPGK1-URA3K1]×3

This strain was then assayed for 2,3-BDO production in 30% glucose YPA under the same condition than above described.

The ethanol, acetoin and 2,3-BDO production and glucose consumption are monitored following standard methods and Gonzales et al. (2010), Applied and environmental Microbiology 76 670-679.

Results

Results are reported in table 8 hereinafter.

TABLE 8

| Strain | Glucose (%) | Time (Hour) | Optical density | Ethanol (g/l) | Acetoin (g/l) | 2,3 BDO (g/l) | Glucose (g/l) |
|---|---|---|---|---|---|---|---|
| YA1044-4 | 30% | 24 | 71.9 | 2.5 | 6.2 | 79.0 | 130 |
|  |  | 32 | 85.9 | 2.5 | 0.8 | 116.8 | 80 |
|  |  | 48 | 87.1 | 2.0 | 1.1 | 147.9 | 0.40 |
|  |  | 52 | 87.3 | 1.3 | 5.3 | 143.2 | 0.02 |

This strain produces as much as 147.9 g of 2,3-BDO (98% of the theoretical yield starting from 300 g of glucose).

This strain also produces 2,3-BDO efficiently in 30% sucrose YPA (otherwise same conditions than above).

Results are reported in table 9 hereinafter.

TABLE 9

| Strain | Sucrose (%) | Time (Hour) | Optical density | Ethanol (g/l) | Acetoin (g/l) | 2,3 BDO (g/l) | Glucose (g/l) |
|---|---|---|---|---|---|---|---|
| YA1044-4 | 30% | 24 | 142 | 1.6 | 14.7 | 78.6 | 10.0 |
|  |  | 32 | 147 | 1.3 | 23.8 | 103.4 | 6.5 |
|  |  | 48 | 153 | 1.1 | 19.0 | 149.0 | 0.06 |
|  |  | 52 | 159 | 0.2 | 19.8 | 149.4 | 0.001 |

This strain also produces 2,3-BDO efficiently in a corn steep medium f) Attenuation of the pdc 5

A recombinant yeast according YA1044-4 such as above-mentioned but which differs in that the pdc 5 gene is further attenuated has been prepared. The resulting recombinant yeast is called YA1245-1.

YA1245-1: pdc1::[ALS.Bs-ALD.L1-BDH.Ea-LEU2.K1-], pdc5::[HIS5.Sp,pRPLA1-PDC5], pdc6::[ALS.Pp-ALD.Ea-TRP1.Sc-BDH.Sc], trp1, ura3::[NOXE.Spn-URA3]×3

This strain was then assayed for 2,3-BDO production in 30% glucose CSL (Corn Steep Liquor) under the same condition than above described.

The ethanol, acetoin and 2,3-BDO production and glucose consumption are monitored following standard methods and Gonzales et al. (2010), Applied and environmental Microbiology 76 670-679.

Results

Results are reported in table 10 hereinafter.

TABLE 10

| Strain | Glucose CSL (%) | Time (Hour) | Optical density | Ethanol (g/l) | Acetoin (g/l) | 2,3 BDO (g/l) | Glucose (g/l) |
|---|---|---|---|---|---|---|---|
| YA1245-1 | 30% | 24 | 82 | 6.0 | 5.4 | 65.6 | 130 |
| | | 32 | 92 | 8.0 | 14.6 | 77.1 | 75 |
| | | 48 | 100 | 7.2 | 20.2 | 103.3 | 15 |
| | | 56 | 102 | 6.5 | 19.7 | 109.6 | 7 |

This strain also produces 2,3-BDO efficiently in 30% glucose YPA (otherwise same conditions than above).

Results are reported in table 11 hereinafter.

TABLE 11

| Strain | Glucose YPA (%) | Time (Hour) | Optical density | Ethanol (g/l) | Acetoin (g/l) | 2,3 BDO (g/l) | Glucose (g/l) |
|---|---|---|---|---|---|---|---|
| YA1245-1 | 30% | 24 | 67 | 3.0 | 2.0 | 81.7 | 105 |
| | | 32 | 116 | 3.8 | 7.1 | 127.3 | 13.0 |
| | | 48 | 88 | 2.6 | 8.5 | 140.7 | 0.013 |
| | | 56 | 85 | 2.2 | 9.8 | 142.3 | 0 | g) Additional Genetic Modifications

The herein after examples start from the above-mentioned recombinant yeast YA1245-1, namely:

YA1245-1: Mat-a, his3, pdc1::[-ALS.Bs-tTDH2,pENO2-ALD.L1-tCYC1, pTEF3-BDH.Ea-tTDH3-LEU2.K1], pdc5::[HIS5.Sp-RS-pRPLA1-PDC5-], pdc6::[pADH1-ALS.Pp-tDPI1, pTDH3-ALD.Ea-tMET25, pTEF2k1-TRP1.Sc-tADH1, pGMP1-BDH.Sc-tENO2], trp1, ura3::[pENO2-NOXE.Sp-tPGK1, URA3]×3

This strains was grown in 1.5 L of YPA 35% sucrose in a 3 L fermentator at 30° C. under agitation (800 rpm) a constant oxygenation was maintained by bubbling 0.5 L/min-1 of air. Aliquots were taken at 24, 32 and 48 h, ethanol, acetoin and 2,3-BDO content in the medium was determined according to standard methods and Gonzales et al. (2010), Applied and environmental Microbiology 76 670-679.

Results are reported in table 12 hereinafter.

TABLE 12

| Strain | Sucrose (%) | Time (Hour) | Optical density | Ethanol (g/l) | Acetoin (g/l) | 2,3 BDO (g/l) |
|---|---|---|---|---|---|---|
| YA1245-1 | 35% | 24 | 104 | 2.5 | 9.5 | 78.9 |
| | | 32 | 117 | 3.7 | 6.1 | 123.5 |
| | | 48 | 113 | 6.7 | 15.2 | 170.1 |

This yield in 2,3-BDO is 96.6% of the theoretical maximum yield.

These results thus confirm the capacity of a recombinant strain according to the invention to grow and also to efficiently produce 2,3-BDO on sucrose.

Two additional strains YA1898-3 and YA1950-1, derived from the above-displayed recombinant strain YA1245-1, were carried out.

The strain YA1898-3 differs from the strain YA1245-1 in that the LEU2.K1 gene has been excised.

The LEU2.K1 gene relates to the sequences SEQ ID NO: and SEQ ID NO: 56.

YA1898-3: Mat-a, his3, leu2, pdc1::[ALS.Bs-ALD.L1-BDH.Ea-], pdc5::[HIS5.Sp-RS-pRPLA1-PDC5], pdc6::[ALS.Pp-ALD.Ea-TRP1.Sc-BDH.Sc], trp1, ura3::[NOXE.Sp-URA3]×3

The strain YA1953-1 differs from the strain YA1245-1 in that the LEU2.K1 and HIS5 genes have been excised.

YA1953-1: Mat-a, his3, leu2, pdc1::[ALS.Bs-ALD.L1-BDH.Ea-], pdc5::[RS-pRPLA1-PDC5], pdc6::[ALS.Pp-ALD.Ea-TRP1.Sc-BDH.Sc], trp1, ura3::[NOXE.Sp-URA3]×3 g)1) Improving Resistance to Weak Acids in the Culture Medium

The presence of weak acids is known to be a limitation for growth when the strains are grown on cellulose or molasses derived medium. In the following strains, which derived from the above-mentioned strain YA1898-3 or YA1950-1, one or two modifications have been inserted so as to try improving the strains resistance to weak acids in the medium. The modifications consist in the disruption of Jen1 gene or the over-expression of HAA-1 gene.

The nucleic acid sequence and the amino acid sequence of the HAA-1 gene relates to the sequences SEQ ID NO: 53 and SEQ ID NO: 54 respectively.

In YA1950-1, jen1 has been disrupted by LEU2.K1.

YA1950-1: Mat-a, his3, jen1::LEU2.K1-RS, leu2, pdc1::[ALS.Bs-ALD.L1-BDH.Ea], pdc5::[HIS5.Sp-RS-pRPLA1-PDC5], pdc6::[ALS.Pp-ALD.Ea-TRP1.Sc-BDH.Sc], trp1, ura3::[NOXE.Sp-URA3]×3

In the following strains YA1955-11, YA1997-2B and YA2036-1, HAA1 is overexpressed using different terminators. In this regard, the terminator tDIT1 relates to the sequence SEQ ID NO: 51.

YA1955-11: Mat-a, his3, leu2::[LEU2.K1-pTDH3-HAA1-tDIT1], pdc1::[ALS.Bs-ALD.L1-BDH.Ea-], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3

YA1997-2B: Mat-a, his3, leu2::[LEU2.K1-pTDH3-HAA1-tDIT1], pdc1::[ALS.Bs-ALD.L1-BDH.Ea], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3

YA2036-1: Mat-a, his3, leu2::[LEU2.K1-pTDH3-HAA1-tTDH3], pdc1::[ALS.Bs-ALD.L1-BDH.Ea], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3.

In the following strains YA2007-2 and YA2008-13, HAA-1 has been inserted in jlp1 (sulfonate dioxygenase gene) and SAM3 (s-adenosyl permease gene) respectively:

YA2007-2: Mat-a, his3, jlp1::[LEU2.K1-pTDH3-HAA1-tDIT1], leu2, pdc1::[ALS.Bs-ALD.L1-BDH.Ea-], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3

YA2008-13: Mat-a, his3, sam3::[LEU2.K1-pTDH3-HAA1-tDIT1], leu2, pdc1::[ALS.Bs-ALD.L1-BDH.Ea-], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3

In the following strains YA2188-2A, YA2208-1C and YA2208-3C, HAA1 has been inserted in Jen1 which is therefore inactivated:

YA2188-2A: Mat-a, his3, jen1::[LEU2.K1-pTDH3-HAA1-tTDH3], leu2, pdc1::[ALS.Bs-ALD.L1-BDH.Ea-], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3

YA2208-1C: Mat-α, his3, jen1::[LEU2.K1-pTDH3-HAA1-tTDH3], leu2, pdc1::[ALS.Bs-ALD.L1-BDH.Ea-], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3 g)2) Prevention of the Glucose Consumption Towards Glycerol Synthesis

In the following strain YA2153-1 and YA2153-11, derived from the above strain YA1898-3, the glycerol phosphate deshydrogenase gene gdp1 has been inactivated by disruption so as to prevent the glucose consumption towards glycerol synthesis:

YA2153-1: Mat-a, gpd1::LEU2.K1-RS, his3, leu2, pdc1::[ALS.Bs-ALD.L1-BDH.Ea], pdc5::[HIS5.Sp-pRPLA1-PDC5], pdc6::[ALS.Pp-ALD.Ea-TRP1.Sc-BDH.Sc], trp1, ura3::[NOXE.Sp-URA3]×3 g)3) Additional Disruption of a Plurality of Genes

The following strains have the same promoters and terminators than the above-defined strain YA-1245 except otherwise mentioned. A plurality of the genes have been disrupted in using LoxP, which is a short having the sequence SEQ ID NO: 52.

DA385: MAT-a/MAT-α, his3/his3, leu2/leu2, pdc1::[ALS.Bs-ALD.L1-BDH.Ea-LEU2.K1-]/pdc1::[ALS.Bs-ALD.L1-BDH.Ea-LEU2.K1], pdc5::[HIS5.Sp-RS-pRPLA1-PDC5]/pdc5::HIS5.Sp, pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3::[NOXE.Sp-URA3]×3

DA411: MAT-a/MAT-α, ade2/ade2, his3/his3, leu2/leu2, pdc1::loxP/pdc1::[ALS.Bs-ALD.L1-BDH.Ea-LEU2.K1], pdc5::loxP/pdc5::[HIS5.Sp-pRPLA1-PDC5], pdc6::loxP/pdc6::[ALS.Pp-ALD.Ea-TRP1.Sc-BDH.Sc], trp1/trp1, ura3/ura3::[NOXE.Sp-URA3]×3

DA426: MAT-a/AT-α, ADE2/ade2, his3/his3, leu2/leu2, pdc1::[ALS.Bs-ALD.L1-BDH.Ea-LEU2.K1]/pdc1::[ALS.Bs-ALD.L1-BDH.Ea-LEU2.K1], pdc5::[HIS5.Sp-pRPLA1-PDC5]/pdc5::URA3.K1-, pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3

DA510: MAT-a/MAT-α, his3/his3, JEN1/jen1::[LEU2.K1-RS-pTDH3-HAA1-tTDH3], leu2/leu2, pdc1::[ALS.Bs-ALD.L1-BDH.Ea]/pdc1::[ALS.Bs-ALD.L1-BDH.Ea], pdc5::[HIS5.Sp-pRPLA1-PDC5]/pdc5::[HIS5.Sp-RS-pRPLA1-PDC5], pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3::[NOXE.Sp-URA3]×3

DA511: MAT-a/MAT-α, his3/his3, JEN1/jen1::[LEU2.K1-RS-pTDH3-HAA1-tTDH3], leu2/leu2, pdc1::[ALS.Bs-ALD.L1-BDH.Ea]/pdc1::[ALS.Bs-ALD.L1-BDH.Ea-LEU2.K1], pdc5::[HIS5.Sp-RS-pRPLA1-PDC5]/pdc5::HIS5.Sp, pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3::[NOXE.Sp-URA3]×3

DA512: MAT-a/MAT-α, his3/his3, JEN1/jen1::[LEU2.K1-RS-pTDH3-HAA1-tTDH3], leu2/leu2, pdc1::[ALS.Bs-ALD.L1-BDH.Ea]/pdc1::[ALS.Bs-ALD.L1-BDH.Ea-LEU2.K1], pdc5::[HIS5.Sp-RS-pRPLA1-PDC5].pdc5::URA3.K1, pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3

DA540: MAT-a/MAT-α, his3/his3, jen1::[LEU2.K1-RS-pTDH3-HAA1-tTDH3]/jen1::[LEU2.K1-RS-pTDH3-HAA1-tTDH3], leu2/leu2, pdc1::[ALS.Bs-ALD.L1-BDH.Ea-]/pdc1::[ALS.Bs-ALD.L1-BDH.Ea-LEU2.K1], pdc5::[HIS5.Sp-RS-pRPLA1-PDC5]/pdc5::URA3.K1, pdc6::[ALS.Pp-ALD.Ea-TRP1.Sc-BDH.Sc]/pdc6::[ALS.Pp-ALD.Ea-TRP1.Sc-BDH.Sc], trp1/trp1, ura3::[NOXE.Sp-URA3]×3/ura3::[NOXE.Sp-URA3]×3

Conclusion

All the strains described in the current item g) have been tested for 2,3 BDO production; they produce equivalent amount than the above-mentioned recombinant strain YA1245.

Some of the above-mentioned strains further displayed advantageous technical effects in that they leads to a reduction of the glycerol synthesis or an improved resistance to weak acids in the culture medium.

```
SEQUENCES LISTING

SEQ ID NO: 1 (=ADN ALS.Bs)
ATGTCTACCAAAGCAACAAAAGAGCAAAAGAGCCTTGTGAAGAATAGAGGTG
CAGAACTTGTCGTTGATTGCTTGGTAGAACAGGGAGTCACTCACGTTTTCGGG
ATACCCGGCGCTAATCGACGCCGTGTTTGACGCTTTACAGGATAAGGGACC
AGAGATCATTGTTGCTAGACATGAACAGAATGCAGCGTTCATGGCTCAAGCTG
TAGGTAGACTTACTGGGAAACCCGGTGTGGTTTGGTTACTAGTGGACCAGGT
GCATCAAATCTAGCAACAGGTTTGTTAACAGCGAATACAGAGGGAGATCCTGT
TGTTGCATTAGCAGGAAACGTTATCAGAGCGGATAGACTGAAAAGAACCCAT
CAATCATTGGATAATGCTGCATTATTTCAGCCAATTACGAAATATTCCGTCGA
AGTACAGGATGTGAAGCATACCTGAAGCTGTAACTAATGCGTTTCGTATAG
CTTCTGCTGGTCAAGCTGGTGCAGCTTTTGTTTCGTTTCCGCAAGACGTTGTCA
ACGAGGTTACGAACACTAAGAATGTGAGAGCAGTAGCAGCCCCAAATTAGG
ACCAGCTGCTGATGATGCTATATCAGCTGCTATTGCTAAGATTCAGACAGCCA
AACTACCTGTTGTCTTAGTAGGTATGAAAGGTGGCAGGCCAGAAGCAATCAA
GGCAGTTAGAAAACTGTTGAAGAAGGTTCAATTGCCGTTTGTGGAAACCTATC
AAGCCGCAGGGACTTTGTCTAGGGATCTAGAAGATCAATACTTCGGTAGAATA
GGGTTGTTCAGAAATCAACCTGGCGACTTGTTACTGGAACAAGCCGATGTCGT
```

-continued

SEQUENCES LISTING

```
GCTTACAATTGGTTACGATCCGATTGAATATGACCCCAAATTTTGGAATATTA
ATGGTGATAGGACTATTATCCACTTAGACGAGATTATTGCCGATATTGACCAT
GCTTATCAACCTGATCTGGAACTGATAGGTGATATTCCAAGTACTATCAACCA
TATAGAGCATGATGCCGTCAAAGTGGAATTTGCCGAAAGAGAACAGAAGATC
CTATCCGATCTAAAGCAGTACATGCATGAAGGCGAACAAGTTCCAGCAGATTG
GAAATCCGATAGAGCACATCCATTGGAAATTGTCAAAGAATTGAGAAATGCA
GTTGATGACCATGTTACAGTTACTTGTGACATAGGTAGTCACGCTATTTGGAT
GTCTAGGTACTTCAGATCTTATGAGCCATTAACGTTGATGATATCCAATGGCA
TGCAAACCCTTGGAGTCGCTTTACCATGGGCCATTGGTGCGTCGTTAGTAAAG
CCAGGAGAGAAAGTCGTTTCTGTGTCAGGTGATGGTGGTTTCTTGTTCTCTGCC
ATGGAATTGGAAACCGCCGTTCGTTTGAAAGCCCCTATAGTACACATCGTGTG
GAATGATTCGACCTATGACATGGTCGCGTTTCCAATTGAAGAAGTACAACC
GTACTTCAGCTGTTGATTTCGGCAACATTGACATTGTGAAGTACGCGGAAAGC
TTTGGCGCCACAGGCCTGAGTCGAATCACCTGATCATTAGCAGATGTACT
TAGGCAAGGGATGCGCTGAAGGACCTGTAATTATCGACGTACCTGTTGACT
ATAGCGACAACATCAATTTAGCCAGTGATAAATTACCCGAGTTTGGTGAG
CTAATGACGAAGCTTTGTAA
```

SEQ ID NO: 2 (=Amino acid ALS.Bs)

```
MSTKATKEQKSLVKNRGAELVVDCLVEQGVTHVFGIPGAKIDAVFDALQDKGPEI
IVARHEQNAAFMAQAVGRLTGKPGVVLVTSGPGASNLATGLLTANTEGDPVVAL
AGNVIRADRLKRTHQSLDNAALFQPITTCYSVEVQDVKNIPEAVTNAFRUSAGQA
GAAFVSFPQDVVNEVTNTKNVRAVAAPKLGPAADDAISAAIAKJQTAKIPVVLVG
MKGGRPEAIKAVRKLLKKVQLPFVETYQAAGTLSRDLEDQYFGRIGLFRNQPGDL
LLEQADVVLTIGYDPIEYDPKFWNINGDRTIIHLDEIIADIDHAYQPDLELIGDIPSTI
NHIEHDAVKVEFAEREQKILSDLKQYMHEGEQVPADWKSDRAHPLEIVKELRNA
VDDHVTVTCDIGSHAIWMSRYFRSYEPLTLMISNGMQTLGVALPWAIGASLVKPG
EKVVSVSGDGGFLFSAMELETAVRLKAPIVHIVWNSTYDMVAFQQLKKYNRTS
AVDFGNIDIVKYAESFGATGLRVESPDQLADVLRQGMNAEGPVIIDVPVDYSDNI
NLASDKLPKEFGELMKTKAL
```

SEQ ID NO: 3 (=ADN ALS.Nt)

```
ATGGCTGCTGCTGCAGCTGCTCCATCTCCATCTTTTTCTAAAACCTTGTCCTCC
TCCTCTTCCAAATCTTCTACTTTGTTGCCAAGATCTACTTTCCCATTCCACATC
ATCCACATAAGACTACTCCACCACCATTGCATTTGACTCCAACTCATATTCACT
CCCAAAGAAGAAGATTCACCATCTCCAACGTTATTTCTACCACCCAAAAGGTT
TCTGAAACTCAAAAGGCTGAAACCTTCGTTTCTAGATTTGCTCCAGATGAACC
TAGAAAGGGTTCTGATGTTTTGGTTGAAGCTTTGGAAAGAGAAGGTGTTACCG
ATGTTTTTGCTTATCCAGGTGGTGCTTCTATGGAAATTCATCAAGCTTTGACCA
GATCCTCCATCATTAGAAATGTTTTGCCAAGACATGAACAAGGTGGTGTTTTC
GCGCTGAAGGTTATGCTAGAGCTACTGGTTTTCCAGGTGTATGTATTGCTACT
TCTGGTCCAGGTGCTACTAATTTGGTTTCTGGTTTGGCTGATGCTTTGTTGGAT
TCTGTTCCAATCGTTGCTATTACTGGTCAAGTTCCAAGAAGAATGATTGGTAC
AGATGCTTTCCAAGAAACCCCAATTGTCGAAGTTACTAGATCTATTACCAAGC
ACAACTACTTGGTTATGGACGTTGAAGATATCCCAAGAGTTGTTAGAGAAGCA
TTTTTCTTGGCTAGATCTGGTAGACCAGGTCCAGTTTTGATTGATGTTCCAAAG
GATATCCAACAACAATTGGTTATCCCAGATTGGGACCAACCTATGAGATTGCC
AGGTTATATGTCTAGATTGCCAAAGTTGCCAAACGAAATGTTGTTAGAACAAA
TCGTCAGATTGATCTCCGAATCTAAAAAGCCAGTCTTGTATGTTGGTGGTGTT
GTTCTCAATCTAGTGAAGAATTGAGAAGATTCGTCGAATTGACCGGTATTCCA
GTTGCTTCTACATTGATGGGTTTGGGTGCTTTTCCAACTGGTGATGAATTGTCT
TTGTCTATGTTGGGTATGCACGGTACTGTTTATGCTAATTACGCTGTTGATTCC
TCCGATTTGTTGTTAGCTTTTGGTGTTAGATTCGATGATAGAGTCACTGGTAAG
TTGGAAGCTTTTGCTTCTAGAGCTAAGATCGTTCATATCGACATTGATTCCGCT
GAAATCGGTAAAAACAAGCAACCACATGTTTCTATTTGCGCCGATATTAAGTT
GGCATTGCAAGGTTTGAACAGTATCTTGGAATCCAAAGAAGGTAAATTGAAGT
TGGACTTCTCTGCTTGGAGACAAGAATTGACAGTTCAAAAGGTTAAGTACCCA
TTGAACTTCAAGACTTTCGGTGATGCTATTCCACCACAATACGCTATTCAAGTT
TTGGATGAATTGACCAACGGTTCCGCTATTATTTCAACTGGTGTTGGTCAACAT
CAAATGTGGGCTGCTCAATATTACAAGTACAGAAAACCTAGACAATGGTTGAC
TTCTGGTGGTTAGGTGCTATGGGTTTTGGTTTGCCAGCTGCTCTATTGGTGCTGC
TGTTGGTAGACCTGATGAAGTTGTTGTAGATATTGATGGTGACGGTTCCTTCAT
TATGAACGTCCAAGAATTGGCTACCATCAAGGTTGAAAATTTGCCAGTCAAGA
TCATGTTATTGAACAATCAACACTTGGGTATGGTCGTCCAATGGGAAGATAGA
TTTTACAAAGCTAATAGAGCCCACACCTACTTGGGTAATCCATCTAATGAAGC
TGAAATCTTCCCAAACATGTTGAAGTTTGCTGAAGCTTGTGGTGTTCCAGCTGC
AAGAGTTACTCATAGAGATGATTTGAGAGCTGCCATCCAAAAGATGTTGGATA
CTCCAGGTCCATACTTTGTTGGATGTTATTGTCCCACATCAAGAACATGTCTTGC
CAATGATTCCATCTGGTGGTGCCTTTAAAGATGTTATTACTGAAGGTGACGGT
AGATCCTCTTACTGA
```

SEQ ID NO 4 (=Amino acid ALS.Nt)

```
MAAAAAAPSPSFSKTLSSSSSKSSTLLPRSTFPFPHHPHKTTPPPLHLTPTHTHSQRR
RFTISNVISTTQKVSETQKAHTFVSRFAPDEPRKGSDVLVEALEREGVTDVFAYPG
GASMEIHQALTRSSIIRNVLPRHEQGGVFAAEGYARATGFPGVCIATSGPGATNLV
SGLADALLDSVPIVAITGQVPRRMIGTDAFQETPIVEVTRSITKHNYLVMDVEDIPR
VVREAFFLARSGRPGPVLIDVPKDIQQQLVIPDWDQPMRLPGYMSRLPKLPNEML
```

SEQUENCES LISTING

LEQIVRLISESKKPVLYVGGGCSQSSEELRRFVELTGIPVASTLMGLGAFPTGDELS
LSMLGMHGTVYANYAVDSSDLLLAFGVRFDDRVTGKLEAFASRAKIVHIDIDSAE
IGKNKQPHVSICADIKLALQGLNSILESKBGKLKLDFSAWRQELTVQKVKYPLNFK
TFGDAIPPQYAIQVLDELTNGSAIISTGVGQHQMWAAQYYKYRKPROWLTSGGL
GAMGFGLPAAIGAAVGRPDEVVVDIDGDGSFIMNVQELTIKVENLPVKIMLLNN
QHLGMVVQWEDRFYKANRAHTYLGNPSNEAEIFPNMLKFAEACGVPAARVTHR
DDLRAAIQKMLDTPGPYLLDVIVPHQEHVLPMIPSGGAFKDVITEGDGRSSY

SEQ ID No 5 (=ADN ALS.Pp)
ATGTCCGCACAAATACCTGAAGTTAGAAGTACAAATGAATTGAGAGAAAAT
GGATGAAGCCTGAAGTAATCACTGGTTCCGAAATATTGTTAAGATCATTGTTA
TTGGAAGGTGTCGATTGTGTATTTGGTTATCCAGGTGGTGCTGTCTTGTACATC
TATGATGCAATGTACGGTTTTAAAGACTTCAAGCATGTTTTAACCAGACACGA
ACAAGGTGCTATACATGCTGCAGATGGTTATGCCAGAGCTTCCGGTAAAGTAG
GTGTTTGCATCGCAACAAGTGGTCCAGGTGCCACCAATTTGGTTACTGGTATC
GCAACAGCCTTTATGGATTCTGTTCCTTTGGTTGTCATTACGGTAACGTCATT
TCTTCATTAATCGGTACAGATGCATTCCAAGAAGCCGACATAACTGGTATCAC
AATGCCAATAACTAAGCACTCATATTTGGTTAGAGATGTCGAAGACTTGCCTA
GAATAATCCATGAAGCATTTCACATAGCAAATACAGGTAGAAAGGGTCCAGT
TTTGATAGATATCCCTAAAGACATATCCGCCGCTCAAACCTTATTCGTACCAC
AAACCGGTCCTGTTACTATGAGAGGTTACAACCCAAAGGTTTTGCCTAACAAG
ATACAATTGGATAAATTGACACAAGCCATCTCCGAAGCTGAAAGACCATTCAT
TTTGGCAGGTGGTGGTGTAGTTTATAGTGGTGGTCATGAAGCCTTATACGAAT
TTGTTAGAAAGACTGAAATCCCTATCACTACAACCTTATTGGGTTTAGGTGGTT
TCCCATCAGGTCATGAATTGTGGACTGGTATGCCTGGTATGCACGGTACATAC
ACCTCCAATCAAGCAATACAACAATCTGATTTGTTGATCTGTATTGGTGCTAG
ATTTGATGACAGAGTTACTGGTAAATTGGATGGTTTCGCACCACAAGCCAAAA
TTGTACATATAGATATCGACCCTGCAGAAATAGGTAAAAATGTTGCAGCCGAT
ATTCCAATAGTAGGTGACGTTAAGGCTGTCTTAGAATTATTGAACCAAGATGT
TAAGAGAGCCGATAGAGCTGACGCATGGAGAGCACAAATCCAACATTGGAAG
AACGAAAAGCCATATTCCTACAAGGATAGTGAAACAGTTTTGAAACCTCAATG
GGTCGTAGAATTATTGGATGAAACTACAAAGGGTGGTGCTATTGTCACCACTG
ACGTAGGTCAACACCAAATGTGGGCTGCACAATACTACAAGTTTAATCAACCA
AGATCATGGGTTACATCAGGTGGTTTAGGTACTATGGGTTTTGGTTTCCCATCT
GCTATTGGTGCACAAATGGCCAATCCTGATAGATTGGTTATCTCTATTAACGG
TGACGGTGGTATGCAAATGTGTTCACAAGAATTAGCTATTTGCGCTATTAATA
ACATCCCAGTAAAGATCGTTATCATTAATAACCAAGTTTTGGGTATGGTCAGA
CAATGGCAAGAATTGATCTATAACAACAGATACTCTCATATTGATTTGGCTGG
TTCACCTGACTTTTGTCAAATTGGCCGAAGCCTATGGTGTAAAGGGTTTAAGAG
CAACCAATAAGGAAGAAGCCAGAAGAGCTTGGCAAGAAGCATTGGATACTCC
AGGTCCTGTTGTCGTAGAATTTGTTGTCTCTAAAGAAGAAAACGTTTATCCAA
TGGTTACACAAGGTTCCACAATAGACCAAATGTTGATGGGTGACGAATGA

SEQ ID NO: 6 (=Amino acid ALS.Pp)
MSAQIPEVRSTNELREKWMKPEVITGSEILLRSLLLEGVDCVFGYPGGAVLYIYDA
MYGFKDFKHVLTRHEQGAIHAADGYARASGKVGVCIATSGPGATNLVTGIATAF
MDSVPLVVITGNVISSLIGTDAFQEADITGITWITKHSYLVRDWEDLPRIIHEAFHI
ANTGRKGPVLIDIPKDISAAQTLFVPQTGPVTMRGYNPKVLPNKIQLDKLTQAISE
AERPFILAGGGVVYSGGHEALYEFVRKTEIPITTTLLGLGGFPSGHELWTGMPGM
HGTYTSNQAJQQSDLLICIGARFDDRVTGKLDGFAPQAKIVHIDIDPAEIGKNVAA
DIPIVGDVKAVLELLNQDVKRADRADAWRAQIQHWKNEKPYSYKDSETVLKPQ
WVVELLDETTKGGAIVTTDVGQHQNIWAAQYYKFNQPRSWVTSGGLGTMGFGF
PSAIGAQMANPDRLVISINGDGGMQMCSQELAICAINNIPVKWIDQNQVLGMVRQ
WQELIYNNRYSHIDLAGSPDFVKLAEAYGVKGLRATNKEEARRAWQEALDTPGP
VVVEFVVSKEENVYPMVTQGSTIDQMLMGDE SEQ ID NO: 7 (=ADN ALD.Bb)
ATGGGTAAGAAGAACATTATTACCTCTATCACCTCCTTGGCTTTGGTTGCTGGT
TTGTCTTTGACTGCTTTTGCTGCTACTACTGCTACTGTTCCAGCTCCACCAGCT
AAACAAGAATCTAAACCAGCTGTTGCTGCTAATCCAGCTCCTAAGAATGTTTT
GTTCCAATACTCTACCATCAACGCCTTGATGTTGGGTCAATTTGAAGGTGATTT
GACCTTGAAGGACTTGAAGTTGAGAGGTGATATGGGTTTGGGTACTATCAATG
ATTTGGACGGTGAAATGATCCAAATGGGTACTAAGTTCTACCAAATCGATTCT
ACCGGTAAGTTGTCTGAATTGCCAGAATCTGTTAAGACTCCATTCGCTGTTACT
ACTCACTTCGAACCTAAAGAAAAGACTACCTTGACCAACGTCCAAGACTACAA
TCAATTGACCAAGATGTTGGAAGAAAAGTTCGAAAACAAGAACGTTTTCTACG
CCGTTAAGTTGACTGGTACTTTCAAAATGGTTAAGGCTAGAACCGTTCCTAAG
CAAACTAGACCATATCCACAATTGACTGAAGTCACCAAGAAGCAATCCGAATT
TGAATTCAAGAACGTCAAGGGTACTTTGATCGGTTTTTACACTCCAAATTATG
CTGCTGCTTTGAACGTTCCAGGTTTTCACTTGCATTTCATTACCGAAGATAAGA
CCTCTGGTGGTCATGTTTTGAACTTGCAATTTGATAACGCCAACTTGGAAATCT
CCCCAATCCATGAATTTGATGTTCAATTGCCACACACCGATGATTTCGCTCATT
CTGATTTGACTCAAGTTACTACCTCCCAAGTTCATCAAGCTGAATCTGAAAGA
AAGTA

SEQUENCES LISTING

SEQ ID NO: 8 (=Amino acid ALD.Bb)
MGKKNIISITSLALVAGLSLTAFAATTATVPAPPAKQESKPAVAANPAPKNVLFQ
YSTINALMLGQFEGDLTLKDLKLRGDMGLGTINDLDGEMIQMGTKFYQIDSTGKL
SELPESVKTPFAVTTHFEPKEKTTLTNVQDYNQLTKMLEEKFENKNVFYAVKLTG
TFKMVKARTVPKQTRPYPQLTEVTKKQSEFEFKNVKGTLIGFYTPNYAAALNVPG
FHLHFITEDKTSGGHVLNLQFDNANLEISPIHEFDVQLPHTDDFAHSDLTQVTTSQ
VHQAESERK SEQ ID NO: 9 (=ADN ALD.Ea)
ATGATGATGCACTCCTCCGCCTGCGACTGTGAAGCAAGTTTATGCGAAACATT
GAGAGGTTTTTCCGCCAAGCACCCAGATTCCGTTATATATCAAACATCCTTGA
TGAGTGCTTTGTTATCTGGTGTCTACGAAGGTGACACTACAATCGCAGACTTG
TTAGCTCATGGTGACTTTGGTTTGGCTACTTTTAATGAATTAGACGGTGAAATG
ATCGCATTTTCTTCACAAGTTTACCAATTGAGAGCTGATGGTTCAGCAAGAGC
TGCAAAACCAGAACAAAAGACACCTTTTGCAGTCATGACCTGGTTCCAACCAC
AATACAGAAAAACTTTTGATGCCCCAGTTTCAAGACAACAAATTCACGATGTA
ATAGACCAACAAATCCCTTCAGATAATTGTTTTGTGCCTTGAGAATAGACGG
TAACTTCAGACATGCTCACACCAGAACTGTTCCAAGACAAACTCCACCTTATA
GAGCCATGACAGATGTATTGGATGACCAACCTGTTTTTAGATTCAATCAAAGA
GAAGGTGTTTTAGTCGGTTTTAGAACCCCACAACACATGCAAGGTATCAACGT
AGCAGGTTATCATGAACACTTCATTACTGATGACAGACAAGGTGGTGGTCATT
TGTTAGATTACCAATTGGAATCCGGTGTTTTGACATTCGGTGAAATCCACAAG
TTGATGATTGATTTGCCAGCCGACAGTGCTTTCTTACAAGCCAACTTACACCCA
TCAAACTTAGACGCCGCAATCAGATCAGTAGAAAACTAA SEQ ID NO: 10 (=Amino acid ALD.Ea)
MMMHSSACDCEASLCETLRGFSAKHPDSVIYQTSLMSALLSGVYEGDTTIADLLA
HGDFGLGTFNELDGEMIAFSSQVYQLRADGSARAAKPEQKTPFAVMTWFQPQYR
KTFDAPVSRQQIHDVIDQQIPSDNLFCALRIDGNFRHAHTRTVPRQTPPYRAMTDV
LDDQPVFRFNQREGVLVGFRTPQHMQGINVAGYHEHFITDDRQGGGHLLDYQLE
SGVLTFGEIHKLMIDLPADSAFLQANLHPSNLDAAIRSVEN SEQ ID NO: 11 (=ADN ALD.L1)
ATGTCATCGAGAATCTTTCAACACAATACCTTCACAACTTTGAGTAGCGGATT
TTACAAAGGCACAATCACGTTGAAAGAAGCCTTAGAACACGGATCAGTTGGC
ATAGGTACATTAGATACTGCAAATGGTGAAGTTACCATCATCAACGGTATAGC
CTATCATGGAGATTCGGAAAACCATGTGAGATTGGTGGAAGAGGATGAAACG
ATGCCTTATGTCGCTATGGTTAACATCAACCCATTGCAAAGTTCACTGATTCC
TCTGTGTCAAATAGCGAAGATTTCCTATCCGCTTTAACCAAAAGGTTTCCAAC
CGTTAATACTGCCTACACAATTGTCATGACTGGTCAGTTTAAGGAAGTAACTG
TCTCTTCTAAACCAGCGAACAATACTAGACCATATGACGAAATAATGGCTGAT
CAACCGTACTTTACAAAGGAGAACATTAGTGGTACAATGGTTGGTGTATGGGC
TCCTAAACATCTTACTGATCTATTTGGGTTAGGCTTTCACCTTCACTTCGTTTCT
GACGATAAGACGTTTACTGCACATGTACAGAATTTCATTACAGAGAATCTGGA
AATTGAGATAGGGAAAATTACCAAGATTGACCAAGAATTTCCTGATGATGAC
GAGAACTTCGACCAACATTTGTTCCAATAA SEQ ID NO: 12 (=Amino acid ALD.L1)
MSSRIFQHNTFTTLSSGFYKGTITLKEALEHGSVGIGTLDTANGEVTIINGIAYHGD
SENHVRLVEEDETMPYVAMVEHQPIAKFTDSSVSNSEDFLSALTKRFPTVNTAYTI
VMTGQFKEVTVSSKPANNTRPYDEIMADQPYTTKENISGTNTVGVWAPKHLTDLF
GLGFHLHFVSDDKTFTAHVQNFITENITRGKITKIDQEFPDDDENFDQHLFQ SEQ ID NO: 13 (=ADN BDH.Ea)
ATGGGCAAAGTAGCGTTAGTGACAGGTGCTGGTCAAGGCATTGGAAAGGCCA
TTGCCTTGAGATTGGTTAAAGATGGCTTTGCGGTCGCTATAGCCGATTACAAC
GATGTGACTGCTAAAGCCGTTGCAGACGAGATCAATCAACACGGAGGTAGAG
CTATAGCTGTCAAAGTTGACGTCAGTGATAGAGAACAGGTTTTCGCTGCTGTA
GAACAAGCACGTAAAACGTTAGGCGGTTTTAACGTCATCGTCAATAATGCGGG
AGTAGCACCATCAACCCCTATAGAGTCCATTACACCCGAAATAGTGGACAAA
GTGTACAACATCAATGTTAAGGGTGTGATTTGGGGTATTCAAGCCGCAGTTGA
AGCATTCAAGAAGAAGGTCATGGTGGCAAGATCATTAACGCCTGTTCACAA
GCAGGACATGTAGGCAATCCGGAATTAGCGGTTTACTCTTCGTCTAAGTTTGC
TGTTAGAGGGTTAACCCAGACAGCTGCTAGAGATCTTGCACCTCTTGGTATCA
CTGTAAACGGTTATTGCCCAGGTATTGTCAAAACACCAATGTGGGCAGAGATA
GATAGGCAAGTATCTGAAGCTGCAGGGAAACCTCTAGGATATGGTACTGCCG
AATTTGCCAAGAGGATTACGTTGGGTAGACTATCGAGCCAGAAGATGTTGCT
GCTTGTGTTTCCTATTTGGCAAGTCCCGACTCAGACTATATGACTGGACAGAG
CTTGCTGATTGATGGTGGGATGGTTTTCAATTAA SEQ ID NO: 14 (=Amino acid BDH.Ea)
MGKVALVTGAGQGIGKAIALRLVKDGFAVAIADYNDVTAKAVADEINQHGGRAI
AVKVDVSDREQVFAAVEQARKTLGGFNVIVNNAGVAPSTPIESITPEIVDKVYNIN
VKGVIWGIQAAVEAFKKEGHGGKHNACSQAGHVGNPELAVYSSSKFAVRGLTQT
AARDLAPLGITWGYCPGIVKTPMWAEIDRQVSTAAGKPLGYGTAEFAKRITLGR
LSEPEDVAACVSYLASPDSYMTGQSLLTDGGMVFN

SEQUENCES LISTING

SEQ ID NO: 15 (=ADN BDH.Pp)
ATGTCTGCTTTGAGATGGCATGGTGTTAAGGATTTGAGATTGGAAAACATTGA
ACAACCAGCTGCTTTGCCAGGTAAGGTTAAGATTAAGGTTGAATGGTGTGGTA
TTTGCGGTTCTGACTTGCATGAATATGTTGCTGGTCCAATTTTCATTCCAGAA
ACGCTCAACATCCATTGACTGGTGAAAAAGCTCCAATAGTTATGGGTCATGAA
TTCTCCGGTCAAGTTGTTGAAATTGGTGAAGGTGTTACCAAGATCCAAGTTGG
TGATAGAGTTGTTGTTGAACCAGTTTTTGCTTGCGGTGAATGTGATGCTTGTAG
ACAAGGTAAATACAACTTGTGCGATAAGATGGGTTTTTTGGGTTTGGCCGGTG
GCGGTGGTGGTTTTTCTGAATACGTTGCAGCTGATGAACATATGGTTCACAAG
ATTCCAGAATCCGTCAGTTTTGAACAAGGTGCTTTGGTTGAACCATCTGCTGTT
GCATTATATGCCGTTAGACAATCCCAATTGAAAGTCGGTGATAAGGCTGTTGT
TTTTGGTGCTGGTCCTATTGGTTTGTTGGTTATTGAAGCTTTGAAGGCTTCTGG
TGCTTCTGAAATCTATGCTGTTGAATTGTCCGAAGAAAGAAAGGCTAAAGCTG
AAGAATTGCGTGCCATAGTTIAGATCCAAAGACCTATGATGTCGTCGAAGAA
TTGCATAAGAGAACTAATGGTGGTGTTGATGTTGCTTACGAAGTTACTGGTGT
TCCACCAGTTTTGACTCAAGCTATTGAATCCACTAAGATCTCTGGTCAAATCAT
GATCGTCAGTATCTTCGAAAAAGAAGCCCCTATTAAGCCAAACAACATCGTCA
TGAAGGAAAGAAACTTGACTGGTATCATCGGTTACAGAGATGTTTTCCCAGCT
GTTATCTCTTTGATGGAAAAGGGTTATTTTCCAGCCGATAAGTTGGTCACTAA
GAGAATCAAATTGGAAGAAGTCATCGAACAAGGTTTCGAAGGTTTGTTGAAA
GAAAAGAATCAAGTTAAGATCTTGGTTTCCCCAAAGGCCTAA

SEQ ID NO: 16 (=Amino acid BDH.Pp)
MSALRWHGVKDLRLENIEQPAALPGKVK1KVEWCGICGSDLHEYVAGPIFIPENA
QHPLTGEKAPIVMGHEFSGQVVEIGEGVTKIQVGDRVVVEPVFACGECDACRQG
KYNIXDKMGFLGLAGGGGGFSEYVAADEHMVHKIPESVSFEQGALVEPSAVALY
AVRQSQLKVGDKAVVFGAGPIGLLVIEALKASGASEIYAVELSEERKAKAEELGAI
VLDPKTYDWEELHKRTNGGVDVAYEVTGVPPVLTQAIESTKISGQIMIVSIFEKE
APIKPNNIVMKERNLTGIIGYRDVFPAVISLMEKGYFPADKLVTKRIKLEEVIEQGF
EGLLKEKNQVKILVSPKA SEQ ID NO: 17 (=ADN BDH.Ko)
ATGGGTAAAGTCGCATTGGTCACTGGTGCTGGTCAAGGTATCGGTAAAGCTAT
CGCATTGAGATTGGTAAAAGACGGTTTCGCTGTCGCCATCGCTGATTATAATG
ACGCAACTGCCCAAGCTGTTGCAGATGAAATTAACAGAAGTGGTGGTAGAGC
CTTGGCTGTTAAAGTCGATGTATCTCAAAGAGACCAAGTCTTTGCTGCAGTAG
AACAAGCTAGAAAGGGTTTAGGTGGTTCGATGTTATAGTCAATAACGCAGGT
GTTGCCCCATCAACACCTATCGAAGAAATCAGAGAAGATGTTATCGACAAGGT
CTACAACATCAACGTAAAGGGTGTTATATGGGGTATCCAAGCCGCTGTCGAAG
CCTTTAAACAAGAAGGTCATGGTGGTAAAATTATTAACGCTTGTTCTCAAGCA
GGTCACGTAGGTAACCCAGAATTGGCCGTTTACTCTTCATCCAAATTCGCAGT
TAGAGGTTTAACTCAAACAGCAGCCAGAGATTTGGCTCATTTGGGTATCACAG
TCAATGGTTATTGCCCAGGTATTGTAAAGACCCCTATGTGGGCAGAAATAGAC
AGACAAGTTTCAGAAGCTGCAGGTAAACCTTTGGGTTACGGTACTCAAGAATT
TGCTAAGAGAATAACTTTGGGTAGATTATCCGAACCTGAAGATGTCGCTGCCT
GTGTCTCCTACTTGGCTGGTACTGACTCAAACTGTATGTGA SEQ ID NO: 18 (=Amino acid BDH.Ko)
MGKVALVTGAGQGIGKAIALRLVKDGFAVAIADYNDATAQAVADEINRSGGRAL
AVICVDVSQRDQVFAAVEQARKGLGGFDVIVNNAGVAPSTPIEEIREDVIDKVYNI
NVKGVIWGIQAAVEAFKQEGHGGKIINACSQAGHVGNPELAVYSSSKFAVRGLT
QTAARDLAHLGITVNGYCPGrVKTPMWAEIDRQVSEAAGKPLGYGTQEFAKRITL
GRLSEPEDVAACVSYLAGTDSNCM SEQ ID NO: 19 (=ADN BDH1.Sc)
ATGAGAGCTTTGGCATATTTCAAGAAGGGTGATATTCACTTCACTAATGATAT
CCCTAGGCCAGAAATCCAAACCGACGATGAGGTTATTATCGACGTCTCTTGGT
GTGGGATTTGTGGCTCGGATCTTCACTTAGTACTTGGATGGTCCAATCTTCATGC
CTAAAGATGGAGAGTGCCATAAATTATCCAACGCTGCTTTACCTCTGCAATG
GGCCATGAGATGTCAGGAATTGTTTCCAAGGTTGGTCCTAAAGTGACAAGGT
GAAGGTTGGCGACCACGTGGTCGTTGATGCTGCCAGCAGTTGTGCGGACCTGC
ATTGCTGGCCACACTCCAAATTTTACAATTCCAAACCATGTGATGCTTGTCAG
AGGGGCAGTGAAAATCTATGTACCCACGCCGGTTTTGTAGGACTAGGTGTGAT
CAGTGGTGGCTTTGCTGAACAAGTCGTAGTCTCTCAACATCACATTATCCCGG
TTCCAAAGGAAATTCCTCTAGATGTGGCTGCTTTAGTTGAGCCTCTTTCTGTCA
CCTGGCATGCTGTTAAGATTTCTGGTTTCAAAAAGGCAGTTCAGCCTTGGTTC
TTGGTGCAGGTCCCATTGGGTTGTGTACCATTTTGGTACTTAAGGGAATGGGG
GCTAGTAAAATTGTAGTGTCTGAAATTGCAGAGAGAAGAATAGAAATGGCCA
AGAAACTGGGCGTTGAGGTGTTCAATCCCTCCAAGCACGGTCATAAATCTATA
GAGATACTACGTGGTTTGACCAAGAGCCATGATGGGTTTGATTACAGTTATGA
TTGTTCTGGTATTCAAGTTACTTTCGAAACCTCTTTGAAGGCATTAACATTCAA
CTTGACAGCCACCAACATTGCAGTTTGGGGTCCAAAACCTGTCCCATTCCAAC
CAATGGATGTGACTCTCCAAGAGAAAGTTATGACTGGTTCGATCGGCTATGTT

```
GTCGAAGACTTCGAAGAAGTTGTTCGTGCCATCCACAACGGAGACATCGCCAT
GGAAGATTGTAAGCAACTAATCACTGGTAAGCAAAGGATTGAGGACGGTTGG
GAAAAGGGATTCCAAGAGTTGATGGATCACAAGGAATCCAACGTTAAGATTC
TATTGACGCCTAACAATCACGGTGAAATGAAGTAA

SEQ ID NO: 20 (=Amino acid BDH1.Sc)
RALAYFKKGDIHFTNDIPRPEIGQDDEVIIDVSWCGICGSDLHEYLDGPIFMPKDGE
CHKLSNAALPLAMGHEMSGIVSKVGPKVTKVKVGDHVVVDAASSCADLHCWPH
SKFYNSKPCDACQRGSENLCTHAGFVGLGVISGGFAEQVVVSQHHIIPVPKEIPLD
VAALVEPLSVTWHAVKISGFKKGSSALVLGAGPIGLCTILVLKGMGASKIVVSEIA
ERRIEMAKKLGVEVFNPSKHGHKSIEILRGLTKSHDGFDYSYDCSGIQVTFETSLK
ALTFKGTATNIAVWGPKPVPFQPMDVTLQEKVMTGSIGYVVEDFEEVVRAIHNG
DIAMEDCKQLITGKQRIEDGWEKGFQELMDHKESNVICILLTPNNHGEMK SEQ ID NO: 21 (=ADN NOXE.L1)
ATGGGTATTGTCGTAATAGGTACTAACCATGCCGGAATAGCTACAGCAAATAC
CTTAATCGACCAATATCCAGGACATGAAATTGTTATGATTGACAGAAACTCGA
ATATGAGTTATCTTGGCTGTGGTACAGCGATTTGGGTTGGGAGACAAATCGAG
AAACCTGATGAACTTTTCTATGCAAAAGCAGAAGATTTCGAAAAGAAGGGTG
TTAAAATCCTGACCGAGACTGAAGTGTCAGAAATCGACTTTACCAACAAAATG
ATATATGCCAAAAGCAAGACTGGGGAGAAAATCACGGAATCTTATGATAAGC
TAGTATTGGCAACAGGAAGCAGACCAATCATACCCAATTTGCCTGGTAAAGAT
CTTAAAGGAATTCATTTCTTAAAGTTATTCCAGGAAGGTCAAGCCATTGACGA
AGAATTCGCAAAGAATGACGTGAAATGAATCGCGGTAATTGGTGCTGGTTAT
ATTGGAACAGAGATAGCTGAAGCAGCTAAACGTAGAGGGAAAGAAGTGTTGT
TGTTTGATGCTGAAAGTACCTCATTAGCGTCATACTACGACGAAGAATTTGCC
AAAGGCATGGATGAAAATTTGGCACAACACGGGATTGAGTTGCACTTTGGTG
AACTTGCCCAAGAGTTCAAGGCAAATGAAGAAGGTCATGTCTCCCAGATTGTT
ACAAACAAATCCACTTATGATGTGGATCTGGTCATCAATTGCATAGGATTTAC
TGCCAATTCAGCCTTAGCTGGTGAGCATCTAGAAACGTTTAAGAACGGTGCCA
TAAAGGTTAATAAGCATCAACAATCTAGTGATCCAGACGTGTATGCAGTTGGT
GATGTTGCAACTATCTACTCTAACGCTTTGCAAGACTTTACTTACATCGCTTTA
GCTAGCAATGCTGTTAGATCAGGCATTGTTGCTGGACACAATATTGGCGGTAA
ATCCATAGAATCTGTCGGTGTTCAGGGTAGTAACGGCATTTCTATATTCGGAT
ACAATATGACAAGTACTGGTTTATCAGTAAAAGCTGCTAAGAAGATTGGTCTA
GAAGTCTCCTTTTCTGATTTTGAAGATAACTTAAAAGGCTTGGTTTCTGCATGA
GAACAATGATTCGGTCAAAATAAGGATCGTATACGAAACAAAATCCAGGAGA
ATAATTGGCGCACAATTGGCATCGAAATCAGAGATTATAGCGGGCAACATTA
ACATGTTCTCTTTAGCCATTCAGGAAAAGAAAACGATTGATGAGTTAGCCCTA
TTGGATTTGTTCTTTCTGCCTCACTTTAACTCTCCGTACAATTATATGACCGTA
GCTGCGTTGAATGCTAAATAA SEQ ID NO: 22 (=Amino acid NOXE.L1)
MGIVVIGTNHAGIATANTLIDQYPGHEIVMIDRNSNMSYLGCGTAIWVGRQIEKPD
ELFYAKAEDFEKKGVKILTETEVSEIDPTNKMIYAKSKTGEKITESYDKLVLATGS
RPIIPNLPGKDLKGIHFLKLFQEGQAIDEEFAKNDVKRIAVIGAGYIGTEIAEAAKR
RGKEVLLFDAESTSLASYYDEEPAKGMDENLAQHGIELHFGELAQEFKANEEGHV
SQIVTNKSTYDVDLVINCIGFTANSALAGEHLETFKNGAIKVNKHQQSSDPDVYA
VGDVATIYSNALQDFTYIALASNAVRSGIVAGHNIGGKSIESVGVQGSNGISIFGYN
MTSTGLSVKAAKKIGLEVSFSDFEDKQKAWFLHENNDSVKIRIVYETKSRRIIGAQ
LASKSEIIAGNINMFSLAIQEKKTIDELALLDLFFLPHFNSPYNYMTVAALNAK SEQ ID NO: 23 (=ADN NOXE.Spn)
ATGTCTAAGATAGTGGTAGTTGGTGCTAACCATGCAGGAACTGCTTGCATCAA
TACGATGTTGGATAATTTCGGCAATGAAAATGAGATAGTGGTGTTTGATCAGA
ATTCCAACATCAGCTTTCTAGGTTGTGGTATGGCGTTATGGATTGGGGAGCAA
ATAGATGGTGCTGAAGGGTTGTTTTACTCAGACAAAGAGAAATTGGAAGCCA
AAGGTGCCAAAGTCTACATGATTTTCGCCAGTCCTGAGTATAGACTATGACAAC
AAAGTGGTAACTGCAGAAGTAGAAGGCAAAGAGCACAAAGAATCCTATGAGA
AACTGATCTTTGCTACTGGTTCAACACCGATTTTACCACCTATTGAAGGAGTCG
AGATCGTTAAAGGTAATAGAGAATTTAAGGCCACACTTGAAAACGTACAATTT
GTTAAGTTGTATCAGAATGCTGAAGAAGTCATCAACAAGCTTTCAGATAAAAG
CCAGCATTTAGATAGGATTGCTGTTGTTGGAGGTGGATACATTGGTGTTGAAT
TGGCTGAAGCCTTTGAAAGACTAGGAAAAGAAGTTGTGTTAGTTGACATTGTG
GACACTGTCTTAAACGGGTATTATGACAAAGATTTCACCCAAATGATGGCCAA
GAATCTTGAGGATCACAACATTAGACTTGCTTTAGGCCAAACAGTGAGGCTA
TTGAAGGCGATGGTAAGGTAGAAAGGTTGATTACAGACAAGGAGTCTTTCGA
TGTTGACATGGTCATTTTAGCAGTAGGATTAGACCAAACACTGCTTTGGCAG
ATGGGAAAATTGAATTGTTTAGAAATGGTGCTTTTCTGGTGGATAAGAAACAA
GAAACTTCAATACCCGATGTTTATGCAGTTGGTGATTGTGCAACAGTCTATGA
TAATGCCAGAAAGGATACTTCCTACATAGCATTGGCATCTAATGCAGTTAGAA
CGGGCATTGTTGGTGCTTATAATGCCTGTGGTCATGAATTGGAGGGCATTGGT
GTCCAAGGTTCTAATGGTATATCGATTTATGGCCTTCATATGGTTAGTACCGGA
TTGACTCTGGAGAAGGCCAAAGCTGCTGGATACAATGCGACAGAAACAGGTT
TCAACGATTTACAGAAGCCAGAGTTTATGAAACACGACAACCATGAAGTAGC
GATCAAAATCGTATTTGACAAGGATTCTCGTGAAATTCTAGGGGCACAAATGG
TTTCACACGATATAGCGATAAGTATGGGCATCCATATGTTCTCTCTAGCGATTC
```

```
                      SEQUENCES LISTING

AAGAACATGTTACCATAGATAAArTAGCATTAACCGATCTATTCTTCTTGCCTC
ATTTCAACAAACCTTACAATTACATCACGATGGCAGCTTTGACCGCCGAAAAG
TAA

SEQ ID NO: 24 (=Amino acid NOXE.Spn)
MSKIVWGANHAGTACINTMLDNFGNENEIVVFDQNSNISFLGCGMALWIGEQID
GAEGLFYSDKEKLEAKGAKVYMNSPVLSIDYDNKWTAEVEGKEHKESYEKLIF
ATGSTPILPPIEGVEIVKGNREFKATLENVQFVKLYQNAEEVINKLSDKSQHLDRIA
WGGGYIGVELAEAFERLGKEWLVDIVDTVLNGYYDKDFTQMMAKNLEDHNIR
LALGQTVKAIEGDGKVERLITDKESFDVDMVILAVGFRPNTALADGKIELFRNGA
FLVDKKQETSIPDVYAVGDCATVYDNARKDTSYTALASNAVRTGIVGAYNACGH
ELEGIGVQGSNGISIYGLHMVSTGLTLEKAKAAGYNATETGFNDLQKPEFMKIIDN
HEVAIKIWDKDSREILGAQMVSHDIAISMGIHMFSLAIQEHVTIDKLALTDLFFLP
HFNKPYNYTTMAALTAEK SEQ ID NO: 25 (=ADN NOXE.Ef)
ATGTCTGTGGTTGTCGTAGGCTGTACACATGCTGGTACTAGTGCAGTGAAATC
TATCCTAGCTAATCATCCCGAAGCTGAAGTCACTGTTTATGAACGTAATGACA
ACATATCCTTCTTGTCTTGTGGAATTGCACTTTATGTTGGAGGTGTAGTTAAGA
ATGCTGCCGACTTATTTTACAGCAATCCTGAGGAATTAGCCAGTTTAGGAGCC
ACTGTGAAAATGGAACACAACGTAGAAGAGATCAATGTCGATGATAAGACAG
TTACGGCAAAGAATCTACAAACAGGTGCAACAGAAACCGTATCCTACGATAA
GTTGGTCATGACTACTGGAAGTTGGCCTATAATTCCACCAATACCCGGAATTG
ATGCTGAGAACATTCTACTTTGCAAGAATTATTCTCAAGCGAATGTCATTATC
GAAAAGGCCAAAGATGCGAAAAGAGTCGTTGTCGTTGGTGGTGGCTATATTG
GTATAGAGTTAGTTGAAGCTTTTGTTGAAAGCGGTAAACAGGTGACCCTAGTT
GATGGTCTAGACAGGATTTTGAACAAGTATTTGGACAAACCGTTTACTGATGT
TTTAGAAAAGGAGTTAGTTGATAGAGGTGTGAACTTAGCCTTAGGTGAAAATG
TCCAACAGTTTGTAGCTGATGAACAGGGAAAAGTTGCAAAAGTTATCACTCCA
TCTCAAGAATTCGAAGCAGACATGGTCATAATGTGTGTTGGCTTTAGACCAAA
TACCGAACTTTTGAAAGACAAAGTTGATATGTTGCCTAACGGTGCAATTGAGG
TTAACGAGTATATGCAAACGTCCAATCCAGATATCTTTGCTGCTGGTGATTCA
GCCGTAGTGCATTACAACCCATCGCAAACGAAGAATTATATTCCCTTAGCGAC
TAATGCAGTAAGACAGGGTATGTTGGTGGGGAGAAACTTGACAGAACAGAAA
CTTGCCTATAGAGGCACCCAAGGTACGTCTGGCTTGTACTTGTTCGGTTGGAA
AATTGGCTCAACAGGAGTAACCAAAGAATCGGCAAAATTGAATGGGTTAGAT
GTTGAAGCTACAGTCTTTGAGGATAACTATAGACCTGAATTCATGCCAACAAC
CGAAAAGGTGCTGATGGAGCTGGTGTACGAAAAGGGGACTCAAAGGATAGTA
GGTGGGCAATTGATGTCCAAATACGATATCACTCAATCAGCGAATACACTTTC
ATTGGCTGTACAGAACAAAATGACCGTTGAAGATCTGGCTATTTCAGACTTCT
TCTTTCAACCGCACTTrGACCGTCCTGGAATTACTTAAATTTGCTAGCCCAAG
CAGCTCTGGAGAACATGTAA SEQ ID NO: 26 (=Amino acid NOXE.Ef)
MSVVVVGCTHAGTSAVKSILANHPEAEVTVYERNDNISFLSCGIALYVGGVVKNA
ADLFYSNPEELASLGATVKMEHNVEEINVDDKTVTAKNLQTGATETVSYDKLVM
TTGSWPHPPIPGIDAENILLCKNYSQANVIIEKAKDAKRVWVGGGYIGIELVEAFV
ESGKQVTLVDGLDRILNKYLDKPFTDVLEKELVDRGVNLALGENVQQFVADEOG
KVAKVITPSQEFEADMVIMCVGFRPNTELLKDKVDMLPNGAIEVNEYMQTSNPDI
FAAGDSAVVHYNPSQTKNYIPLATNAVRQGMLVGRNLTEQKLAYRGTQGTSGLY
LFGWKIGSTGVTKESAKLNGLDVEATVFEDNYRPEFNIPTTEKVLMELVYEKGTQ
RIVGGQLMSKYDITQSANTLSLAVQNKMTVEDLAISDFFFQPHFDRPWNYLNLLA
QAALENM SEQ ID NO: 27 (=ADN NOXE.Lb)
ATGTCTAAGGTTACCGTGGTAGGTTGTACACATGCCGGTACTTTTGCAATCAA
ACAGATTTTGGCAGAACATCCTGATGCAGAAGTAACAGTCTATGAGAGAAAT
GACGTGATTAGCTTCTTGTCGTGTGGCATAGCGTTGTACTTGGGTGGGAAAGT
TGCTGACCCTCAAGGGCTTTTCTACTCATCACCAGAAGAGTTACAAAAGCTTG
GGGCAATGTCCAAATGAACCACAACGTTTTAGCGATAGATCCAGATCAAAA
GACTGTTACTGTTGAAGATCTAACGAGTCATGCTCAGACAACAGAATCCTATG
ACAAGTTAGTCATGACTTCAGGTTCTTGGCCGATAGTTCCCAAAATACCAGGT
ATTGACTCCGATAGAGTCAAGCTGTGCAAGAATTGGGCTCATGCACAAGCTTT
GATTGAAGATGCTAAAGAAGCGAAAAGAATTACTGTCATTGGCGCTGGTTATA
TCGGTGCCGAATTGGCCGAAGCGTATTCTACTACAGGTCACGACGTAACGTTG
ATAGACGCAATGGATAGAGTAATGCCCAAATACTTTGATGCAGATTTTACCGA
TGTCATTGAGCAAGATTATCGTGATCATGGAGTGCAATTAGCCTTGAGTGAAA
CTGTTGAATCGTTTACAGACAGTGCTACAGGATTGACCATAAAGACTGACAAG
AATAGTTACGAAACAGATCTTGCCATCTTATGCATTGGCTTTAGACCAAATAC
GGATCTGCTGAAAGGAAAAGTTGATATGGCACCAAATGGTGCTATTATTACCG
ATGACTATATGCGTTCCTCTAATCCGGACATATTTGCTGCAGGAGACTCTGCTG
CAGTTCACTATAACCCTACACACCAGAATGCATATATCCCACTAGCCACAAAT
GCTGTGAGACAAGGTATATTAGTAGGCAAGAATTTGGTCAAACCGACCGTTAA
ATACATGGGTACGCAAAGCTCTTCAGGTCTTGCCCTGTACGATAGGACTATTG
TTTCGACCGGCTTAACGCTAGCAGCAGCTAAACAACAGGGTGTTAATGCTGAA
CAGGTGATCGTTGAGGACAATTATAGACCTGAGTTTATGCCTTCAACTGAACC
CGTGCTAATGAGCTTAGTCTTTGATCCAGATACTCATAGGATCTTAGGAGGAG
```

```
CTTTGATGTCCAAATACGATGTATCCCAGTCTGCAAACACCTTGTCTGTGTGTA
TCCAAAACGAGAATACTATTGATGACTTAGCCATGGTTGATATGCTTTTCCAA
CCTAACTTCGATAGACCATTCAACTATCTAAACATTTTGGCTCAAGCTGCTCAA
GCCAAAGTAGCTCAATCAGTAAACGCCTAG

SEQ ID NO: 28 (=Amino acid NOXE.Lb)
MSKVTVVGCTHAGTFAIKQILAEHPDAEVTVYERNDVISFLSCGIALYLGGKVAD
PQGLFYSSPEELQKLGANVQMNHNVLAIDPDQKTVTVEDLTSHAQTTESYDKLV
MTSGSWPIVPKIPGIDSDRVKLCKNWAHAQALIEDAKEAKRITVIGAGYIGAELAE
AYSTTGHDVTLIDAMDRVMPKYFDADFTDVIEQDYRDHGVQLAIETVESFTDS
ATGLTIKTDKNSYETDLAILCIGFRPNTDLLKGKVDMAPNGAIITDDYMRSSNPDIF
AAGDSAAVHYNPTHQNAYIPLATNAVRQGILVGKNLVKPTVKYMGTQSSSGLAL
YDRTIVSTGLTLAAAKQQGVNAEQVIVEDNYRPEFMPSTEPVLMSLVFDPDTHRIL
GGALMSKYDVSQSANTLSVCIQNENTIDDLAMVDMLFQPNFDRPFNYLNrLAQA
AQAKVAQSVNA SEQ ID NO: 29 (=pENO2)
CGCTCAGCATCTGCTTCTTCCCAAAGATGAACGCGGCGTTATGTCACTAACGA
CGTGCACCAACTTGCGGAAAGTGGAATCCCGTTCCAAAACTGGCATCCACTAA
TTGATACATCTACACACCGCACGCCTTTTTTCTGAAGCCCACTTTCGTGGACTT
TGCCATATGCAAAATTCATGAAGTGTGATACCAAGTCAGCATACACCTCACTA
GGGTAGTTTCTTTGGTTGTATTGATCATTTGGTTCATCGTGGTTCATTAATTTTT
TTTCTCCATTGCTTTCTGGCTTTGATCTTACTATCATTTGGATTTTTGTCGAAGG
TTGTAGAATTGTATGTGACAAGTGGCACCAAGCATATATAAAAAAAAAAAGC
ATTATCTTCCTACCAGAGTTGATTGTTAAAAACGTATTTATAGCAAACGCAATT
GTAATTAATTCTTATTTTGTATCTTTTCTTCCCTTGTCTCAATCTTTTATTTTTAT
TTTATTTTTCTTTTCTTAGTTTCTTTCATAACACCAAGCAACTAATACTATAACA
TACAATAATA SEQ ID NO: 30 (=pTEF2.K1)
CTCTCTCGCAATAACAATGAACACTGGGTCAATCATAGCCTACACAGGTGAAC
AGAGTAGCGTTTATACAGGGTTTATACGGTGATTCCTACGGCAAAAATTTTTC
ATTTCTAAAAAAAAAAGAAAAATTTTTCTTTCCAACGCTAGAAGGAAAAGA
AAAATCTAATTAAATTGATTTGGTGATTTTCTGAGAGTTCCCTTTTTCATATAT
CGAATTTTGAATATAAAAGGAGATCGAAAAAATTTTTCTATTCAATCTGTTTTC
TGGTTTTATTTGATAGTTTTTTTTGTATTATTATTATGGATTAGTACTGGTTTA
TATGGGTTTTTCTGTATAACTTCTTTTTATTTTAGTTTGTTTAATCTTATTTTGA
GTTACATTATAGTTCCCTAACTGCAAGAGAAGTAACATTAAAA SEQ ID NO: 31 (=pTEF3)
GGCTGATAATAGCGTATAAACAATGCATACTTTGTACGTTCAAAATACAATGC
AGTAGATATATTTATGCATATTACATATAATACATATCACATAGGAAGCAACA
GGCGCGTTGGACTTTTAATTTTCGAGGACCGCGAATCCTTACATCACACCCAA
TCCCCCACAAGTGATCCCCCACACACCATAGCTTCAAAATGTTTCTACTCCTTT
TTTACTCTTCCAGATTTTCTCGGACTCCGCGCATCGCCGTACCACTTCAAAACA
CCCAAGCACAGCATACTAAATTTCCCCTCTTTCTTTCCTCTAGGGTGTCGTTAAT
TACCCGTACTAAAGGTTTGGAAAAGAAAAAAGAGACCGCCTCGTTTCTTTTTC
TTCGTCGAAAAAGGCAATAAAAATTTTTATCACGTTTCTTTTTCTTGAAAATTT
TTTTTTTTGATTTTTTTTCTCTTTCGATGACCTCCCATTGATATTTAAGTTAATAA
ACGGTCTTCAATTTCTCAAGTTTCAGTTTCATTTTTCTTGTTCTATTACAACTTT
TTTTACTTCTTGCTCATTAGAAAGAAAGCATAGCAATCTAATCTAAGTTTTAAT
TACAAA SEQ ID NO: 32 (=pADH1)
GGGTGTACAATATGGACTTCCTCTTTTCTGGCAACCAAACCCATACATCGGGA
TTCCTATAATACCTTCGTTGGTCTCCCTAACATGTAGGTGGCGGAGGGGAGAT
ATACAATAGAACAGATACCAGACAAGACATAATGGGCTAAACAAGACTACAC
CAATTACACTGCCTCATTGATGGTGGTACATAACGAACTAATACTGTAGCCCT
AGACTTGATAGCCATCATCATATCGAAGTTTCACTACCCTTTTTCCATTTGCCA
TCTATTGAAGTAATAATAGGCGCATGCAACTTCTTTTCTTTTTTTTCTTTTCTC
TCTCCCCCGTTGTTGTCTCACCATATCCGCAATGACAAAAAAATGATGGAAGA
CACGCACACTACTCTCTAATGAGCAACGGTATACGGCCTTCCTTCCAGTTACTT
GAATTTGAAATAAAAAAAGTTTGCTGTCTTGCTATCAAGTATAAATAGACCT
GCAATTATTAATCTTTTGTTTCCTCGTCATTGTTCTCGTTCCCTTTCTTCCTTGTT
TCTTTTTCTGCACAATATTTCAAGCTATACCAAGCATACAATCAACTATCTCAT
ATACA SEQ ID NO: 33 (=pGPM1)
GCCAAACTTTTCGGTTAACACATGCAGTGATGCACGCGCGATGGTGCTAAGTT
ACATATATATATATATATATATATATATATATATATATAGCCATAGTGATGTCTAA
GTAACCTTTATGGTATATTTCTTAATGTGGAAAGATACTAGCGCGCGCACCCA
CACACAAGCTTCGTTTCTTGAAGAAAAGAGGAAGCTCGCTAAATGGGATT
CCACTTTCCGTTCCCTGCCAGCTGATGGAAAAAGGTTAGTGGAACGATGAAGA
ATAAAAAGAGAGATCCACTGAGGTGAAATTTCAGCTGACAGCGAGTTTCATG
ATCGTGATGAACAATGGTAACGAGTTGTGGCTGTTGCCAGGGAGGGTGGTTCT
CAACTTTTAATGTATGCCAAATCGCTACTTGGGTTGTTATATAACAAAGAA
GAAATAATGAACTGATTCTCTTCCTCTTTCTTGTCCTTTCTTAATTCT
```

SEQUENCES LISTING

TTACCTTCCTTTGTAATTTTTTTTGTAATTATTCTTCTTAATAATCCAAACAAAC
ACACATATTACAATA

SEQ ID NO: 34 (=pFBA1)
ACGCAAGCCCTAAGAAATGAATAACAATACTGACAGTACTAAATAATTGCCT
ACTTGGCTTCACATACGTTGCATACGTCGATATAGATAATAATGATAATGACA
GCAGGATTATCGTAATACGTAATAGTTGAAAATCTCAAAAATGTGTGGGTCAT
TACGTAAATAATGATAGGAATGGGATTCTTCTATTTTTCCTTTTTCCATTCTAG
CAGCCGTCGGGAAACGTGGCATCCTCTCTTTCGGGCTCAATTGGAGTCACGC
TGCCGTGAGCATCCTCTCTTTCCATATCTAACAACTGAGCACGTAACCAATGG
AAAAGCATGAGCTTAGCGTTGCTCCAAAAAAGTATTGGATGGTTAATACCATT
TGTCTGTTCTCTTCTGACTTTGACTCCTCAAAAAAAAAAAATCTACAATCAACA
GATCGCTTCAATTACGCCCTCACAAAAACTTTTTTCCTTCTTCTTCGCCCACGT
TAAATTTTATCCCTCATGTTGTCTAACGGATTTCTGCACTTGATTTATTATAAA
AAGACAAAGACATAATACTTCTCTATCAATTTCAGTTATTGTTCTTCCTTGCGT
TATTCTTCTGTTCTTCTTTTTCTTTTGTCATATATAACCATAACCAAGTAATACA
TATTCAAA

SEQ ID NO: 35 (=pPDC1)
TTATTTACCTATCTCTAAACTTCAACACCTTATATCATAACTAATATTTCTTGA
GATAAGCACACTGCACCCATACCTTCCTTAAAAACGTAGCTTCCAGTTTTTGGT
GGTTCCGGCTTCCTTCCCGATTCCGCTTGCTAAACGCATATTTTTGTTGCCTGG
TGGCATTTGCAAATGCATAACCTATGCATTTAAAAGATTATGTATGCTCTTCT
GACTTTTCGTGTGATGAGGCTCGTGGAAAAAATGAATAATTTATGAATTTGAG
AACAATTTTGTGTTGTTACGGTATTTTACTATGGAATAATCAATCAATTGAGGA
TTTTATGCAAATATCGTTTGAATATTTTTCCGACCCTTTGAGTACTTTTCTTCAT
AATTGCATAATATTGTCCGCTGCCCCTTTTTCTGTTAGACGGTGTCTTGATCTA
CTTGCTATCGTTCAACACCACCTTATTTTCTAACTATTTTTTTTAGCTCATTT
GAATCAGCTTATGGTGATGGCACATTTTTGCATAAACCTAGCTGTCCTCGTTGA
ACATAGGAAAAAAAAATATATAAACAAGGCTCTTTCACTCTCCTTGCAATCAG
ATTTGGGTTTGTTCCCTTTATTTTCATATTTCTTGTCATATTCCTTTCTCAATTAT
TATTTTCTACTCATAACCTCACGCAAAATAACACAGTCAAATCAATCAAA

SEQ ID NO: 36 (=pPGK1)
GTGAGTAAGGAAAGAGTGAGGAACTATCGCATACCTGCATTTAAAGATGCCG
ATTTGGGCGCGAATCCTTTATTTTGGCTTCACCCTCATACTATTATCAGGGCCA
GAAAAAGGAAGTGTTTCCCTCCTTCTTGAATTGATGTTACCCTCATAAAGCAC
GTGGCCTCTTATCGAGAAAGAAATTACCGTCGCTCGTGATTTGTTTGCAAAAA
GAACAAAACTGAAAAAACCCAGACACGCTCGACTTCCTGTCTTCCTATTGATT
GCAGCTTCCAATTTCGTCACACAACAAGGTCCTATTGACGGCTCACAGGTTTT
GTAACAAGCAATCGAAGGTTCTGGAATGCGGGAAAGGGTTTAGTACCACAT
GCTATGATGCCCACTGTGATCTCCAGAGCAAAGTTCGTTCGATCGTACTGTTA
CTCTCTCTCTTTCAAACAGAATTGTCCGAATCGTGTGACAACAACAGCCTGTTC
TCACACACTCTTTTCTTCTAACCAAGGGGTGGTTTAGTTTAGTAGAACCTCGT
GAAACTTACATTTACATATATATAAACTTGCATAAATTGGTCAATGCAAGAAA
TACATATTTGGTCTTTTCTAATTCGTAGTTTTTCAAGTTCTTAGATGCTTTCTTT
TTCTCTTTTTTACAGATCATCAAGGAAGTAATTATCTACTTTTTACAACAAATA
TAAAACA

SEQ ID NO: 37 (=pRPLA1)
TCAAGTTGGATACTGATCTGATCTCTCCGCCCTACTACCAGGGACCCTCATGAT
TACCGCTCGAATGCGACGTTTCCTGCCTCATAAAACTGGCTTGAAAATATTTAT
TCGCTGAACAGTAGCCTAGCTTATAAAAATTTCATTTAATTAATGTAATATGA
AAACTCACATGCCTTCTGTTTCTAAAATTGTCACAGCAAGAAATAACATTACC
ATACGTGATCTTATTAAACTCTAGTATCTTGTCTAATACTTCATTTAAAAGAAG
CCTTAACCCTGTAGCCTCATCTATGTCTGCTACATATCGTGAGGTACGAATATC
GTAAGATGATACCACGCAACTTTGTAATGATTTTTTTTTTTCATTTTTTAAAG
AATGCCTTTACATGGTATITGAAAAAAATATCTTTATAAAGTTTGCGATCTCTT
CTGTTCTGAATAATTTTTAGTAAAAGAAATCAAAAGAATAAAGAAATAGTCCG
CTTTGTCCAATACAACAGCTTAAACCGATTATCTCTAAAATAACAAGAAGAA

SEQ ID NO: 38 (=pTEF1)
GTTTAGCTTGCCTCGTCCCCGCCGGGTCACcCggccaGCGACATGGAGGCCCAGA
ATACCCTCCTTGACAGTCTTGACGTGCGCAGCTCAGGGGCATGATGTGACTGT
CGCCCGTACATTTAGCCCATACATCCCCATGTATAATCATTTGCATCCATACAT
TTTGATGGCCGCACGGCGCGAAGCAAAAATTACGGCTCCTCGCTGCAGACCTG
CGAGCAGGGAAACGCTCCCCTCACAGACGCGTTGAATTGTCCCCACGCCGCGC
CCCTGTAGAGAAATATAAAAGGTTAGGATTTGCCACTGAGGTTCTTCTTTCAT
ATACTTCCTTTTAAAATCTTGCTACGATACAGTTCTCACATCACATCCGAACAT
AAACAACC SEQ ID NO: 39 (=pTDH3)
CTGCTGTAACCCGTACATGCCCAAAATAGGGGGCGGGTTACACAGAATATATA
ACATCGTAGGTGTCTGGGTGAACAGTTTATTCCTGGCATCCACTAAATATAAT
GGAGCCCGCTTTTTAAGCTGGCATCCAGAAAAAAAAGAATCCCAGCACCAA
AATATTGTTTTCTTCACCAACCATCAGTTCATAGGTCCATTCTCTTAGCGCAAC
TACAGAGAACAGGGGCACAAACAGGCAAAAAACGGGCACAACCTCAATGGA GTGATGCAACCTGCCTGGAGTAAATGATGACACAAGGCAATTGACCCACGCA
TGTATCTATCTCATTTTCTTACACCTTCTATTACCTTCTGCTCTCTGATTTGG
AAAAAGCTGAAAAAAAAGGTTGAAACCAGTTCCCTGAAATTATTCCCCTACTT
GACTAATAAGTATATAAAGACGGTAGGTATTGATTGTAATTCTGTAAATCTAT
TTCTTAAACTTCAAATTCTACTTTTATAGTTAGTCTTTTTTTTAGTTTTAAAA
CACCAAGAACTTAGTTTCGAATAAACACACATAAACAAACAAA SEQ ID NO: 40 (=tTHd2)
ATTTAACTCCTTAAGTTACTTTAATGATTTAGTTTTTATTATTAATAATTCATGC
TCATGACATCTCATATACACGTTTATAAAACTTAAATAGATTGAAAATGTATT
AAAGATTCCTCAGGGATTCGATTTTTTGGAAGTTTTTGTTTTTTTTCCTTGAG
ATGCTGTAGTATTTGGGAACAATTATACAATCGAAAGATATATGCTTACATTC
GACCGTTTTAGCCGTGATCATTATCCTATAGTAACATAACCTGAAGCATAACT
GACACTACTATCATCAATACTTGTCACATGA SEQ ID NO: 41 (=tCYC1)
ACAGGCCCCTTTTCCTTTGTCGATATCATGTAATTAGTTATGTCACGCTTACAT
TCACGCCCTCCTCCCACATCCGCTCTAACCGAAAAGGAAGGAGTTAGACAACC
TGAAGTCTAGGTCCCTATTTATTTTTTTTAATAGTTATGTTAGTATTAAGAACG
TTATTTATATTTCAAATTTTTCTTTTTTTTCTGTACAAACGCGTGTACGCATGTA
ACATTATACTGAAAACCTTGCTTGAGAAGGTTTTGGGACGCTCGAAGGCTTTA
ATTTGCAAGCTTCGCAGTTTACACTCTCATC SEQ ID NO: 42 (=tTDH3)
GTGAATTTACTTTAAATCTTGCATTTAAATAAATTTTCTTTTTATAGCTTTATGA
CTTAGTTTCAATTTATATACTATTTAATGACATTTTCGATTCATTGATTGAAA
GCTTTGTGTTTTCTTGATGCGCTATTGCATTGTTCTTTGTCTTTTTCGCCACAT
GTAATATCTGTAGTAGATACCTGATACATTGTGGATGCTGAGTGAAATTTTAG
TTAATAATGGAGGCGCTCTTAATAATTTTGGGGATATTGGCTTTTTTTTTAAA
GTTTACAAATGAATTTTTTCCGCCAGGAT SEQ ID NO: 43 (=tADH1)
ACTAGTTCTAGAGCGGCCGCCACCGCGGTGGGCGAATTTCTTATGATTTATGA
TTTTTATTATTAAATAAGTTATAAAAAAAATAAGTGTATACAAATTTTAAAGT
GACTCTTAGGTTTTAAAACGAAAATTCTTATTCTTGAGTAACTCTTTCCTGTAG
GTCAGGTTGCTTTCTCAGGTATAGCATGAGGTCGCTCTTATTGACCACACCTCT
ACCGGCATGCCGAGCAAATGCCTGCAAATCGCTCCCCATTTCACCCAATTGTA
GATATGCTAACTCCAGCAATGAGTTGATGAATCTCGGTGTGTATTTTATGTCCT
CAGAgGACAACACCTGTTGTAATCGTTCTTCCA SEQ ID NO: 44 (=tTPI1)
GATTAATATAATTATATAAAAATATTATTTTCTTTTCTTTATATCTAGTGTTATG
TAAAATAAATTGATGACTACGGAAAGCTTTTTATATTGTTTCTTTTTCATTCT
GAGCCACTTAAATTTCGTGAATGTTCTTGTAAGGGACGGTAGATTTACAAGTG
ATACAACAAAAAGCAAGGCGCTTTTTCTAATAAAAAGAAGAAAAGCATTTAA
CAATTGAACACCTCTATATCAACGAAGAATATTACTTTTGTCTCTAAATCCTTGT
AAAATGTGTACGATCTCTATATGGGTTACTC SEQ ID NO: 45 (=tMET25)
GTGTGCGTAATGAGTTGTAAAATTATGTATAAACCTACTTTCTCTCACAAGTAC
TATACTTTTATAAAACGAACTTTATTGAAATGAATATCCTTTTTTTCCCTTGTTA
CATGTCGTGACTCGTACTTTGAACCTAAATTGTTCTAACATCAAAGAACAGTG
TTAATTCGCAGTCGAGAAGAAAAATATGGTGAACAAGACTCATCTACTTCATG
AGACTACTTTACGCCTCCTATAAAGCTGTCACACTGGATAAATTTATTGTAGG
ACCAAGTTACAAAAGAGGATGATGGAGGTTT SEQ ID NO: 46 (=tENO2)
GGATCCTAAAGTGCTTTTAACTAAGAATTATTAGTCTTTTCTGCTTATTTTCA
TCATAGTTTAGAACACTTTATATTAACGAATAGTTTATGAATCTATTTAGGTTT
AAAAATTGATACAGTTTTATAAGTTACTTTTTCAAAGACTCGTGCTGTCTATTG
CATAATGCACTGGAAGGGGAAAAAAAAGGTGCACACGCGTGGCTTTTTCTTG
AATTTGCAGTTTGAAAAATAACTACATGGATGATAAGAAAACATGGAGTACA
GTCACTTTGAGAACCTTCAATCAGCTGGTAACGTCTTC SEQ ID NO: 47 (=tMET3)
TCGTCATAAAATGCTCCCATCTCAAAAGTAGGGCAAAATTCATGATCGACCGC
GCAAAATAAATAGATTTGCAAATAAGTTTTGTATGTACATTTATTAATATATAT
AATATATCAAAAGAAAAAATCAAAAAAAAAAAAAAAAAAATTGCACTCT
TATTCAGTCATCAATTACAAAACCTAGAGATAGCGATGGTGCATATTCAATAA
AAAACTCCTTATACTGTCGAGAAAGCTTATTATTGGTACTTCTCGAAGATACT
AAAAAAGGTTAATTTTTGGAGACGGAGGCAATAGC SEQ ID NO: 48 (=tPGK1)
ATTGAATTGAATTGAAATCGATAGATCAATTTTTTTTCTTTTCTCTTTCCCCATCC
TTTACGCTAAAATAATAGTTTATTTTATTTTTTGAATATTTTTTATTTATATACG
TATATATAGACTATTATTTATCTTTTAATGATTATTAAGATTTTTATTAAAAAA
AAATTCGCTCCTCTTTTAATGCCTTTATGCAGTTTTTTTTTCCCATTCGATATTT

```
CTATGTTCGGGTTCAGCGTATTTTAAGTTTAATAACTCGAAAATTCTGCGTTCG
TTAAAGCTTTCGAGAAGGATATTATTTA

SEQ ID NO: 49 (=pPYK1)
AAAAGGAAAGATTATTGAAAGAGAAAGAAAGAAAAAAAAAAAAATGTACACC
CAGACATCGGGCTTCCACAATTTCGGCTCTATTGTTTTCCATCTCTCGCAACGG
CGGGATTCCTCTATGGCGTGTGATGTCTGTATCTGTTACTTAATCCAGAAACTG
GCACTTGACCCAACTCTGCCACGTGGGTCGTTTTGCCATCGACAGATTGGGAG
ATTTTCATAGTAGAATTCAGCATGATAGCTACGTAAATGTGTTCCGCACCGTC
ACAAAGTGTTTTCTACTGTTCTTTCTTCTTTTCGTTCATTCAGTTGAGTTGAGTGA
GTGCTTTGTTCAATGGATCTTAGCTAAAATGCATATTTTTTCTCTTGGTAAATG
AATGCTTGTGATGCTTCCAAGTGATTTCCTTTCCTTCCCATATGATGCTAGGT
ACCTTTAGTGTCTTCCTAAAAAAAAAAAAAGGCTCGCCATCAAAACGATATTC
GTTGGCTTTTTTTTCTGAATTATAAATACTCTTTGGTAACTTTTCATTTCCAAGA
ACCTCTTTTTTTCCAGTTATATCATGGTCCCCTTTCAAAGTTATTCTCTACTCTTT
TTCATATTCATTCTTTTCATCCTTTGGTTTTTTATTCTTAACTTGTTTATTATTC
TCTCTTGTTTCTATTTACAAGACACCAATCAAAACAAATAAAACATCATCACA

SEQ ID NO: 50 (=pTPI1)
ATTTAAACTGTGAGGACCTTAATACATTCAGACACTTCTGCGGTATCACCCTA
CTTATTCCCTTCGAGATTATATCTAGGAACCCATCAGGTTGGTGGAAGATTAC
CCGTTCTAAGACTTTTCAGCTTCCTCTATTGATGTTACACCTGGACACCCCTTT
TCTGGCATCCAGTTTTTAATCTTCAGTGGCATGTGAGATTCTCCGAAATTAATT
AAAGCAATCACACAATTCTCTCGGATACCACCTCGGTTGAAACTGACAGGTGG
TTTGTTACGCATGCTAATGCAAAGGAGCCTATATACCTTTGGCTCGGCTGCTGT
AACAGGGAATATAAAGCTTCAGCATAATTTAGGAGTTTAGTGAACTTGCAACA
TTTACTATTTTCCCTTCTTACGTAAATATTTTTCTTTTTAATTCTAAATCAACTCT
TTTTCAATTTTTTGTTTGTATTCTTTTCTTGCTTAAATCTATAACTACAAAAAAC
ACATACATAAACTAAAA

SEQ ID NO: 51 (=tDIT1)
TAAAGTAAGAGCGCTACATTGGTCTACCTTTTTGTTCTTTTACTTAAACATTAG
TTAGTTCGTTTTCTTTTTCTCATTTTTTTATGTTTCCCCCCCAAAGTTCTGATTTT
ATAATATTTTATTTCACACAATTCCATTTAACAGAGGGGGAATAGATTCTTTAG
CTTAGAAAATTAGTGATCAATAATATATTTGCCTTTCTTTTCATCTTTTCAGTGAT
ATTAATGGTTTCGAGACACTGCAATGGCCCTAGTTGTCTAAGAGGATAGATGT
TACTGTCAAAGATGATATTTTGAATTTC

SEQ ID NO: 52 (=loxP)
ATAACTTCGTATAATGTATGCTATACGAAGTTA

SEQ ID NO: 53 (=nucleic acid HAA-1)
ATGGTCTGATAAATGGCATAAAGTATGCCTGTGAGAGGTGCATAAGAGGCC
ATAGAGTAACAACATGCAATCATACAGATCAACCGCTTATGATGATCAAACCC
AAAGGTAGACCTTCCACTACATGCGACTATTGTAAACAACTTCGAAAAAACAA
GAATGCAAATCCTGAAGGTGTTTGCACGTGTGGCCGGCTAGAGAAGAAAAA
CTGGCACAGAAAGCCAAAGAAGAAGCAAGAGCTAAAGCCAAAGAAAAACAA
ATTTAAACTGTGAGGACCTTAATACATTCAGACACTTCTGCGGTATCACCCTA
AGAAAACAGTGTACCTGCGGGACTGATGAGGTTTGCAAATATCATGCTCAAA
AGAGACATCTAAGAAAGTCCCCTTCAAGTTCTCAAAAGAAAGGAAGATCCAT
TTCTCGTTCTCAACCATGTTTGAAAGGGTATTGTCTTCTACTTCACTTGACAG
CAATATGTTATCCGGCCACGGAGCACTATCAGATACCTCTAGCATACTGACGA
GCACATTTTTAGACAGTGAGCCGGGTGTTGGTAAAATTTCAAAAGATTACCAT
CATGTCCCTTCATTGGCCTCCATTTCATCCTTACAATCCTCGCAATCGTTAGAT
CAAAATTTCAGTATACCACAAAGCCCGCCGTTATCTTCAATGTCATTTAATTTT
CTCACGGGAAATATCAATGAAACCAACCAAAATCACAGTAATCATCAGCATTC
AAAATCAGGCAATAACTGGCAAGATAGTTCGGTAAGCTTGCCAGCGAAAGCT
GATTCACGTCTTAACATGATGGATAAAAACAACTCTGTGGGTCTTGACCTATT
AGGCCATTCAAAACGAATATCGCCGATATCAAACTCTCGTGTGGGCGAAGTTA
GCGTTCCGCTAGAAGAATATATTCCTTCTGACATTGATGGGGTTGGAAGAGTT
ACTGATAAAAGCTCTTTGGTCTACGATTGGCCATTTGATGAAAGTATTGAGAG
AAATTTCAGTACAACCGCAACCGCTGCAACTGGTGAAAGTAAGTTCGACATTA
ACGACAACTGTAATAGAATTAATAGCAAAAGTTATAGTAAGACTAATAGTAT
GAATGGAAACGGTATGAACAATAGCAATAATAATAATATCAACAGTAATGGC
AACGACAAGAACAATAACAACTCTTCTAGACAAGAACATCAAGGAAATGGAC
TATTTGACATGTTTACAGATTCATCGTCGATTTCAACGCTTTCCCGTGCAAACT
TATTATTGCAAGAAAAAATTGGTTCGCAAGAAAACTCTGTCAAACAAGAAAA
CTATTCGAAAAATCCTCAACTTCGTCATCAATTAACTTCCAGAAGTAGATCATT
TATTCATCATCCGGCAAACGAGTATTTGAAGAATACTTTTGGAAATTCACATA
GTAATGCATCGGAAAGGGAGTTGAAGTGCTATCTTTGACACCGAGTTTTATG
GATATTCCCGAAAAAGAAAGAAAACGGAAAGATCGCCATCATCCAATTACA
TTACTGACAGACCTTTCACTCGAAAACCTAGATCTTCTAGCATTGACGTAAAC
CATAGGTATCCACCTATGGCACCAACAACCGTAGCGACATCTCCCGGTGCATT
GAACAATGCCGTAGCAAGCAATCTCGACGATCAACTGAGTTTAACATCACTAA
ACTCTCAGCCATCATCGATAGCAAATATGATGATGGACCCTTCAAACCTAGCT
GAGCAAAGTTCTATTCATTCAGTTCCTCAGTCAATAAACTCTCCGAGAATGCC
TAAAACTGGAAGTCGCCAAGACAAGAACATTCACACTAAGAAGGAAGAAAGA
```

```
AATCCGCTAAATAACATACACGATCTGTCACAATTGGAAAATGTACCAGACGA
GATGAACCAATGTTCTCCCCACCATTAAAAAGTATGAATAGACCGGATGCCA
TAAGGGAAAATTCATCTAGTAGTAATTTCATAATCCAAGGAAATAGCATGATC
TCTACGCCTTCCGGAAGGAATGACCTTCCAGATACCTCTCCAATGAGTAGTAT
TCAAACAGCGTCACCACCAAGTCAATTACTGACCGATCAAGGATTTGCGGATT
TGGATAATTTCATGTCTTCGTTATGA

SEQ ID NO: 54 (=amino acid HAA-1)
MVLINGIKYACERCIRGHRVTTCNHTDQPLMMIKPKGRPSTTCDYCKQLRKNKN
ANPEGVCTCGRLEKKKLAQKAKEEARAKAKEKQRKQCTCGTDEVCKYHAQKRH
LRKSPSSSQKKGRSISRSQPMFERVLSSTSLDSNMLSGHGALSDTSSILTSTFLDSEP
GVGKISKDYHHVPSLASISSLQSSQSLDQNFSTPQSPPLSSMSFNFLTGNINETNQNH
SNHQHSKSGNNWQDSSVSLPAKADSRLNMMDKNNSVGLDLLGHSKRISPISNSR
VGEVSVPLEEYIPSDIDGVGRVTDKSSLVYDWPFDESIERNFSTTATAATGESKFDI
NDNCNRINSKSYSKTNSMNGNGMNNSNNNNINSNGNDKNNNNSSRQEHQGNGL
FDMFTDSSSISTLSRANLLLQEKIGSQENSVKQENYSKNPQLRHQLTSRSRSFIHHP
ANEYLICNTFGNSHSNDIGKGVELSLTPSFMDIPEKERETERSPSSNYITDRPFTRK
PRSSSIDVNHRYPPMAPTTVATSPGALNNAVASNLDDQLSLTSLNSQPSSIANMM
MDPSNIEQSSIHSVPQSINSPRMPKTGSRQDKNIHTKKEERNPLNNIHDLSQLEN
VPDEMNQMFSPPLKSMNRPDAIRENSSSSNFIIQGNSMISTPSGRNDLPDTSPMSSI
QTASPPSQLLTDQCFADLDNFMSSL SEQ ID NO: 55 (=nuclcic acids LEU2.K1)
ATGTCTAAGAATATCGTTGTCCTACCGGGTGATCACGTCGGTAAAGAAGTTAC
TGACGAAGCTATTAAGGTCTTGAATGCCATTGCTGAAGTCCGTCCAGAAATTA
AGTTCAATTTCCAACATCACTTGATCGGGGGTGCTGCCATCGATGCCACTGGC
ACTCCTTTACCAGATGAAGCTCTAGAAGCCTCTAAGAAAGCCGATGCTGTCTT
ACTAGGTGCTGTTGGTGGTCCAAAATGGGGTACGGGCGCAGTTAGACCAGAA
CAAGGTCTATTGAAGATCAGAAAGGAATTGGGTCTATACGCCAACTTGAGACC
ATGTAACTTTGCTTCTGATTCTTTACTAGATCTTTCTCCTTTGAAGCCCTGAATAT
GCAAAGGGTACCGATTTCGTCGTCGTTAGAGAATTGGTTGGTGGTATCTACTT
TGGTGAAAGAAAAGAAGATGAAGGTGACGGAGTTGCTTGGGACTCTGAGAAA
TACAGTGTTCCTGAAGTTCAAAGAATTACAAGAATGGCTGCTTTCTTGGCATT
GCAACAAAACCCACCATTACCAATCTGGTCTCTTGACAAGGCTAACGTGCTTG
CCTCTTCCAGATTGTGGAGAAAGACTGTTGAAGAAACCATCAAGACTGAGTTC
CCACAATTAACTGTTCAGCACCAATTGATCGACTCTGCTGCTATGATTTTGTT
AAATCACCAACTAAGCTAAACGGTGTTGTTATTACCAACAACATGTTTGGTGA
TATTATCTCCGATGAAGCCTCTGTTATTCCAGGTTCTTTGGGTTTATTACCTTCT
GCATCTCTAGCTTCCCTACCTGACACTAACAAGGCATTCGGTTTGTACGAACC
ATGTCATGGTTCTGCCCCAGATTTACCAGCAAACAAGGTTAACCCAATTGCTA
CCATCTrATCTGCAGCTATGATGTTGAAGTTATCCTTGGATTTGGTTGAAGAAG
GTAGGGCTCTTGAAGAAGCTGTTAGAAATGTCTTGGATGCAGGTGTCAGAACC
GGTGACCTTGGTGGTTCTAACTCTACCACTGAGGTTGGCGATGCTATCGCCAA
GGCTGTCAAGGAAATCTTGGCTTAA SEQ ID NO: 56 (=amino acid LEU2.K1)
MSKNIVVLPGDHVGKEVTDEAIKVLNAIAEVRPEIKFNFQHHLIGGAAIDATGTPL
PDEALEASKKADAVLLGAVGGPKWGTGAVRPEQGLLKIRKELGLYANLRPCNFA
SDSLLDLSPLKPEYAKGTDFVWRELVGGIYFGERKEDEGDGVAWDSEKYSVPEV
QRTITIMAAFLALQQNPPLPIWSLDKANVLASSRLWRKTVEETIKTEFPQLTVQHQL
IDSAAMILVKSPTKLNGWITNNMFGDNSDEASVIPGSLGLLPSASLASLPDTNKAP
GLYEPCHGSAPDLPANKVNPIATILSAAMMLKLSLDLVEEGRALEEAVRNVLDAG
VRTGDLGGSNSTTEVGDAIAKAVKEILA
```

The invention claimed is:

1. A recombinant yeast having a reduced pyruvate decarboxylase activity, in the genome of which has been inserted:
   one or more nucleic acids encoding an acetolactate synthase or ALS,
   one or more nucleic acids encoding an acetolactate decarboxylase or ALD,
   one or more nucleic acids encoding a butanediol dehydrogenase or BDH, and
   two or more copies of nucleic acids encoding a NADH oxidase or NOXE,
   wherein the nucleic acid(s) encoding the acetolactate synthase or ALS is/are nucleic acid(s) selected from the group consisting of sequences having at least 65% nucleic acid identity with the nucleic acid sequences SEQ ID NO: 1, 3 and 5,
   wherein the nucleic acid(s) encoding the acetolactate decarboxylase or ALD is/are nucleic acid(s) selected from the group consisting of sequences having at least 36% nucleic acid identity with the nucleic acid sequences SEQ ID NO: 7, 9 and 11,
   wherein the nucleic acid(s) encoding the butanediol dehydrogenase or BDH is/are nucleic acid(s) selected from the group consisting of sequences having at least 63% nucleic acid identity with the nucleic acid sequences SEQ ID NO: 13, 15, 17 and 19, and
   wherein the nucleic acid(s) encoding the NADH oxidase or NOXE is/are nucleic acid(s) selected from the group consisting of sequences having at least 80% nucleic acid identity with the nucleic acid sequences SEQ ID NO: 21, 23, 25 and 27.

2. The recombinant yeast according to claim 1, wherein the said recombinant yeast comprises one or more DNA constructs selected in a group comprising the following formulae:
   (I) 5'-[Gene 1]$_{x1}$-3' and 5'-[Gene 2]$_{x2}$-3' and 5'-[Gene 3]$_{x3}$-3' and 5'-[Gene 4]$_{x4}$-3',
   (II) 5'-[Gene 1]$_{x1}$-[Gene 2]$_{x2}$-[Gene 3]$_{x3}$-3' and 5'-[Gene 4]$_{x4}$-3',
   (III) 5'-[Gene 1]$_{x1}$-[Gene 2]$_{x2}$-3' and 5'-[Gene 3]$_{x3}$-[Gene 4]$_{x4}$-3',
   (IV) 5'-[Gene 1]$_{x1}$-[Gene 2]$_{x2}$-[Gene 3]$_{x3}$-[Gene 4]$_{x4}$-3', and
   a combination thereof,
   wherein:
      "Gene 1" means a nucleic acid selected from a group comprising ALS, ALD, BDH or NOXE;
      "Gene 2" means a nucleic acid selected from a group comprising ALS, ALD, BDH or NOXE but different from gene 1;
      "Gene 3" means a nucleic acid selected from a group comprising ALS, ALD, BDH or NOXE but different from genes 1 and 2;
      "Gene 4" means a nucleic acid selected from a group comprising ALS, ALD, BDH or NOXE but different from genes 1 to 3;
      "ALS" is a nucleic acid encoding an acetolactate synthase;
      "ALD" is a nucleic acid encoding an acetolactate decarboxylase;
      "BDH" is a nucleic acid encoding a butanediol dehydrogenase;
      "NOXE" is a nucleic acid encoding a NADH oxidase;
      each of "x1", "x2", "x3" and "x4", one independently from the others, represents an integer ranging from 0 to 50, and
   provided that said recombinant yeast comprises at least one nucleic acid encoding for each of ALS, ALD, BDH and NOXE.

3. The recombinant yeast according to claim 2, wherein the said recombinant yeast comprises at least one DNA construct of formula (II), wherein "Gene 4" means a nucleic acid encoding NADH oxidase.

4. The recombinant yeast according to claim 2, wherein the said recombinant yeast comprises at least one DNA construct(s) of formula (IIa), identical or different, wherein each formula (IIa) has the following formula:
   (IIa) 5'-[(prom5)$_{y1}$-Gene 1-term5]$_{x5}$-[prom1-Gene 1-term 1]$_{x1}$-[prom2-Gene 2-term2]$_{x2}$-[prom3-Gene 3-(term3)$_{z1}$]$_{x3}$-3' and 5'-[(prom4)$_{y2}$-Gene 4-(term4)$_{z2}$]$_{x4}$-3'
   wherein:
      Gene 1, Gene 2, Gene 3 and Gene 4 are such as defined in claim 2, and "x1", "x2", "x3" and "x4" are such as defined in claim 2;
      "x5" represents an integer equal to 0 or 1;
      "y1", "y2", "z1" and "z2", one independently from the others, represent an integer equal to 0 or 1;
      when said recombinant yeast comprises at least two DNA constructs of formula (IIa), then "x1" to "x5", "y1", "y2", "z1" and "z2" may be identical or different;
      "prom 1" is a regulatory sequence which controls the expression of the sequence encoding the gene 1;
      "prom 2" is a regulatory sequence which controls the expression of the sequence encoding the gene 2;
      "prom 3" is a regulatory sequence which controls the expression of the sequence encoding the gene 3;
      "prom 4" is a regulatory sequence which controls the expression of the sequence encoding the gene 4;
      "prom5" is a regulatory sequence which controls the expression of Gene 1, said prom5 being identical or different from prom1;

"term 1" is a transcription terminator sequence that ends expression of the sequence encoding the gene 1;

"term2" is a transcription terminator sequence that ends expression of the sequence encoding the gene 2;

"term3" is a transcription terminator sequence that ends expression of the sequence encoding the gene 3;

"term4" is a transcription terminator sequence that ends expression of the sequence encoding the gene 4; and "term5" is a transcription terminator sequence that ends expression of Gene 1, said term5 being identical or different from term 1.

5. The recombinant yeast according to claim 2, wherein the said recombinant yeast comprises at least one DNA construct(s) of formula (IIb), identical or different, wherein each formula (IIb) has the following formula:

(IIb) 5'-[(prom5)$_{y1}$-ALS-term5]$_{x5}$-[prom1-ALS-term1]$_{x1}$-[prom2-ALD-term2]$_{x2}$-[prom3-BDH-(term3)$_{z1}$]$_{x3}$-3' and 5'-[(prom4)$_{y2}$-NOXE-(term4)$_{z2}$]$_{x4}$-3' wherein:

"x5" represents an integer equal to 0 or 1; and "y1", "y2", "z1" and "z2" one independently from the others, represent an integer equal to 0 or 1;

when said recombinant yeast comprises at least two DNA constructs of formula (III)), then "x1" to "x5", "y1", "y2", "z1" and "z2" may be identical or different;

"prom 1" is a regulatory sequence which controls the expression of the sequence encoding the acetolactate synthase;

"prom 2" is a regulatory sequence which controls the expression of the sequence encoding the acetolactate decarboxylase;

"prom 3" is a regulatory sequence which controls the expression of the sequence encoding the butanediol dehydrogenase;

"prom 4" is a regulatory sequence which controls the expression of the sequence encoding the NADH oxidase;

"prom5" is a regulatory sequence which controls the expression of the sequence encoding the acetolactate synthase, said prom5 being identical or different from prom 1;

"term 1" is a transcription terminator sequence that ends expression of the sequence encoding the acetolactate synthase;

"term2" is a transcription terminator sequence that ends expression of the sequence encoding the acetolactate decarboxylase;

"term3" is a transcription terminator sequence that ends expression of the sequence encoding the butanediol dehydrogenase;

"term4" is a transcription terminator sequence that ends expression of the sequence encoding the NADH oxidase; and "term5" is a transcription terminator sequence that ends expression of the sequence encoding the acetolactate synthase, said term5 being identical or different from term 1.

6. The recombinant yeast according to claim 2, wherein the recombinant yeast comprises at least two DNA constructs of formula (II), (IIa) or (IIb), provided that all copies of NOXE's nucleic acid are located at a single of the at least two DNA constructs of formula (II), (IIa) or (IIb).

7. The recombinant yeast according to claim 2, wherein the said recombinant yeast comprises at least two DNA constructs of the following formulae (IIc) and (IId):

(IIc) 5'-[(prom5)$_{y1}$-ALS-term5]$_{x5}$-[prom 1-ALS-term 1]$_{x1}$-[prom2-ALD-term2]$_{x2}$-[prom3-BDH-(term3)$_{z1}$]$_{x3}$-3' and 5'-[(prom4)$_{y2}$-NOXE-(term4)$_{z2}$]$_{x6}$-3'; and (IId) 5'-[(prom5)$_{y1}$-ALS-term5]$_{x5}$-[prom 1-ALS-term 1]$_{x1}$-[prom2-ALD-term2]$_{x2}$-[prom3-BDH-(term3)$_{z1}$]$_{x3}$-3' and 5'-[(prom4)$_{y2}$-NOXE-(term4)$_{z2}$]$_{x7}$-3';

wherein:

"prom 1" is a regulatory sequence which controls the expression of the sequence encoding the gene 1;

"prom 2" is a regulatory sequence which controls the expression of the sequence encoding the gene 2;

"prom 3" is a regulatory sequence which controls the expression of the sequence encoding the gene 3;

"prom 4" is a regulatory sequence which controls the expression of the sequence encoding the gene 4;

"prom5" is a regulatory sequence which controls the expression of Gene 1, said prom5 being identical or different from prom1;

"term 1" is a transcription terminator sequence that ends expression of the sequence encoding the gene 1;

"term2" is a transcription terminator sequence that ends expression of the sequence encoding the gene 2;

"term3" is a transcription terminator sequence that ends expression of the sequence encoding the gene 3;

"term4" is a transcription terminator sequence that ends expression of the sequence encoding the gene 4; and "term5" is a transcription terminator sequence that ends expression of Gene I, said term5 being identical or different from term 1;

"x5" represents an integer equal to 0 or 1,

"y1", "y2", "z1" and "z2" one independently from the others, represent an integer equal to 0 or 1;

"x1" to "x3", "x5", "y1", "y2", "z1" and "z2" for each formulae (IIc) and (IId) being identical or different; and "x6" and "x7" represent integers ranging from 0 to 50, provided that one among "x6" and "x7" represents 0.

8. The recombinant yeast according to claim 1, wherein each of nucleic acids encoding acetolactate synthase, acetolactate decarboxylase, butanediol dehydrogenase, and NADH oxidase is under the control of a promoter, identical or different, said promoters consisting of a sequence of nucleic acid selected from the group consisting of sequences having at least 80% nucleic acid identity with the nucleic acid sequences SEQ ID NO: 29 to 39, 49 and 50.

9. The recombinant yeast according to claim 1, wherein each of nucleic acids encoding acetolactate synthase, acetolactate decarboxylase, butanediol dehydrogenase, and NADH oxidase is under the control of a transcription terminator, identical or different, said transcription terminators consisting of a sequence of nucleic acid selected from the group consisting of sequences having at least 80% nucleic acid identity with the nucleic acid sequence of SEQ ID NO: 40 to 48.

10. The recombinant yeast according to claim 1, wherein the pyruvate decarboxylase activity is reduced by disruption of at least one pdc gene.

11. A method for producing 2,3-butanediol (BDO), said method comprising the steps of:

(a) culturing a recombinant yeast such as defined in claim 1 in an appropriate culture medium; and (b) recovering the 2,3-butanediol (BDO).

12. The method according to claim 11, wherein the said culture medium comprises a carbon source.

\* \* \* \* \*